(12) United States Patent
Yoo et al.

(10) Patent No.: US 11,981,656 B2
(45) Date of Patent: May 14, 2024

(54) ORGANIC COMPOUND, ORGANIC LIGHT EMITTING DIODE AND ORGANIC LIGHT EMITTING DISPLAY DEVICE INCLUDING THE COMPOUND

(71) Applicant: LG DISPLAY CO., LTD., Seoul (KR)

(72) Inventors: Mi-Sang Yoo, Paju-si (KR); Kyung-Jin Yoon, Paju-si (KR); Hye-Gun Ryu, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 609 days.

(21) Appl. No.: 16/939,403

(22) Filed: Jul. 27, 2020

(65) Prior Publication Data
US 2021/0024496 A1  Jan. 28, 2021

(30) Foreign Application Priority Data
Jul. 25, 2019 (KR) .................. 10-2019-0090292

(51) Int. Cl.
*C07D 401/14* (2006.01)
*C07D 405/14* (2006.01)
*C07D 409/14* (2006.01)
*H10K 85/60* (2023.01)
*H10K 50/11* (2023.01)

(52) U.S. Cl.
CPC ......... *C07D 401/14* (2013.01); *C07D 405/14* (2013.01); *C07D 409/14* (2013.01); *H10K 85/654* (2023.02); *H10K 85/6572* (2023.02); *H10K 85/6574* (2023.02); *H10K 50/11* (2023.02)

(58) Field of Classification Search
CPC .. C07D 401/14; C07D 405/14; C07D 409/14; C07D 401/10; H10K 85/654; H10K 85/6572; H10K 85/6574; H10K 50/11; H10K 59/12; H10K 50/12; H10K 85/657; C09K 11/06; C09K 2211/1029; C09K 2211/1088
USPC ....................................................... 428/690
See application file for complete search history.

(56) References Cited

U.S. PATENT DOCUMENTS 10,844,085 B2 * 11/2020 Ji ..................... H10K 50/16
11,056,658 B2 * 7/2021 Tsai .................. C09K 11/06
2018/0282356 A1  10/2018 Ji et al.

FOREIGN PATENT DOCUMENTS

| CN | 108690087 A | 10/2018 |
| KR | 10-2014-0124654 A | 10/2014 |
| KR | 10-2015-0137400 A | 12/2015 |
| WO | 2017/122978 A1 | 7/2017 |

OTHER PUBLICATIONS

CAS reg. No. 2580888-42-0, Feb. 2, 2021. (Year: 2021).*
Isotopes of hydrogen, Wikipedia, Feb. 9, 2023, pp. 1-4. (Year: 2023).*
Dec. 1, 2022 Office Action issued in Chinese Patent Application 202010708721.3.

* cited by examiner

*Primary Examiner* — Douglas J McGinty
(74) *Attorney, Agent, or Firm* — Morgan, Lewis & Bockius LLP

(57) ABSTRACT

An organic compound having the following structure of Chemical Formula, and an organic light emitting diode and an organic light emitting display device including the organic compound are disclosed. The organic light emitting diode and the organic light emitting display device can improve its luminous efficiency and color purity, reduce its driving voltage and enhance its luminous efficiency and luminous lifetime by applying the organic compound.

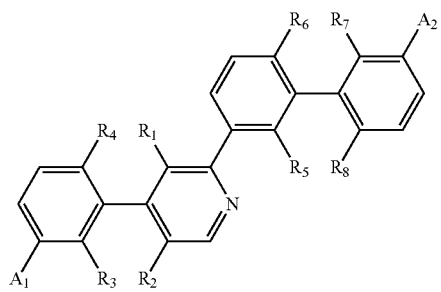

24 Claims, 10 Drawing Sheets

ORGANIC COMPOUND, ORGANIC LIGHT EMITTING DIODE AND ORGANIC LIGHT EMITTING DISPLAY DEVICE INCLUDING THE COMPOUND

CROSS-REFERENCE TO RELATED APPLICATIONS

This application claims the benefit under 35 U.S.C. § 119(a) of Korean Patent Application No. 10-2019-0090292, filed in the Republic of Korea on Jul. 25, 2019, which is incorporated herein by reference in its entirety.

BACKGROUND

Technical Field

The present disclosure relates to an organic compound, and more specifically, to an organic compound having an higher excited triplet energy level and an organic light emitting diode and an organic light emitting display device including the compound.

Discussion of the Related Art

As display devices have became larger, there exists a need for a flat display device with a lower space requirement. Among the flat display devices, a display device using an organic light emitting diode (OLED) has come into the spotlight and been developed rapidly.

In the OLED, when electrical charges are injected into an organic emissive layer between an electron injection electrode, i.e. cathode and a hole injection electrode, i.e. anode, electrical charges are combined to be paired, and then emit light as the combined electrical charges disappear. The OLED can be formed even on a flexible transparent substrate such as a plastic substrate. In addition, the OLED can be driven at a low voltage of 10 V or less. Besides, the OLED has relatively low power consumption for driving compared to plasma panel and inorganic electroluminescent devices, and its color purity is very high. Further, since the OLED can display various colors such as red, green, blue and the likes, the OLED display device has attracted a lot of attention as a next-generation display device that can replace a liquid crystal display device (LCD).

The organic emissive layer comprises an emitting material layer (EML) which comprises a dopant for electroluminescence. The EML consisting of only the dopant shows extremely reduced luminous efficiency owing to concentration quenching, thus it is limited to applying to the display devices. Accordingly, the EML usually further comprises a host which has higher excited singlet and triplet energy levels compared to excited singlet and triplet energy levels of the dopant. However, the convention hosts applied into the OLED has not implemented enough luminous time and luminous efficiency, thus its commercial applications have been limited.

SUMMARY

Accordingly, embodiments of the present disclosure are directed to an organic compound, an organic light emitting diode, and an organic light emitting display device including the organic compound that substantially obviates one or more of the problems due to the limitations and disadvantages of the related art.

An object of the present disclosure is to provide an organic compound having enhanced luminous efficiency and increased luminous lifetime, and an organic light emitting diode and an organic light emitting display device including the organic compound.

Another object of the present is to provide an organic light emitting diode that can reduce its driving voltage and power consumption and enhance its luminous lifetime and an organic light emitting display device including the organic light emitting diode.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described, the present disclosure provides an organic compound having the following structure of Chemical Formula 1:

[Chemical Formula 1]

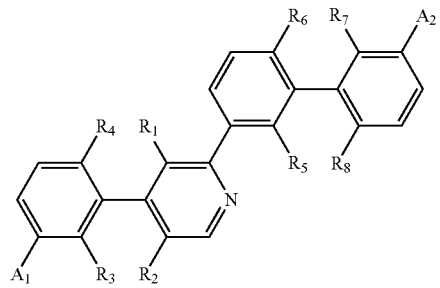

wherein each of $R_1$ to $R_8$ is independently protium, deuterium, tritium, $C_1$-$C_{10}$ alkyl, $C_6$-$C_{30}$ aryl or $C_3$-$C_{30}$ hetero aryl; and each of $A_1$ and $A_2$ is independently protium, deuterium, tritium, or an unsubstituted or substituted hetero aromatic group having one to three hetero aromatic moieties.

At least one of $R_1$ to $R_4$ may be selected from the group consisting of $C_1$-$C_{10}$ alkyl, $C_6$-$C_{30}$ aryl and $C_3$-$C_{30}$ hetero aryl and at least one of $R_5$ to $R_8$ may be selected from the group consisting of $C_1$-$C_{10}$ alkyl, $C_6$-$C_{30}$ aryl and $C_3$-$C_{30}$ hetero aryl.

Each of $A_1$ and $A_2$ may be independently selected from the group consisting of unsubstituted or substituted carbazolyl, unsubstituted or substituted dibenzofuryl and unsubstituted or substituted dibenzothiophenyl.

As an example, each of $A_1$ and $A_2$ is independently selected from the following Chemical Formula 2:
[Chemical Formula 2]
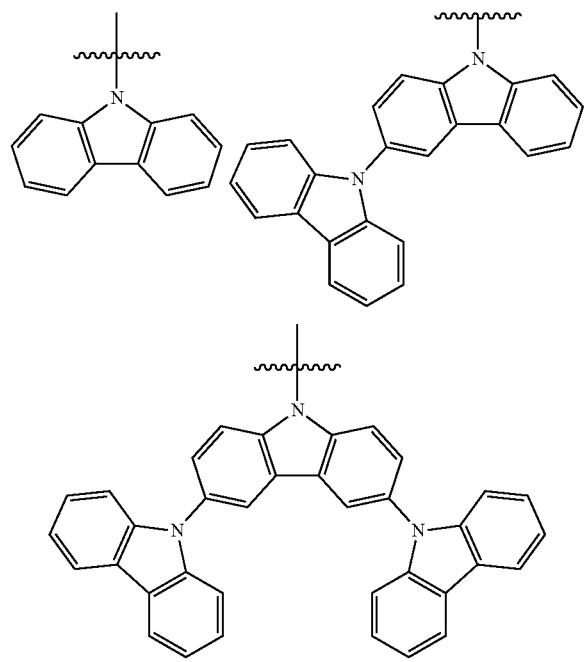
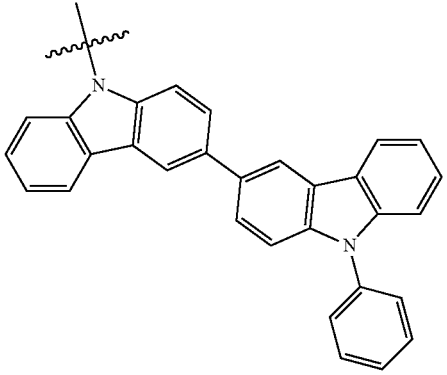
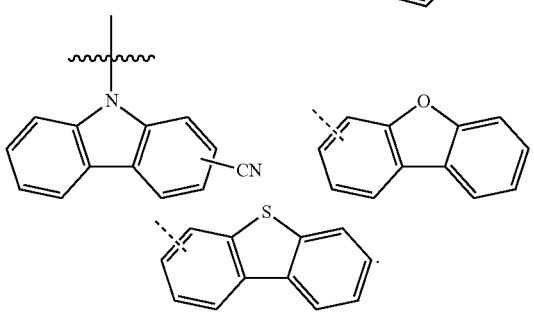
For example, each of $R_1$ and $R_5$, $R_2$ and $R_6$, $R_3$ and $R_7$, $R_4$ and $R_8$ may be identical.
The organic compound may have one of the following Chemical Formula 3:
[Chemical Formula 3]
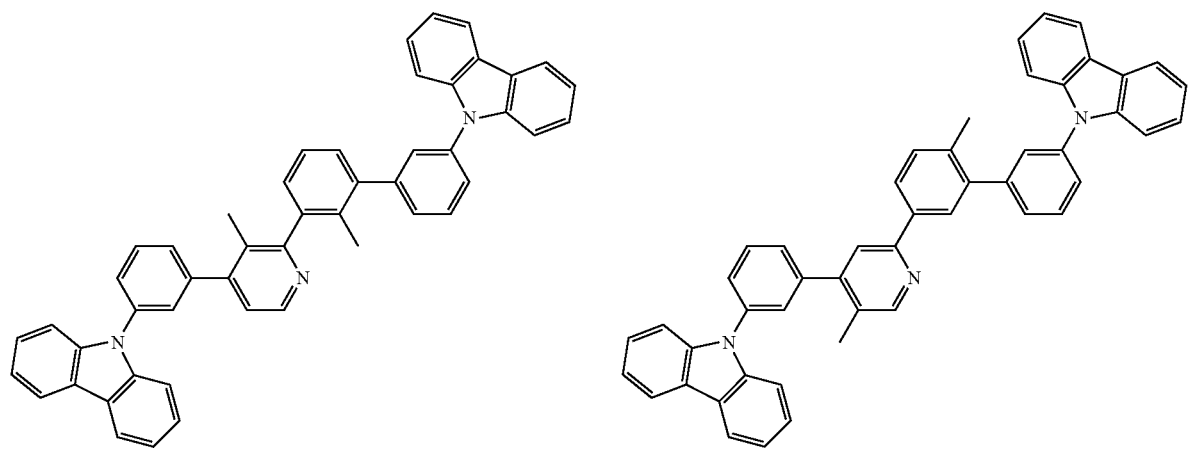

-continued
3
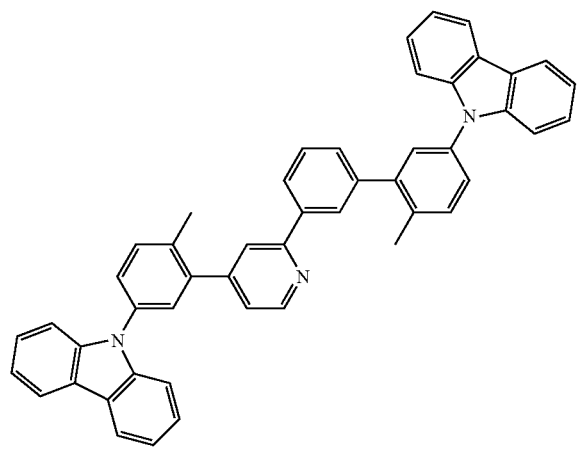
4
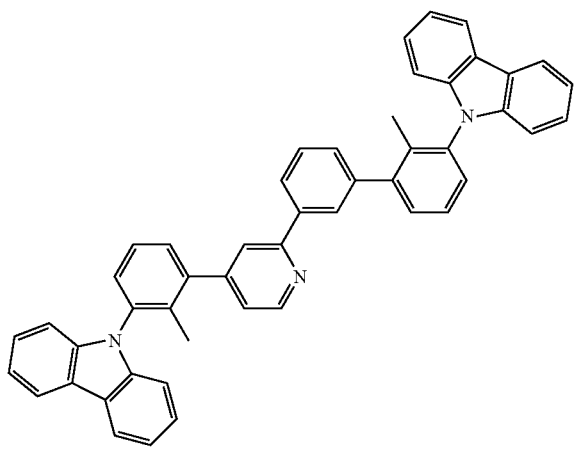
5
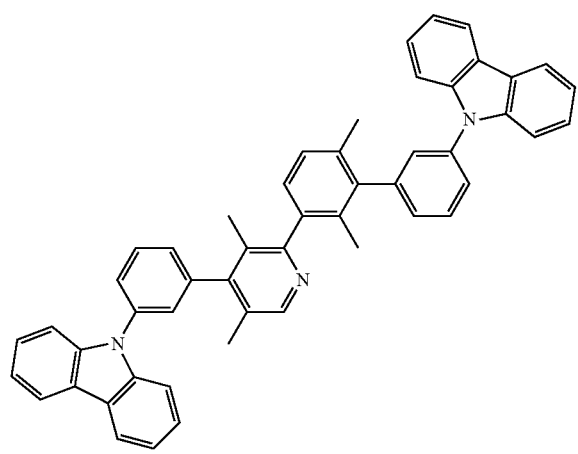
6
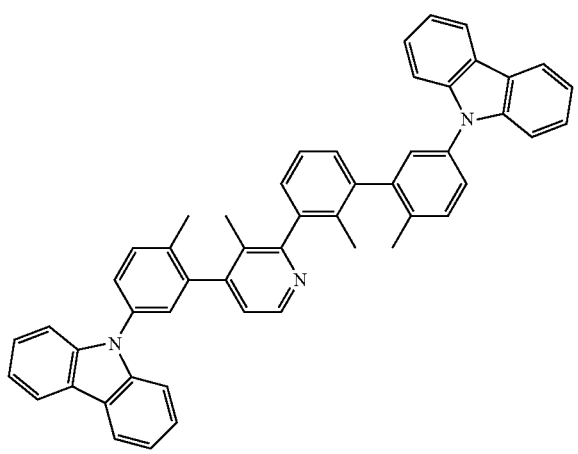
7
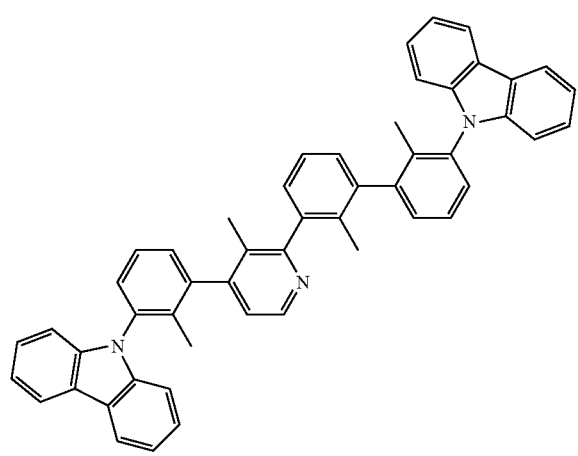
8
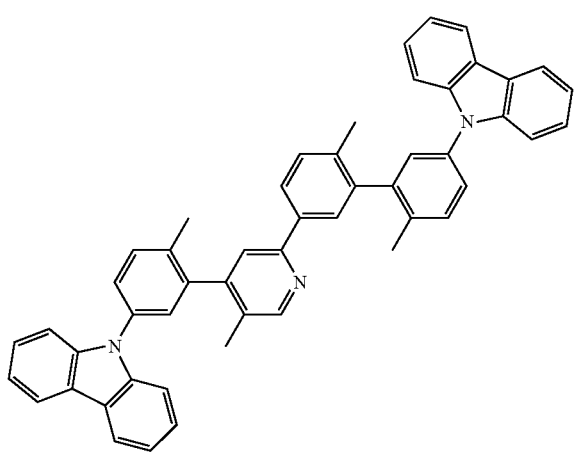

-continued
9
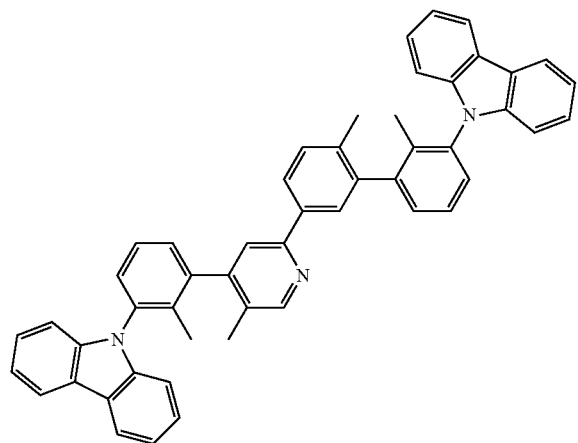
10
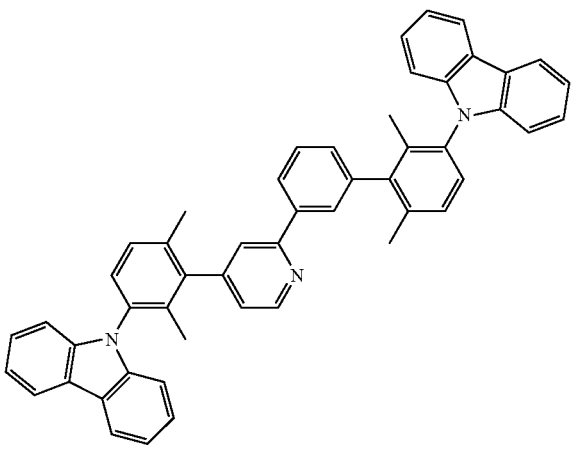
11
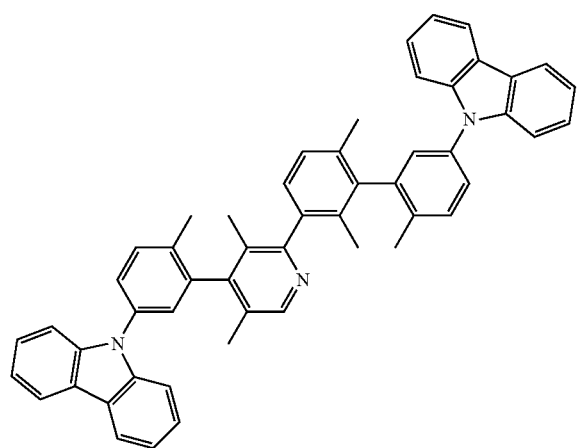
12
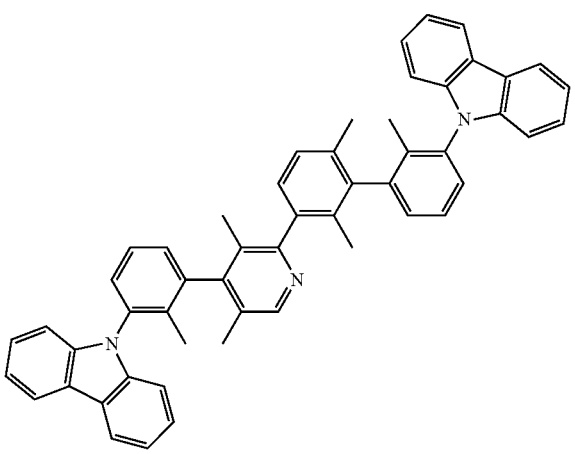
13
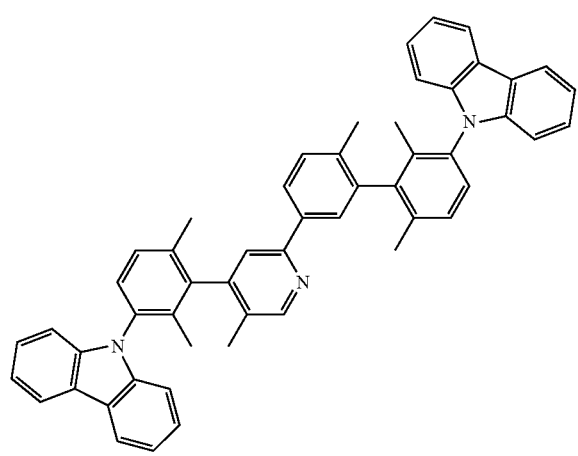
14
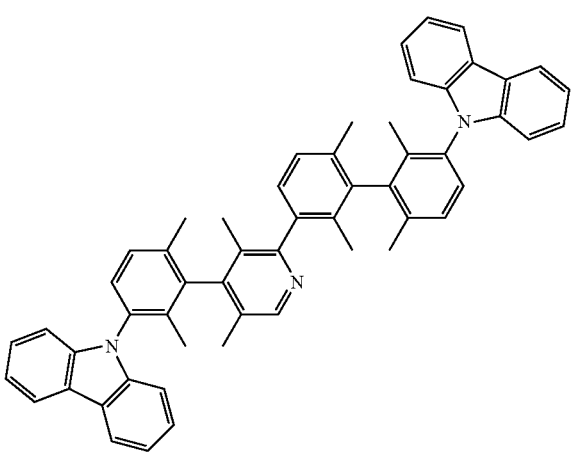

-continued
15
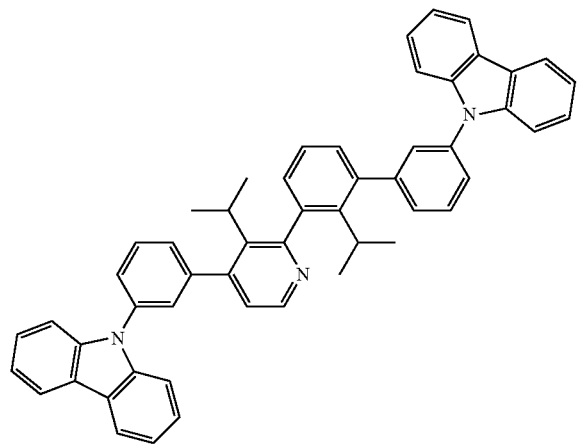
16
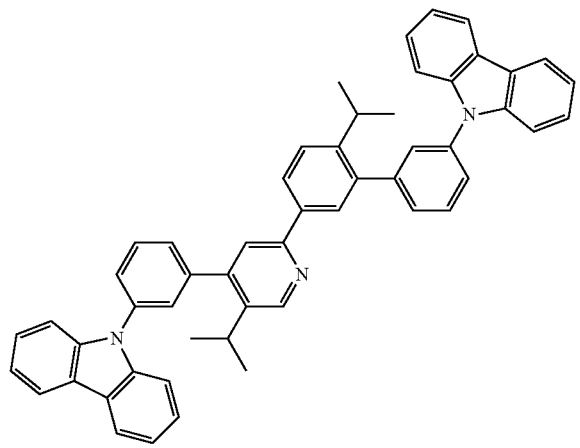
17
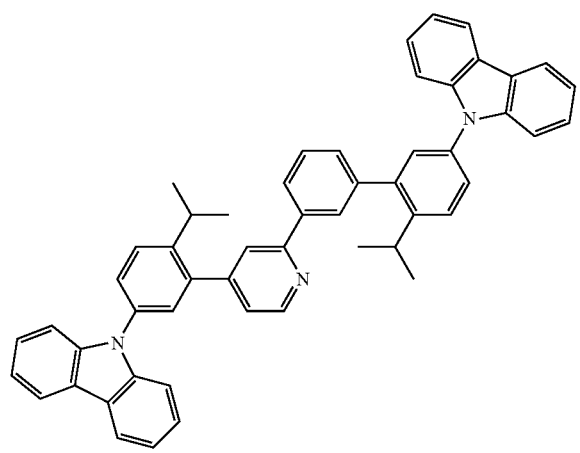
18
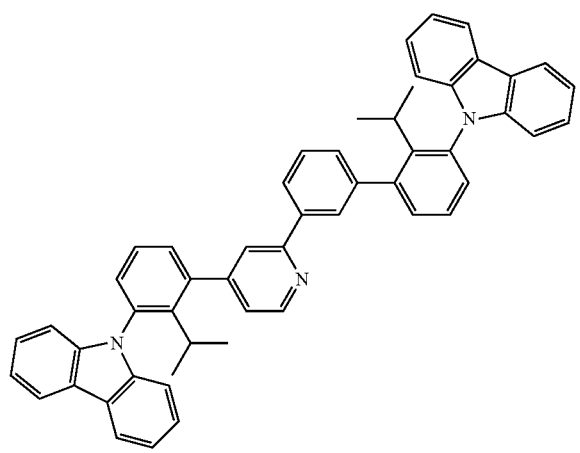
19
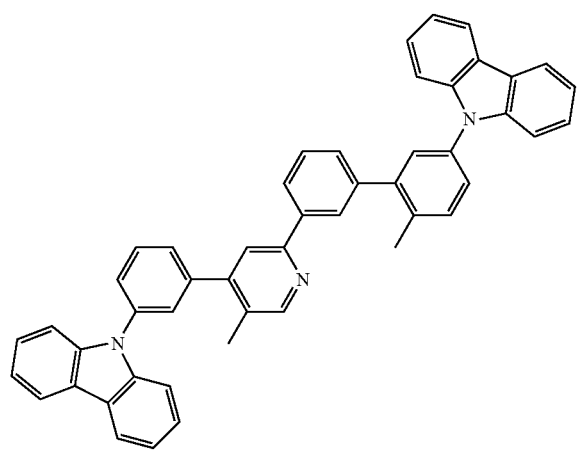
20
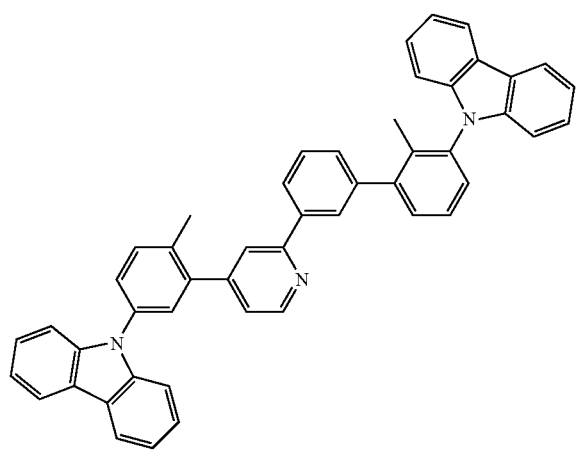

-continued
21
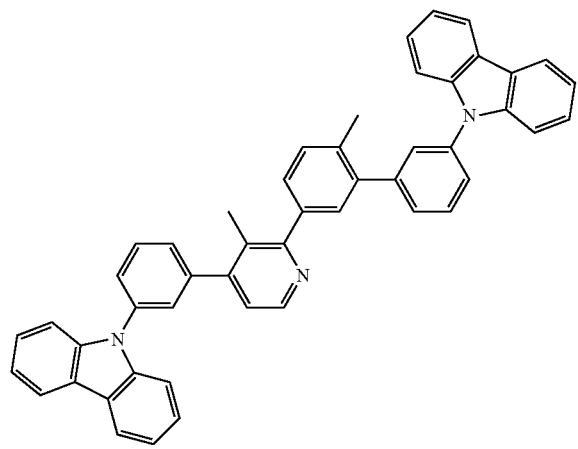
22
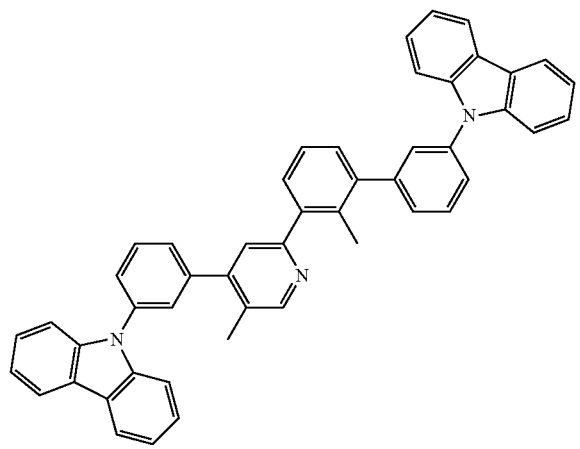
23
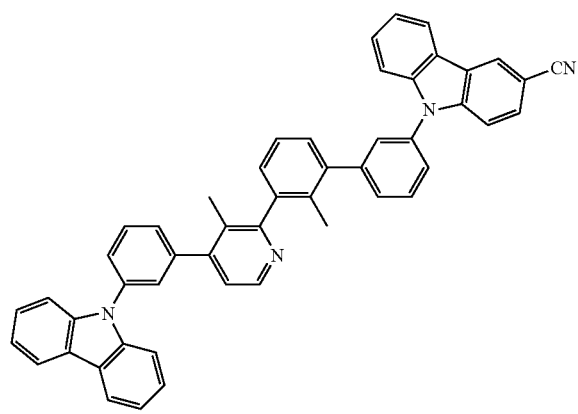
24
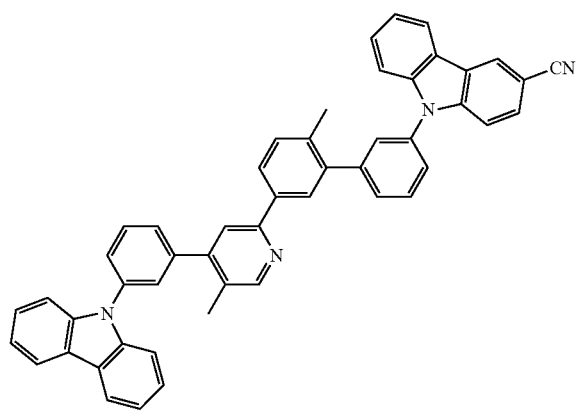
25
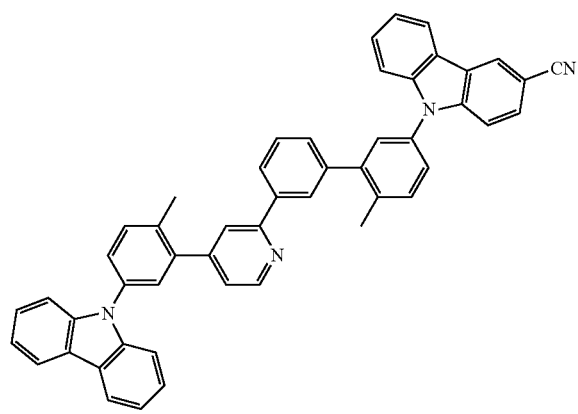
26
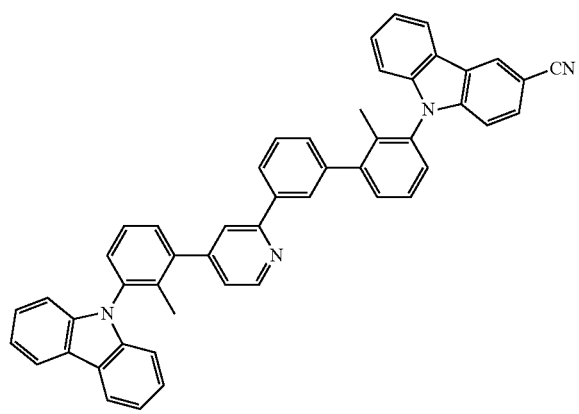

-continued
27
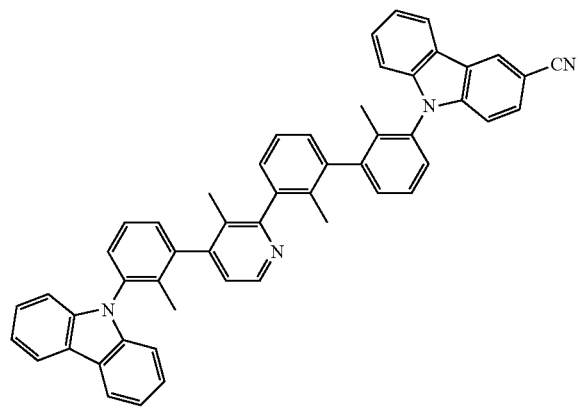
28
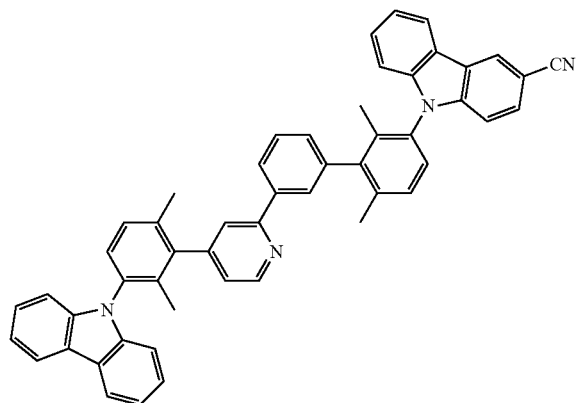
29
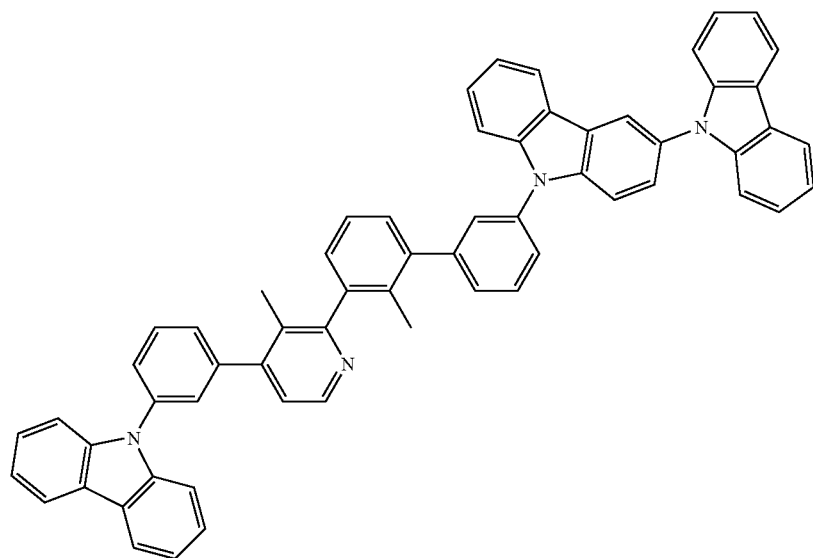
30
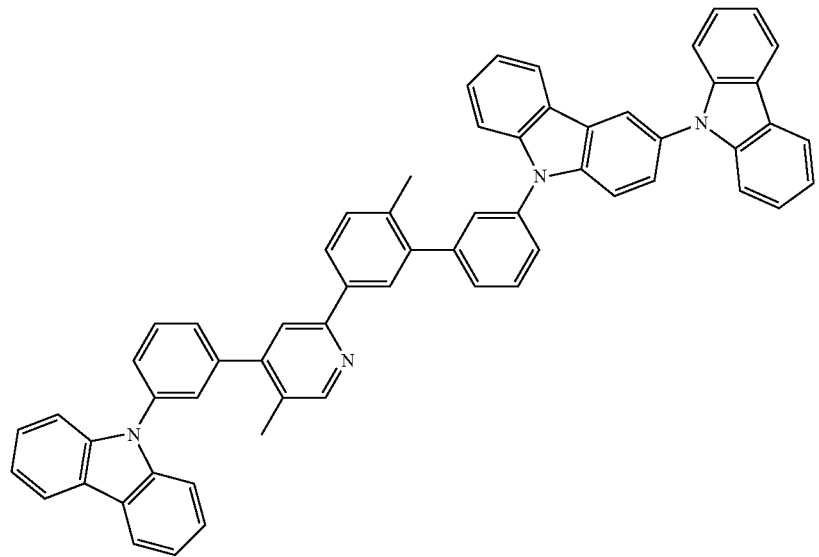

-continued
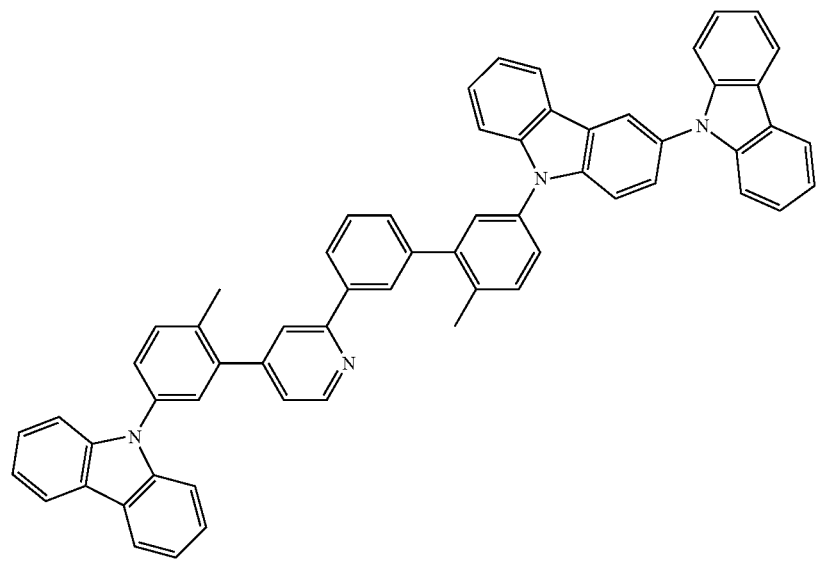
31
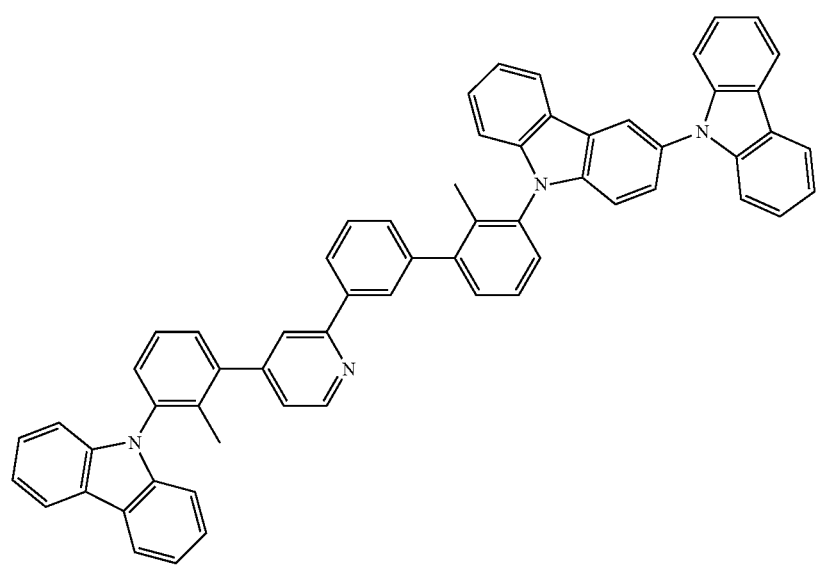
32

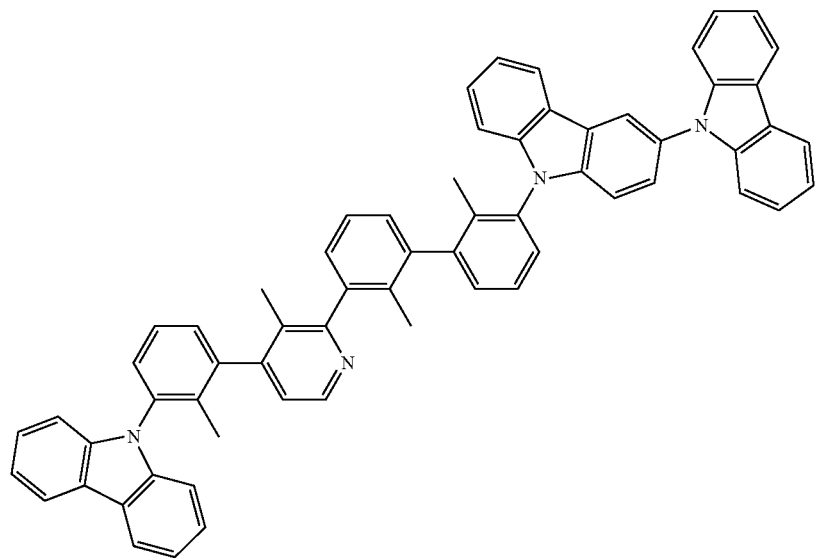
33
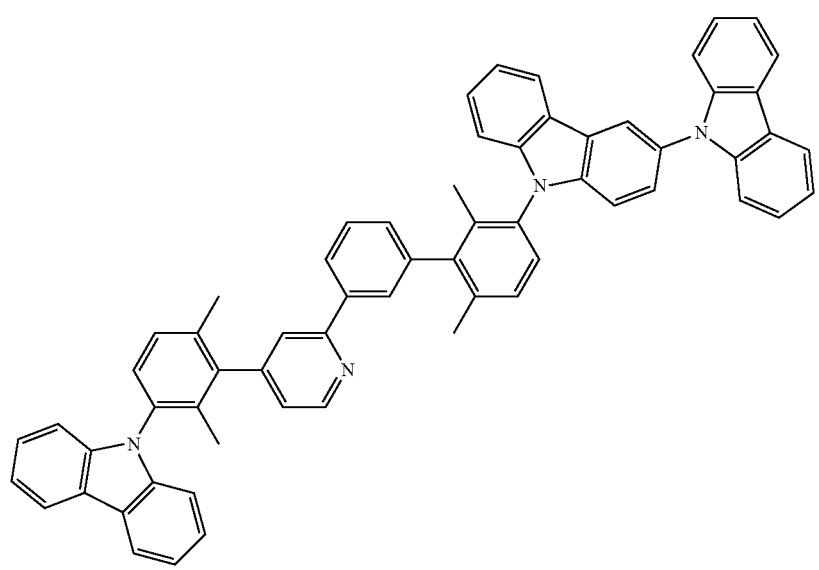
34
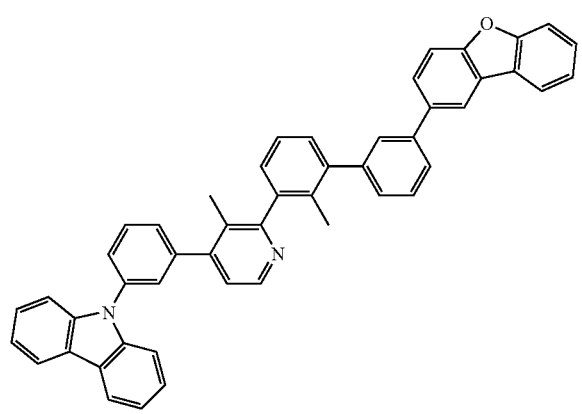
35
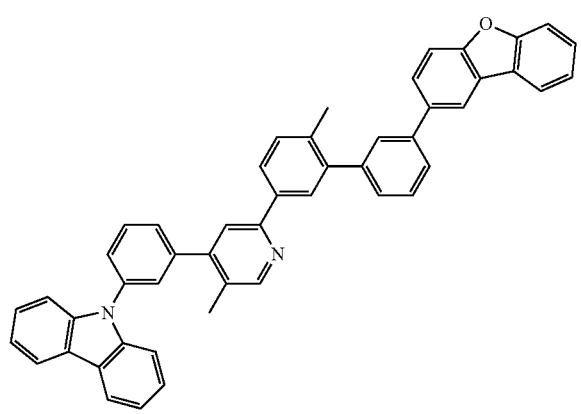
36

37

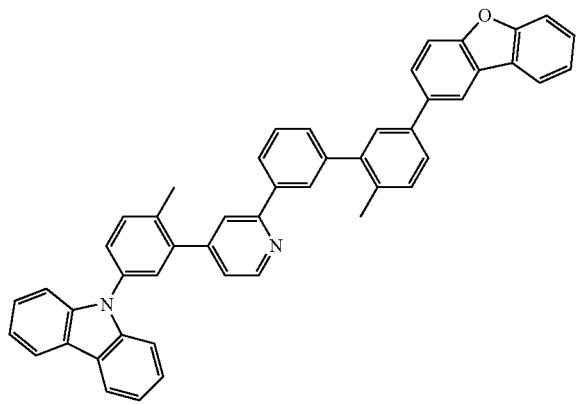

39

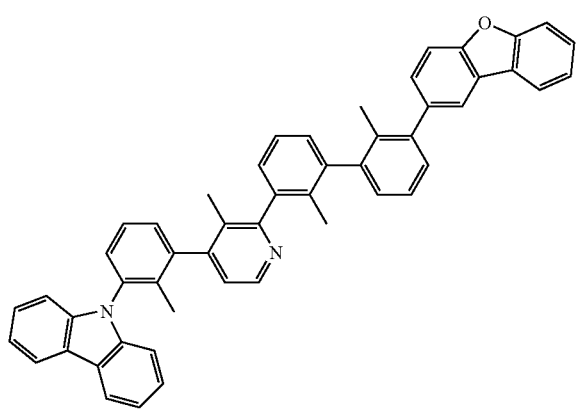

38

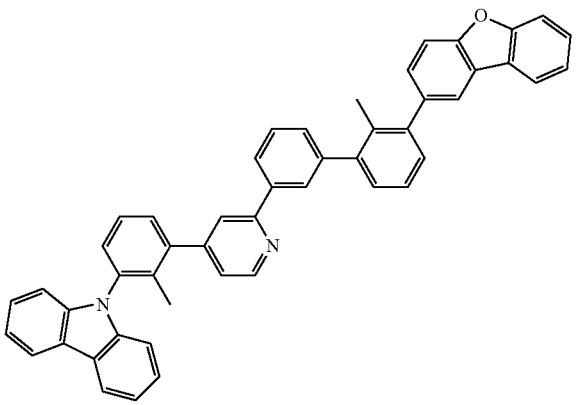

40

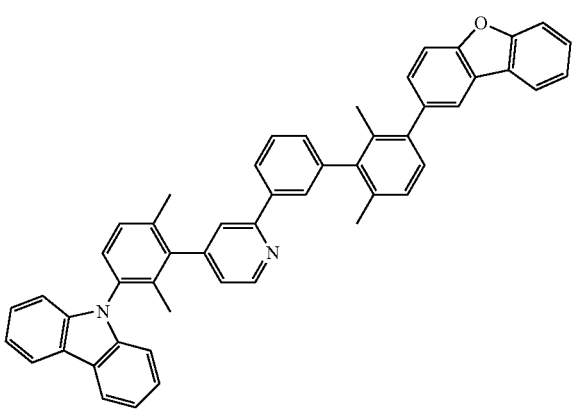

In another aspect, the present disclosure provides an organic light emitting diode, comprising: a first electrode; a second electrode facing the first electrode; and an organic emissive layer comprising a first emitting material layer disposed between the first electrode and the second electrode, wherein the first emitting material layer comprise the above organic compound.

The first emitting material layer may comprise a first host and a first dopant, and the first host may comprise the organic compound and the first dopant may comprise delayed fluorescent material.

An energy level bandgap ($|HOMO_{HOST}-HOMO_{DOPANT}|$) between a HOMO energy level ($HOMO_{HOST}$) of the first host and a HOMO energy level ($HOMO_{DOPANT}$) of the first Dopant, or an energy level bandgap ($|LUMO_{HOST}-LUMO_{DOPANT}|$) between a LUMO energy level ($LUMO_{HOST}$) of the first host and a LUMO energy level ($LUMO_{DOPANT}$) of the first dopant may be equal to or less than about 0.5 eV.

The first emitting material layer may further comprise a second dopant, and wherein an excited singlet energy level of the first dopant may be higher than an excited singlet energy level of the second dopant.

An excited triplet energy level of the first dopant may be lower than an excited triplet energy level of the first host and higher than an excited triplet energy level of the second dopant.

The organic light emitting diode may further comprise a second emitting material layer disposed between the first electrode and the second electrode, the second emitting material layer may comprise a second host and a second dopant, and the second dopant may comprise a fluorescent material.

An excited singlet energy level of the first dopant may be higher than an excited singlet energy level of the second dopant.

The organic light emitting diode may further comprise a hole blocking layer and/or an electron blocking layer disposed between the first electrode and the second electrode, and the first host may be identical to the second host.

The organic light emitting diode may further comprise a third emitting material layer disposed between the first electrode and the second electrode, the third emitting material layer may comprise a third host and a third dopant, and the third dopant may be fluorescent material.

An excited singlet energy level of the first dopant may be higher than excited singlet energy levels of the second and third dopants.

Each of an excited singlet energy level and an excited triplet energy level of the first host may be higher than each of an excited singlet energy level and an excited triplet energy level of the first dopant, respectively, an excited singlet energy level of the second host may be higher than an excited singlet energy level of the second dopant, and an excited singlet energy level of the third host may be higher than an excited singlet energy level of the third dopant.

The organic emissive layer may further comprise a hole injection layer, a hole transport layer and an electron blocking layer each of which is disposed between the first electrode and the first emitting material layer, and an electron injection layer, an electron transport layer and a hole blocking layer each of which is disposed between the second electrode and the first emitting material layer, and the organic compound may be a first host in the first emitting material layer.

In still another aspect, the present disclosure provides an organic light emitting device that comprises a substrate and the above-mentioned organic light emitting diode over the substrate.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain principles of the disclosure.

DETAILED DESCRIPTION

Reference will now be made in detail to aspects of the disclosure, examples of which are illustrated in the accompanying drawings.

Figure 1:
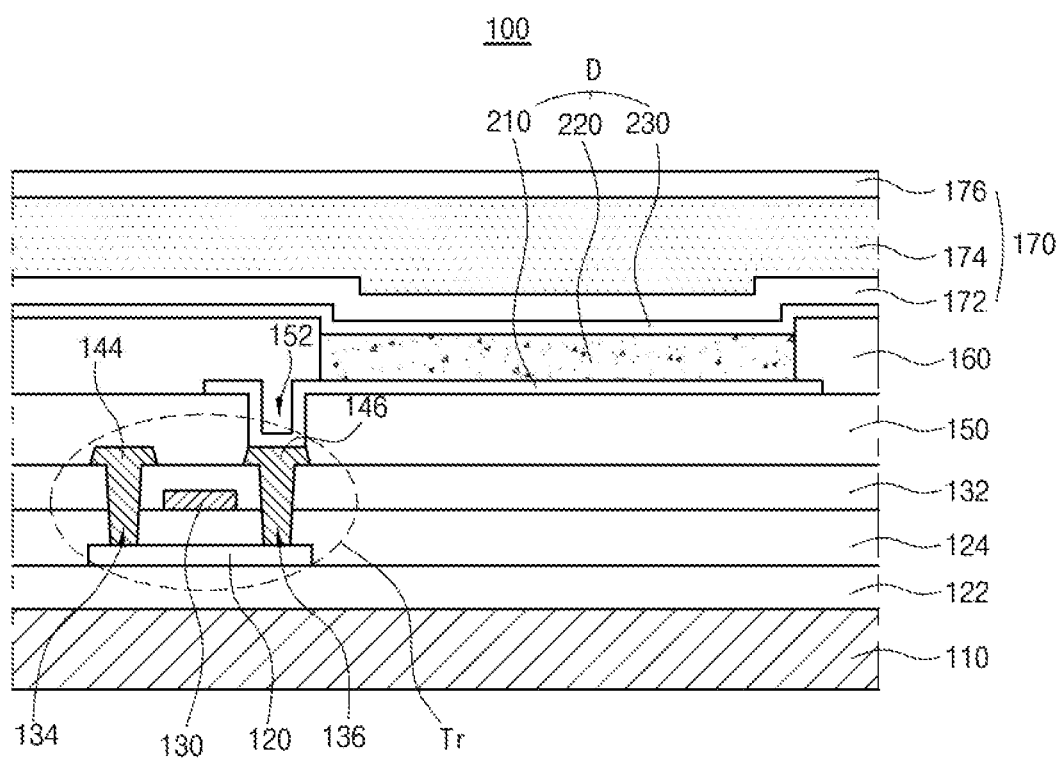
FIG. 1 is a schematic cross-sectional view illustrating an organic light emitting display device of the present disclosure.

FIG. 1 is a schematic cross-sectional view illustrating an organic light emitting display device t of the present disclosure as an example of an organic light emitting device. As illustrated in FIG. 1, the organic light emitting display device 100 includes a substrate 110, a thin-film transistor Tr on the substrate 110, and an organic light emitting diode D connected to the thin film transistor Tr.

The substrate 110 may include, but is not limited to, a glass substrate or a plastic substrate. For example, the substrate 110 may be made of, but is not limited to, polyimide (PI). A buffer layer 122 can be disposed over the substrate 110, and the thin film transistor Tr is disposed over the buffer layer 122. The buffer layer 122 can be omitted.

A semiconductor layer 120 is disposed over the buffer layer 122. The semiconductor layer 120 may be made of, but is not limited to, oxide semiconductor materials or polycrystalline silicon. When the semiconductor layer 120 is made of oxide semiconductor materials, a light-shield pattern can be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 may be made of polycrystalline silicon. In this case, opposite edges of the semiconductor layer 120 can be doped with impurities.

A gate insulating layer 124 formed of an insulating material is disposed on the semiconductor layer 120. The gate insulating layer 124 may be made of, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 can be patterned identically as the gate electrode 130.

An interlayer insulating layer 132 formed of an insulating material is disposed on the gate electrode 130 with covering over an entire surface of the substrate 110. The interlayer insulating layer 132 may be made of, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 1. Alternatively, the first and second semiconductor layer contact holes 134 and 136 are formed only within the interlayer insulating layer 132 when the gate insulating layer 122 is patterned identically as the gate electrode 130.

A source electrode 144 and a drain electrode 146, which are formed of a conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr may have an inverted staggered structure in which a gate electrode is disposed under a semiconductor layer and a source and drain electrodes are disposed over the semiconductor layer. In this case, the semiconductor layer may be made of amorphous silicon.

In FIG. 1, a gate line and a data line, which cross each other to define a pixel region, and a switching element, which is connected to the gate line and the data line, can be further formed in the pixel region. The switching element is connected to the thin film transistor Tr, which is a driving element. Besides, a power line is spaced apart in parallel from the gate line or the data line, and the thin film transistor Tr can further include a storage capacitor configured to constantly keep a voltage of the gate electrode for one frame.

A passivation layer 150 is disposed on the thin film transistor Tr over the whole substrate 110. The passivation layer 150 has a drain contact hole 152 that exposes the drain electrode 146 of the thin film transistor Tr.

The organic light emitting diode D includes a first electrode 210 that is disposed on the passivation layer 150 and connected to the drain electrode 146 of the thin film transistor Tr through the drain contact hole 152. The first electrode 210 is disposed in each pixel region. The first electrode 210 may be an anode and may be made of conductive materials having a relatively high work function value. For example, the first electrode 210 may be made of, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

When the organic light emitting display device 100 is a top-emission type, a reflective electrode or a reflective layer can be disposed under the first electrode 210. For example, the reflective electrode or the reflective layer may be made of, but is not limited to, aluminum-palladium-copper (APC) alloy.

In addition, a bank layer 160 is disposed on the passivation layer 150 in order to cover edges of the first electrode 210. The bank layer 160 exposes a center of the first electrode 210.

An organic emissive layer 220 is disposed on the first electrode 210. The organic emissive layer 220 may have a mono-layered structure of an emitting material layer (EML) that includes luminescent materials. Alternatively, the organic emissive layer 220 may have a multi-layered structure in order to increase its luminous efficiency.

Figure 2:
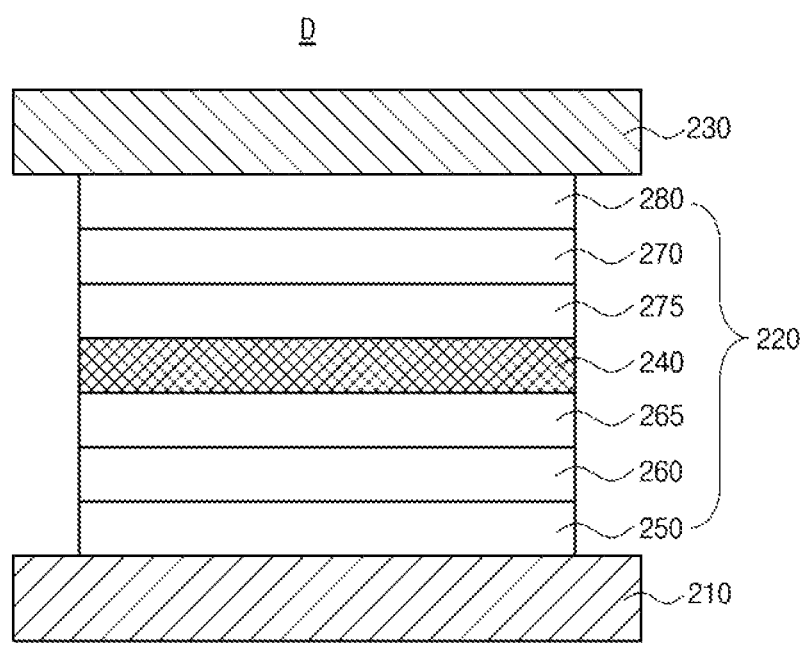
FIG. 2 is a schematic cross-sectional view illustrating an organic light emitting diode in accordance with an exemplary aspect of the present disclosure.

For example, as shown in FIG. 2, which is a cross-sectional view of an organic light emitting diode in accordance with an exemplary aspect of the present disclosure, the organic emissive layer 220 may comprise an emitting material layer (EML) 240 disposed between the first and second electrodes 210 and 230, a hole transport layer (HTL) 260 disposed between the first electrode 210 and the EML 240 and an electron transport layer (ETL) 270 disposed between the second electrode 230 and the EML 240. In addition, the organic emissive layer 220 may further comprise a hole injection layer (HIL) 250 disposed between the first electrode 210 and the HTL 260 and an electron injection layer (EIL) 280 disposed between the second electrode 230 and the ETL 270. Alternatively, the organic emissive layer 220 may further comprise an electron blocking layer (EBL) 265 disposed between the HTL 260 and the EML 240 and/or a hole blocking layer (HBL) 275 disposed between the EML 240 and the ETL 270.

The second electrode 230 is disposed over the substrate 110 above which the organic emissive layer 220 is disposed. The second electrode 230 can be disposed over a whole display area and may be made of conductive materials with a relatively low work function value compared to the first electrode 210. The second electrode 230 may be a cathode. For example, the second electrode 230 may be made of, but is not limited to, aluminum (Al), magnesium (Mg), calcium (Ca), silver (Ag), alloy thereof or combination thereof such as aluminum-magnesium alloy (Al—Mg). The first electrode 210, the organic emissive layer 220 and the second electrode 230 constitute the organic light emitting diode D.

In addition, an encapsulation film 170 may be disposed over the second electrode 230 in order to prevent outer moisture from penetrating into the organic light emitting diode D. The encapsulation film 170 may have, but is not limited to, a laminated structure of a first inorganic insulating film 172, an organic insulating film 174 and a second inorganic insulating film 176.

Also, a polarizer may be attached to the encapsulation film 170 in order to decrease external light reflection. For example, the polarizer may be a circular polarizer. In addition, a cover window may be attached to the encapsulation film 170 or the polarizer. In this case, the substrate 110 and the cover window may have a flexible property, thus the organic light emitting display device 100 may be a flexible display device.

Alternatively, the organic light emitting display device 100 may include a color filter that comprises dyes or a pigments for transmitting specific wavelength light of light emitted from the organic light emitting diode D. For example, the color filter can transmit light of specific wavelength such as red (R), green (G), blue (B) and/or white (W). Each of red, green and blue color filters may be formed separately in each pixel region and each color filter pattern may be disposed to overlap each other with the organic emissive layer 220 in the OLED D emitting light. In this case, the organic light emitting display device 100 can implement full-color through the color filter.

For example, when the organic light emitting display device 100 is a bottom-emission type, the color filter can be disposed on the interlayer insulating layer 132 with corresponding to the OLED D. Alternatively, when the organic light emitting display device 100 is a top-emission type, the color filter can be disposed over the OLED D, that is, a second electrode 230.

The organic emissive layer 220 comprises an organic compound having the following structure of Chemical Formula 1:

[Chemical Formula 1]

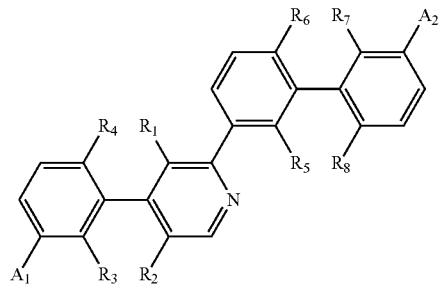

In Chemical Formula 1, each of $R_1$ to $R_8$ is independently protium, deuterium, tritium, $C_1$-$C_{10}$ alkyl, $C_6$-$C_{30}$ aryl or $C_3$-$C_{30}$ hetero aryl; and each of $A_1$ and $A_2$ is independently protium, deuterium, tritium, or an unsubstituted or substituted hetero aromatic group having one to three hetero aromatic moieties.

As an example, at least one of $R_1$ to $R_4$ is selected from the group consisting of $C_1$-$C_{10}$ alkyl, $C_6$-$C_{30}$ aryl and $C_3$-$C_{30}$ hetero aryl and at least one of $R_5$ to $R_8$ is selected from the group consisting of $C_1$-$C_{10}$ alkyl, $C_6$-$C_{30}$ aryl. Each of $A_1$ and $A_2$ may be independently selected from the group consisting of unsubstituted or substituted carbazolyl, unsubstituted or substituted dibenzofuryl and unsubstituted or substituted dibenzothiophenyl. $A_1$ and/or $A_2$ may be further substituted with —CN, the carbazolyl may be unsubstituted or further substituted with carbazolyl, phenyl and combination thereof. For example, each of $A_1$ and $A_2$ may be independently selected from the following Chemical Formula 2:

[Chemical Formula 2]

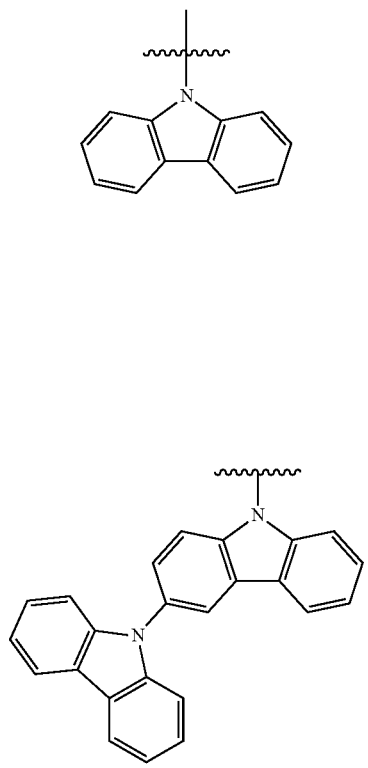

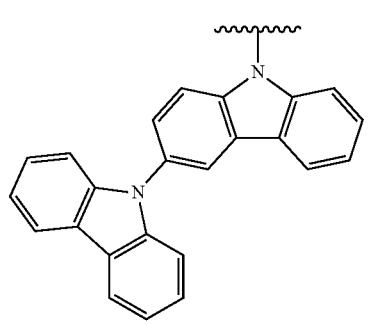

-continued

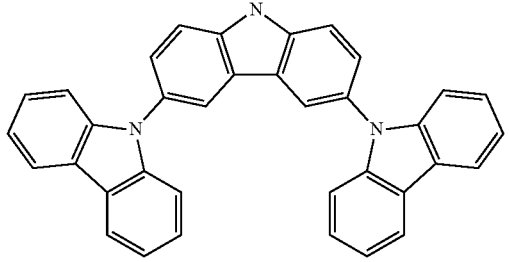

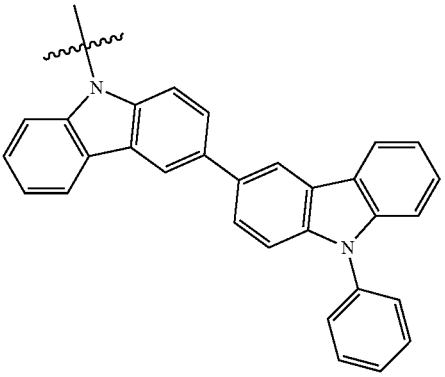

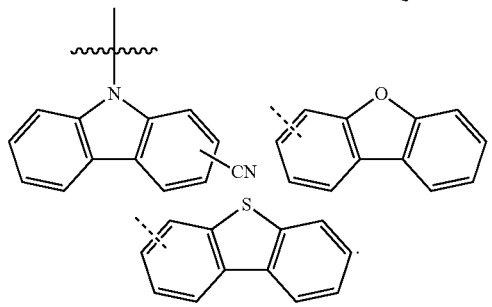

For example, the organic compound having the structure of Chemical Formula 1 may be any one of the following Chemical Formula 3:

[Chemical Formula 3]

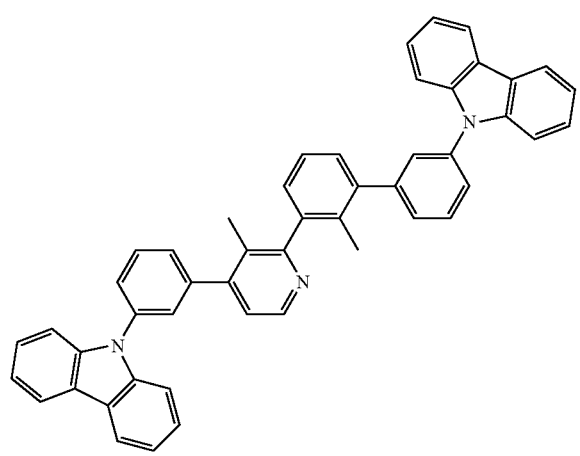

1

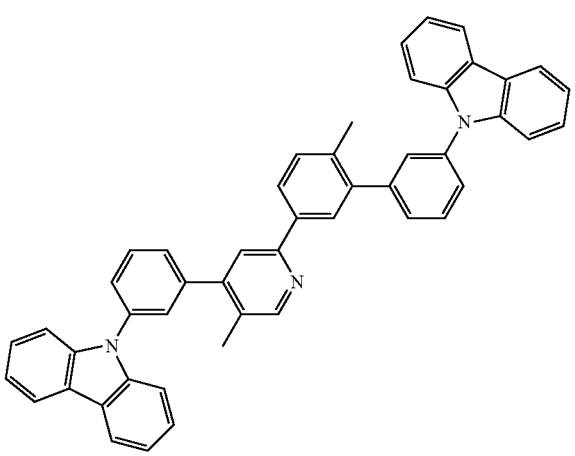

2

-continued
3
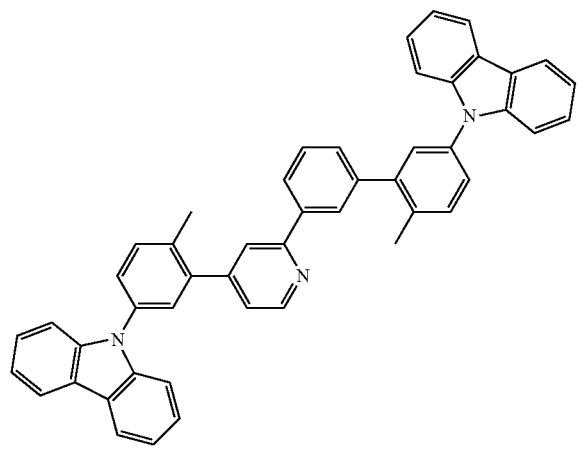
4
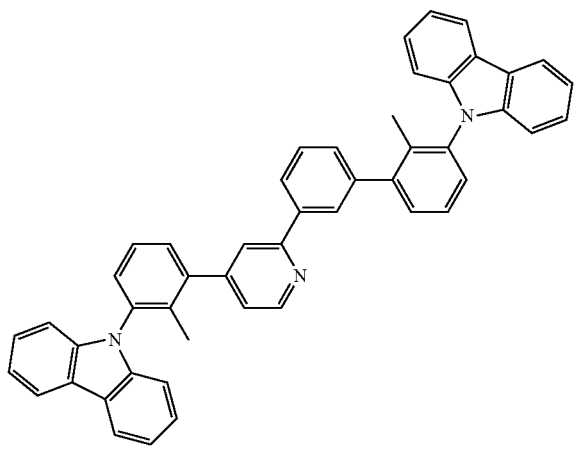
5
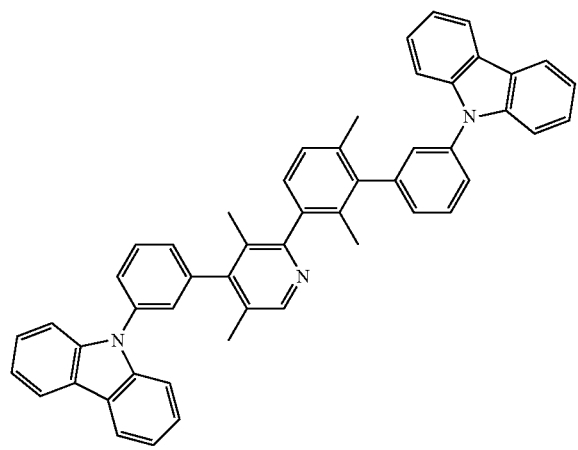
6
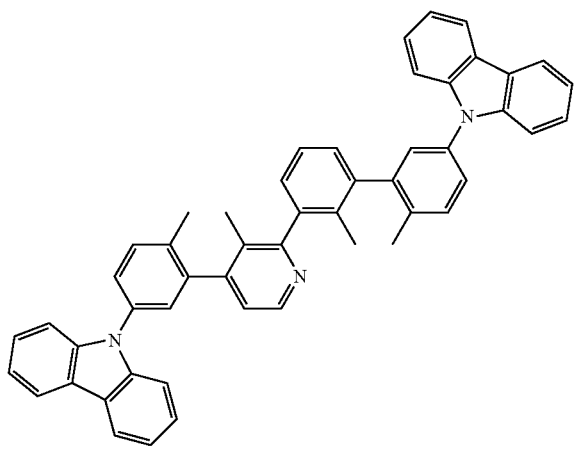
7
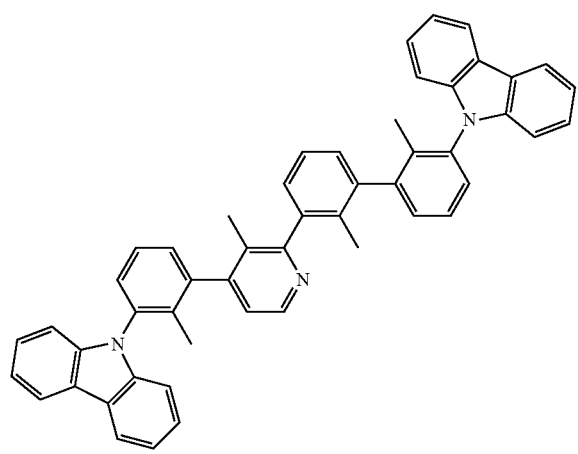
8
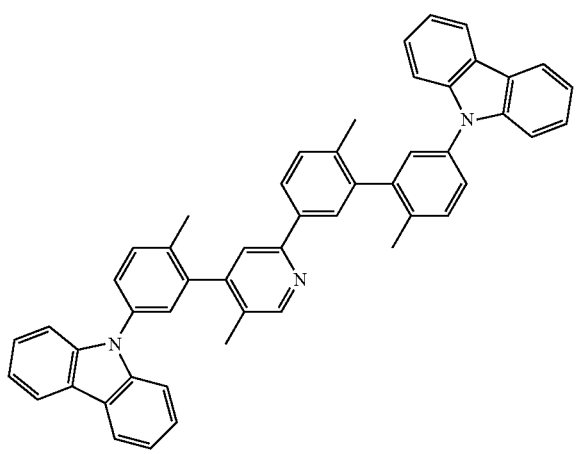

-continued
9
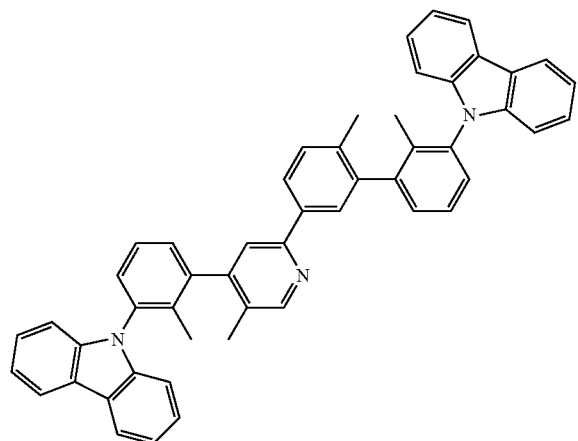
10
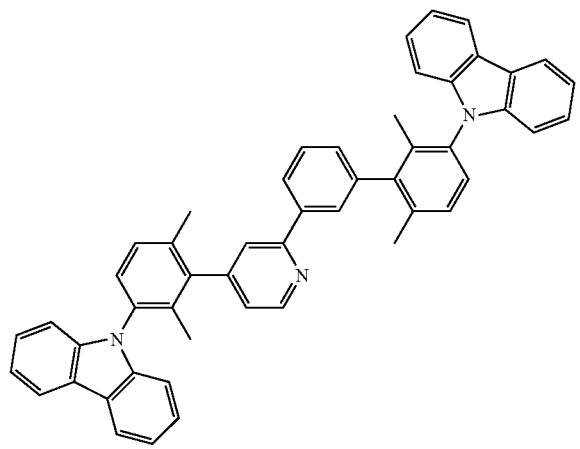
11
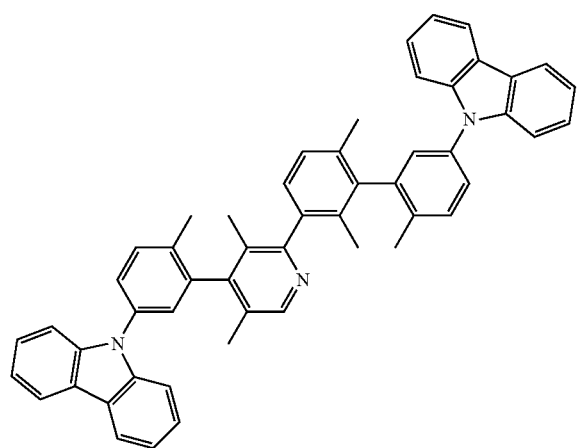
12
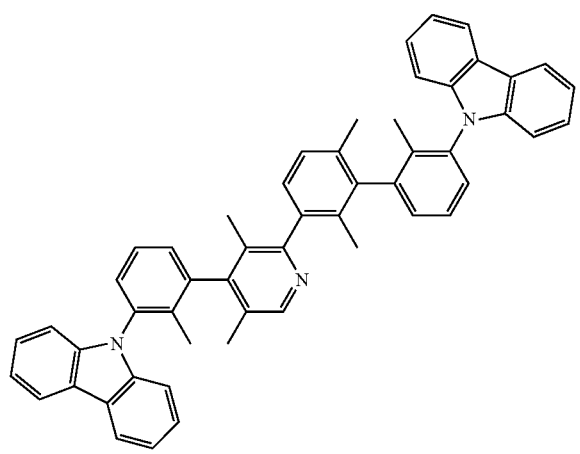
13
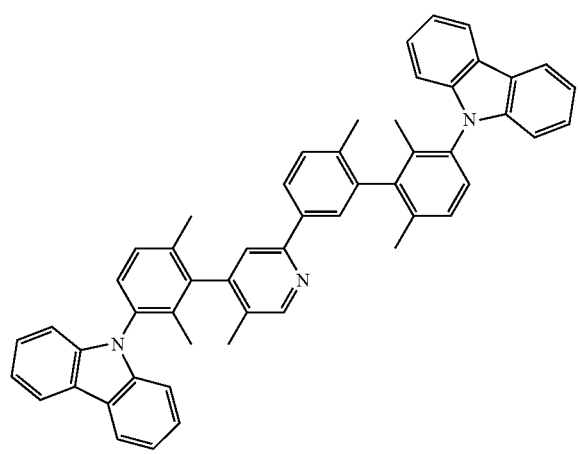
14
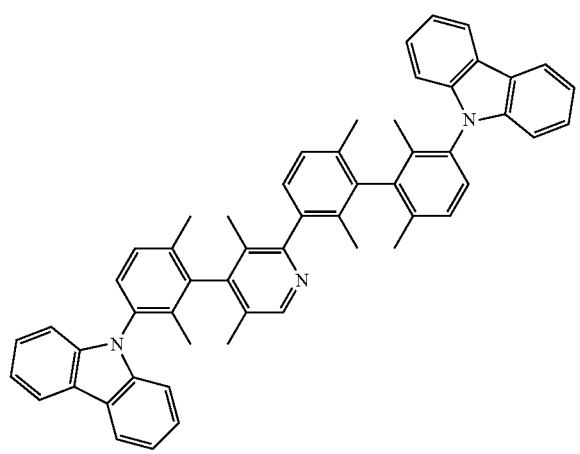

-continued
15
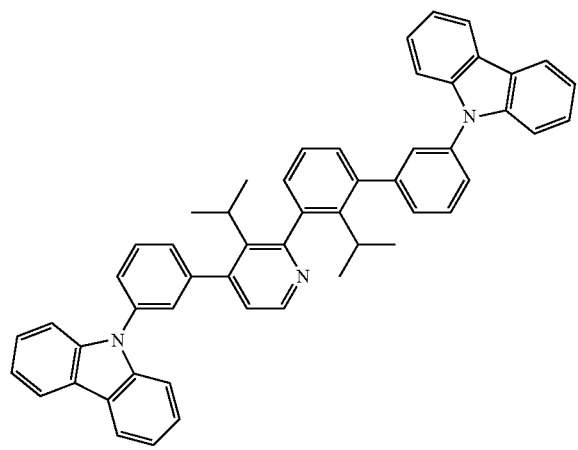
16
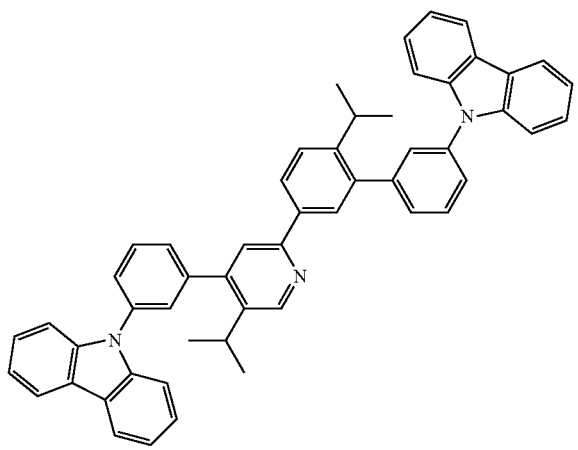
17
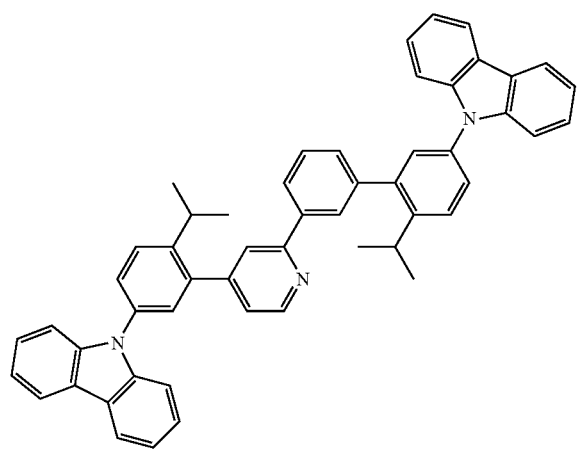
18
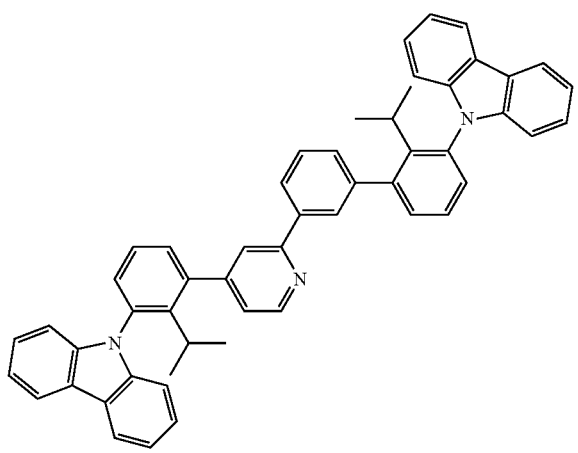
19
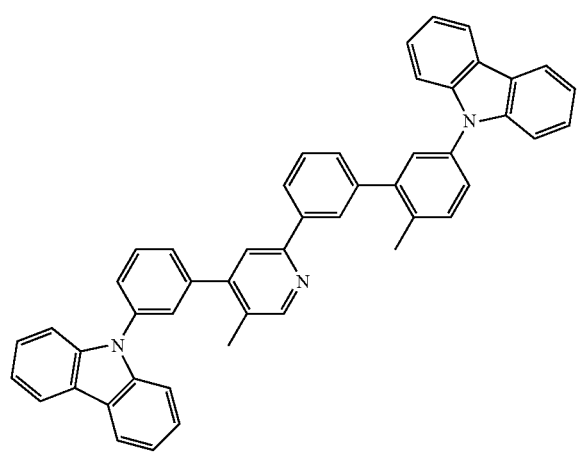
20
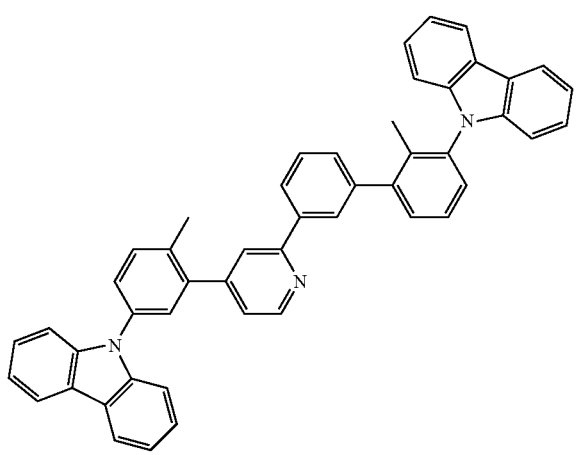

-continued
21
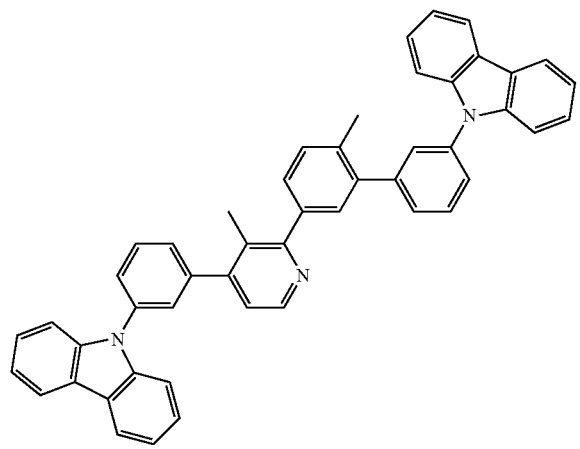
22
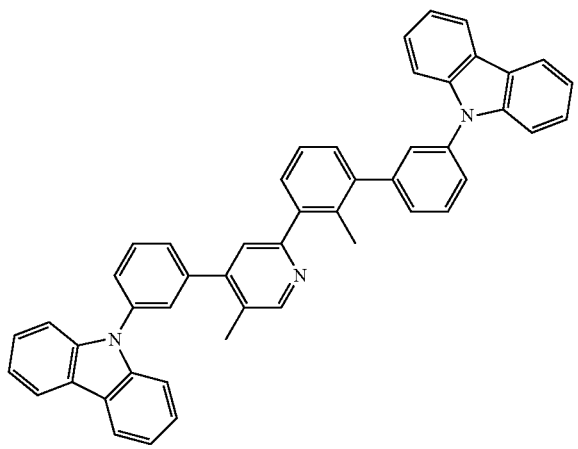
23
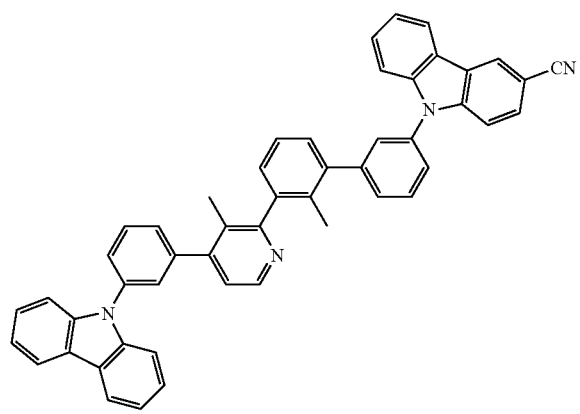
24
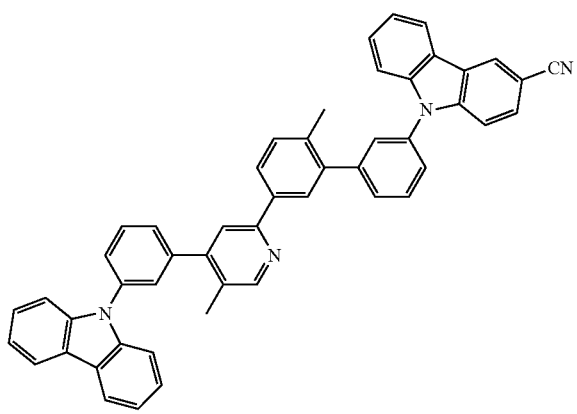
25
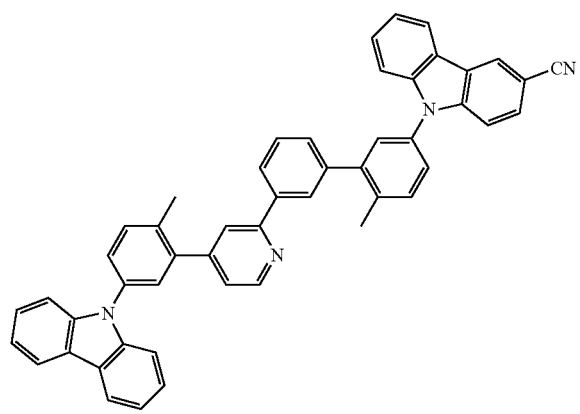
26
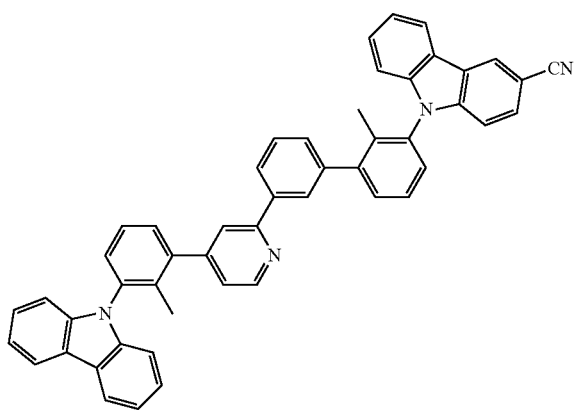

-continued
27
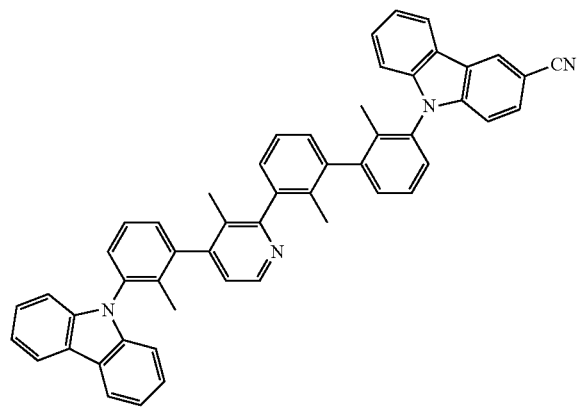
28
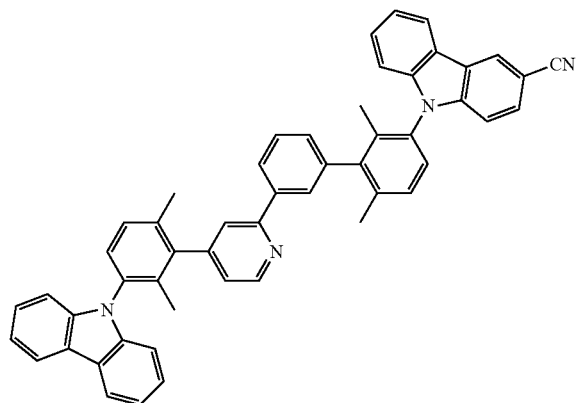
29
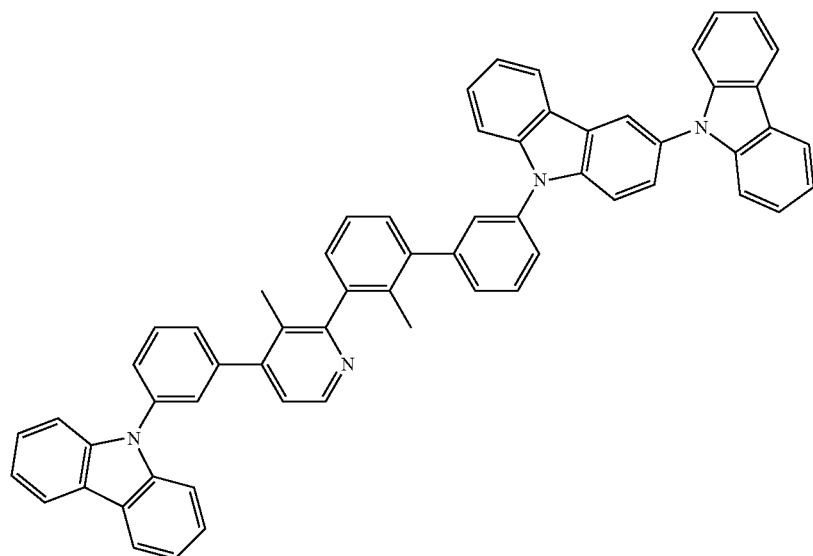
30
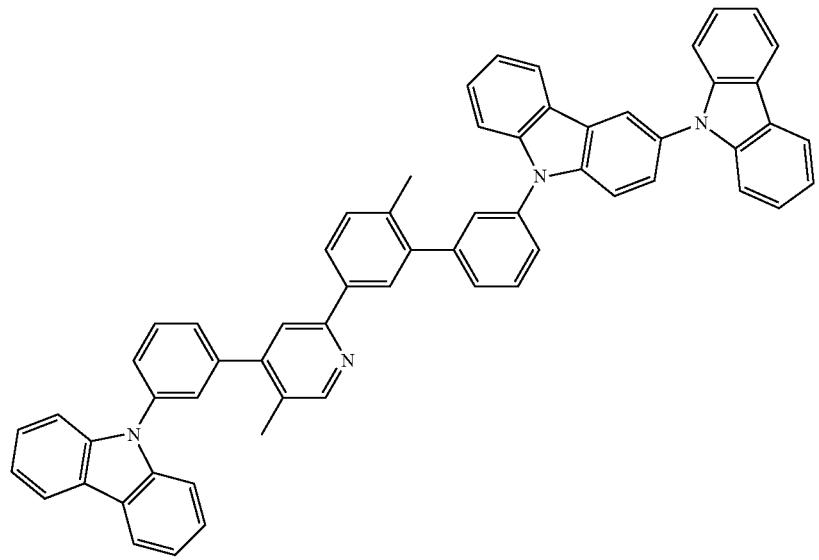

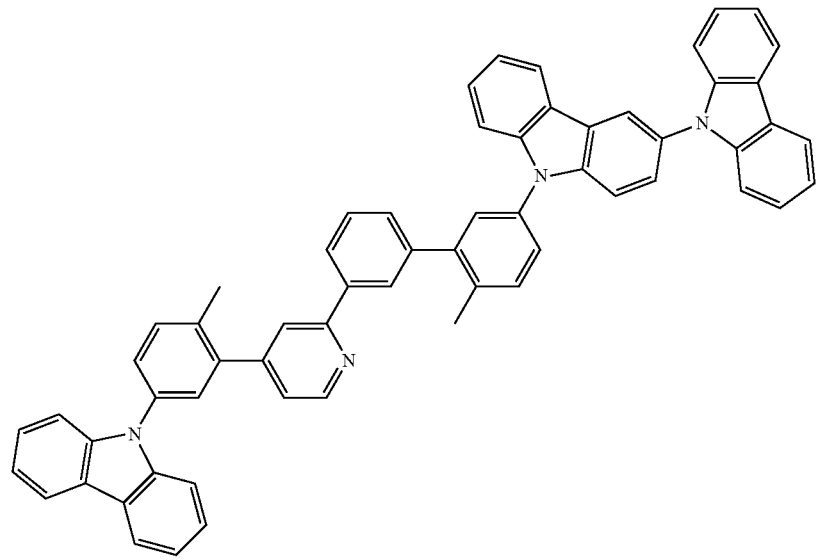
31
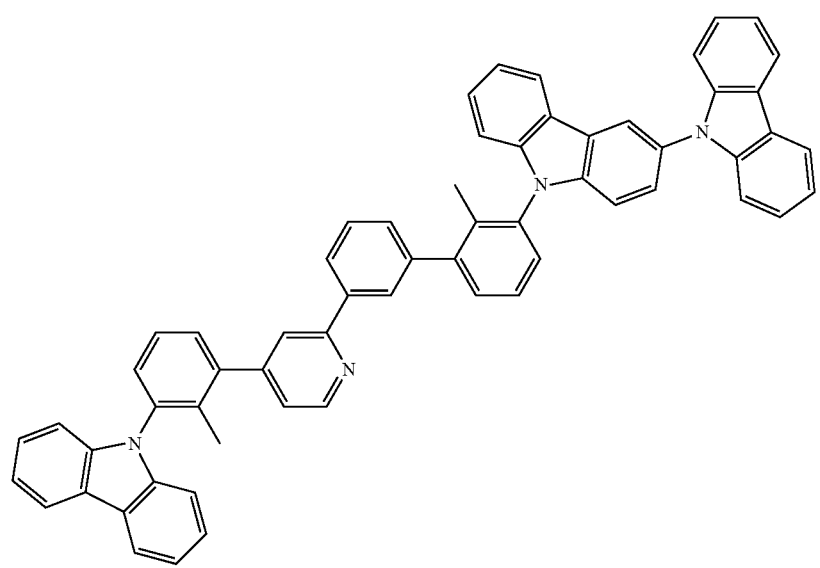
32

-continued
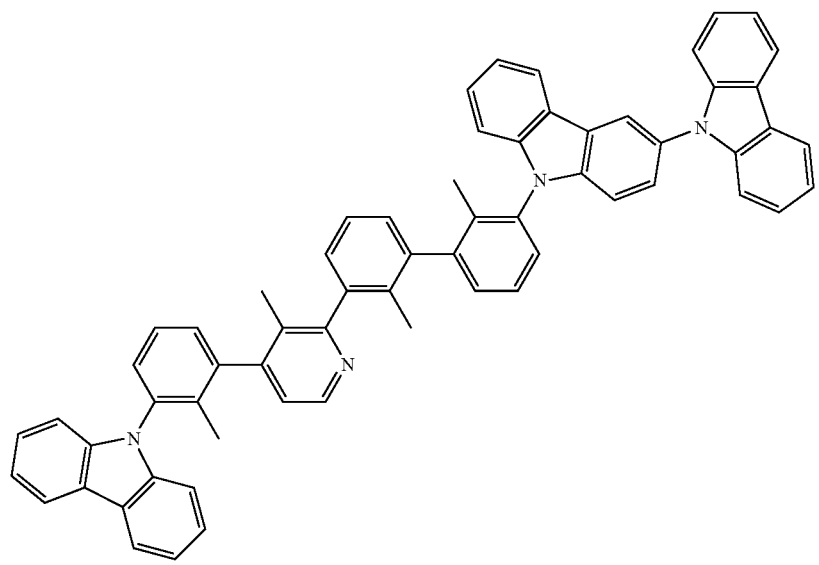
33
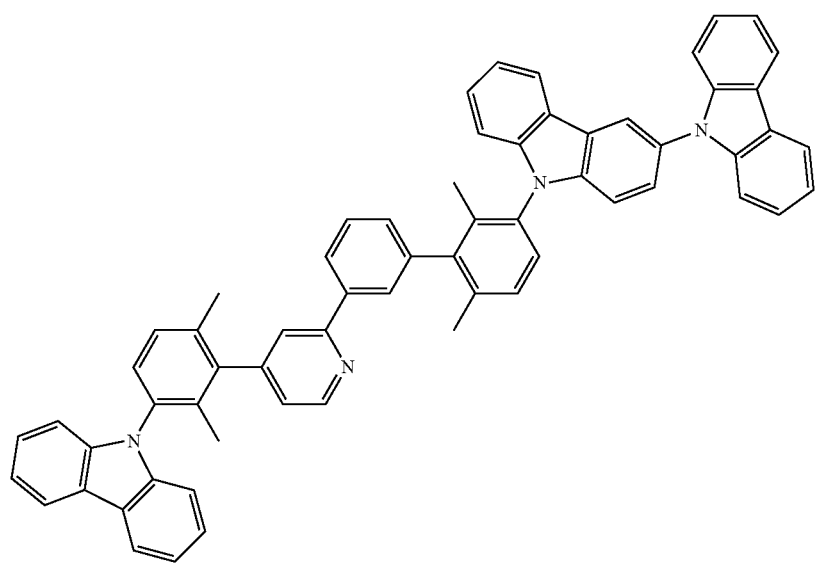
34
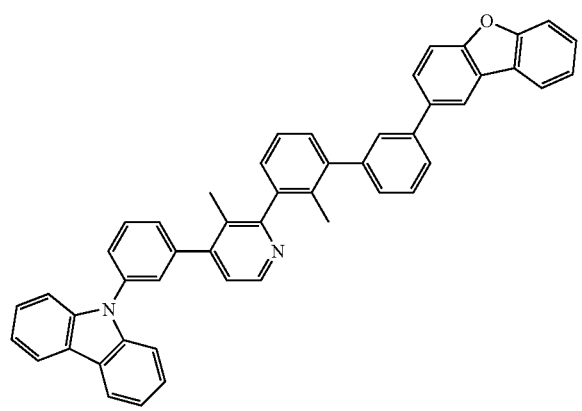
35
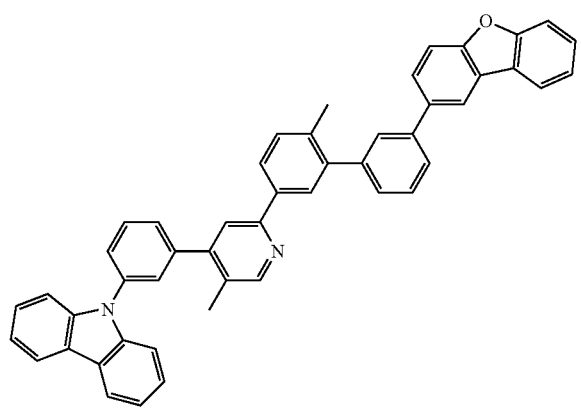
36

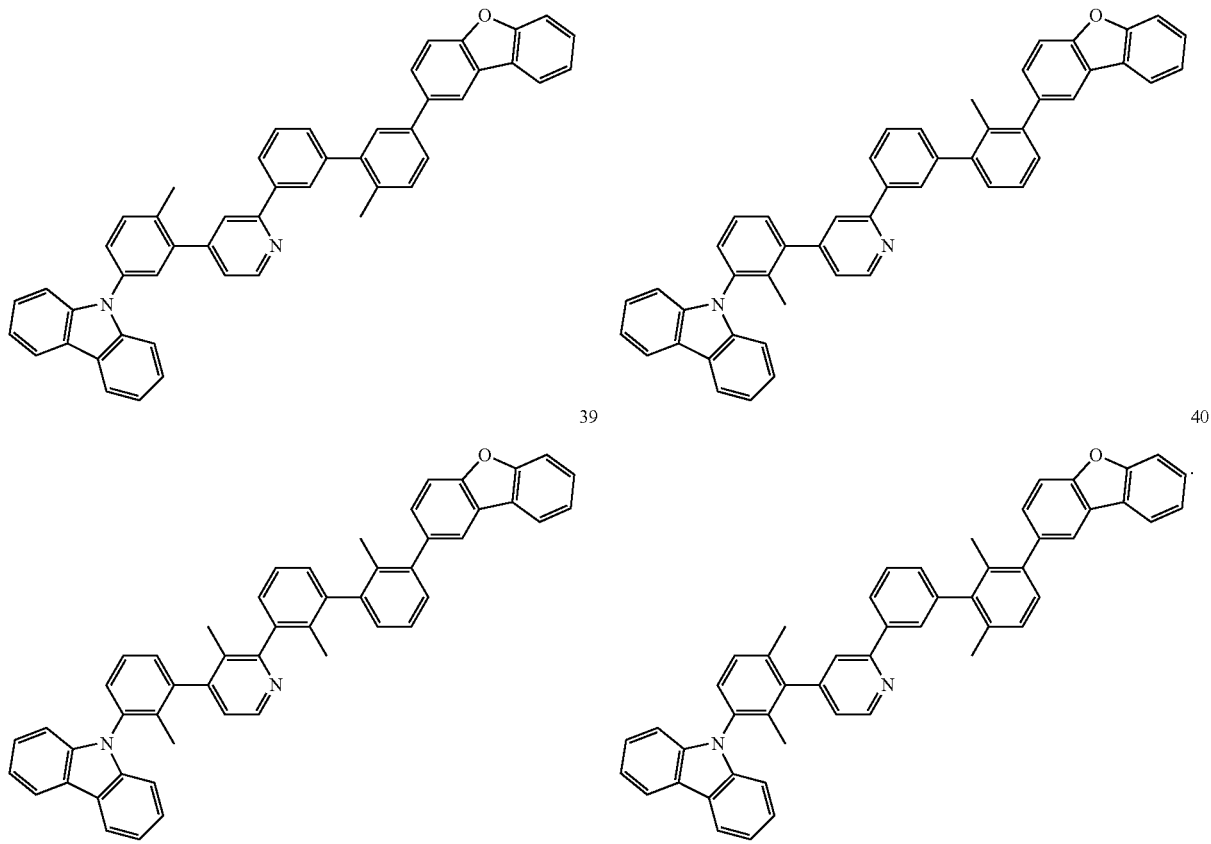

As an example, the organic compound of the present disclosure may be used as an n-type host (first host) in the organic emissive layer 220. The organic compound of the present disclosure contains a pyridine moiety that is located inner side of a molecular core, and thereby preventing energy level bandgap from being reduced. Also, it is possible to prevent an excited triplet energy level $T_1^H$ (see, FIG. 6) of the organic compound being decreased owing to introducing n-type property by substituting at least one of $R_1$ to $R_8$ with alkyl, aryl and/or hetero aryl.

In general, an n-type organic compound has relatively low excited triplet energy level and its excited triplet energy level is not raised even though the n-type organic compound contains a carbazolyl moiety, a dibenzofuryl moiety and/or a dibenzothiophenyl moiety, each of which is introduced for raising the excited triplet energy level of the organic compound. On the other hand, since each of the phenyl ring, the pyridine ring and the donor group ($A_1$ and $A_2$, ex. the carbazolyl moiety, the dibenzofuryl moiety and/or the dibenzothiophenyl moiety) in the organic compound of the present disclosure is linked at a -meta position, the organic compound can exhibit higher excited triplet energy level. Accordingly, when the organic compound of the present disclosure is used the host in the EML 240, both the organic light emitting diode D and the organic light emitting display device 100 can enhance their luminous efficiency and luminous lifetime.

Figure 3:
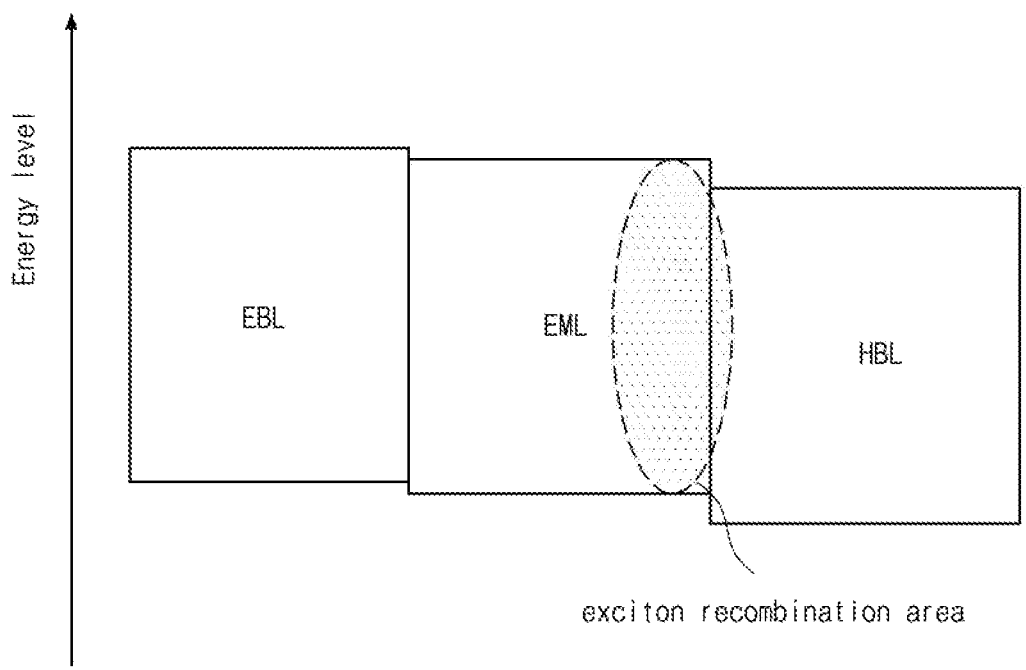
FIG. 3 is a schematic diagram illustrating an exciton recombination area using a conventional p-type host in an emitting material layer.

Referring to FIG. 3, which is a schematic diagram illustrating an exciton recombination area using a conventional p-type host in an emitting material layer (EML), since holes transport faster than electrons into the EML owing the p-type host in the EML in a structure sequentially laminated EBL, EML and HBL, the exciton recombination area among the holes and electrons is located adjacent to an interface between the EML and the HBL, and thereby decreasing the luminous efficiency and the luminous lifetime of the OLED.

Figure 4:
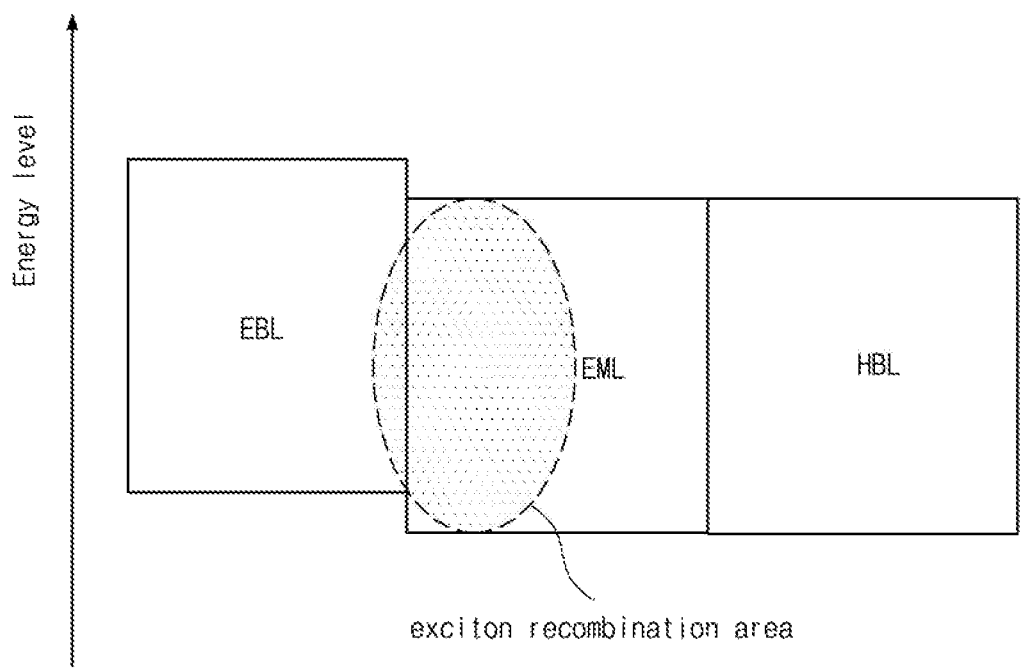
FIG. 4 is a schematic diagram illustrating an exciton recombination area using an organic compound as a n-type host in an emitting material layer in accordance with an exemplary aspect of the present disclosure.

The organic compound of the present disclosure has an n-type property and relatively high excited triplet energy level. As shown in FIG. 4, which is schematic diagram illustrating an exciton recombination area using an organic compound as a n-type host in an emitting material layer in accordance with an exemplary aspect of the present disclosure, electrons transport relatively fast compared to holes owing to the n-type host (organic compound) in the EML, the exciton recombination area among the holes and electrons is located adjacent to an interface between the EML and the EBL. In other words, holes and electrons can be injected in balance into the EML, thus the OLED using the organic compound can increase its luminous efficiency and its luminous lifetime.

The organic compound of the present disclosure may be applied into the organic emissive layer 220, and more specifically, at least one of the EML 240, the HBL 275 and the ETL 270. As an example, the organic compound may be used as the host in the EML 240. The EML 240 may comprise a first compound as a first host and a second compound as a dopant, and the first host may comprise the organic compound. The dopant may be doped with about 1 wt % to about 40 wt %. In one exemplary aspect, the EML 240 may only a first dopant. In this case, the first dopant may be delayed fluorescent material, fluorescent material or a phosphorescent material.

Figure 5:
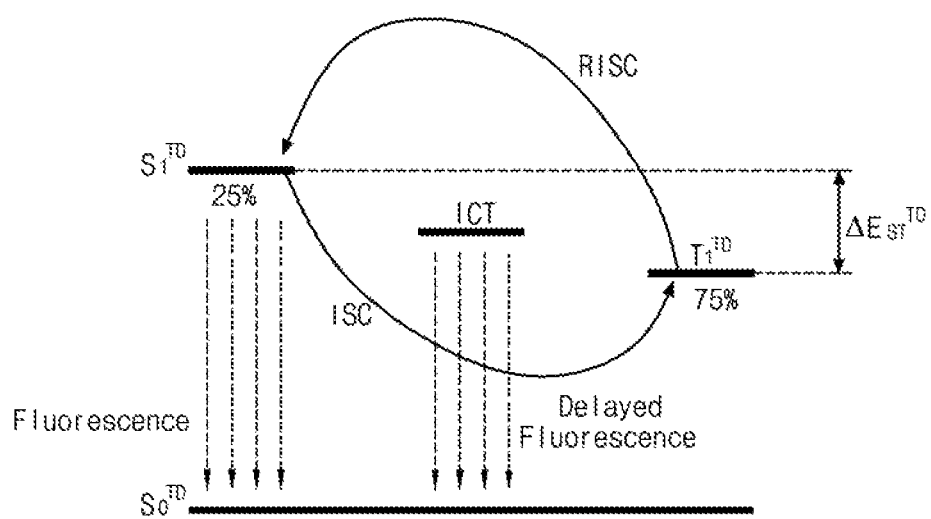
FIG. 5 is a schematic diagram illustrating a luminous mechanism of a delayed fluorescent material.

Now, we will describe luminous mechanism in the EML 240 that includes delayed fluorescent material as a first dopant. FIG. 5 is a schematic diagram illustrating a luminous mechanism of delayed fluorescent material.

Delayed fluorescent can be divided into a thermally-activated delayed fluorescent (TADF) and a filed activated delayed fluorescent (FADF) in which triplet exciton, which is not involved in the convention fluorescent luminescence, is activated by heat or electrical field, so that it is possible to realize excellent luminous efficiency above the maximal luminous efficiency implemented by the conventional fluorescence.

In general, an OLED emits light as holes injected from the anode and electrons injected from the cathode are combined to form exciton in the EML and then unstable excited state exciton returns to a stable ground state. In theory, when electrons meet holes to form excitons, singlet exciton of a paired spin and a triplet exciton of an unpaired spin are produced by a ratio of 1:3 by spin arrangements. Only the singlet exciton among the excitons can be involved in luminescence process in case of fluorescent materials. Accordingly, the OLED may exhibit luminous efficiency by maximum 5% in case of using the conventional fluorescent material.

On the other hand, the triplet exciton in the delayed fluorescent materials is activated by heat or electrical field produced during driving the OLED, and then the activated triplet exciton can be involved in the luminescence process. In more detail, the activated triplet exciton is transferred to a singlet exciton, and then the transferred singlet exciton returns to a ground state with fluorescent luminescence. Since all the excitons can be involved in the luminescence process, the delayed fluorescent material may have maximal 100% internal quantum efficiency in theory as phosphorescent materials including heavy metal.

The delayed fluorescent material must have an energy level bandgap $\Delta E_{ST}^{TD}$ equal to or less than about 0.3 eV, for example, from about 0.05 to about 0.3 eV, between the excited singlet energy level $S_1^{TD}$ and the excited triplet energy level $T_1^{TD}$ so that exciton energy in both the singlet energy level and the triplet energy level can be transferred to the ICT (intramolecular charge transfer) state. The material having little energy level bandgap between the singlet energy level $S_1^{TD}$ and the triplet energy level $T_1^{TD}$ can exhibit common fluorescence in which the excitons of singlet energy level $S_1^{TD}$ can be transferred to the ground state $S_0^{TD}$, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be transferred to the ground state $S_0^{TD}$.

Returning to FIG. 2, when the EML 240 comprise the organic compound as the first host (first compound) and the delayed fluorescent material as the first dopant (second compound), an energy level bandgap ($|HOMO_{HOST}-HOMO_{DOPANT}|$) between a HOMO (highest occupied molecular orbital) energy level ($HOMO_{HOST}$) of the first host and a HOMO energy level ($HOMO_{DOPANT}$) of the first dopant, or an energy level bandgap ($|LUMO_{HOST}-LUMO_{DOPANT}|$) between a LUMO (lowest unoccupied molecular orbital) energy level ($LUMO_{HOST}$) of the first host and a LUMO energy level ($LUMO_{DOPANT}$) of the first dopant may be equal to or less than about 0.5 eV. In this case, charges can be transferred efficiently from the first host to the first dopant.

As an example, the first dopant of delayed fluorescent property may comprise anyone having the following structure of Chemical Formula 4:

[Chemical Formula 4]

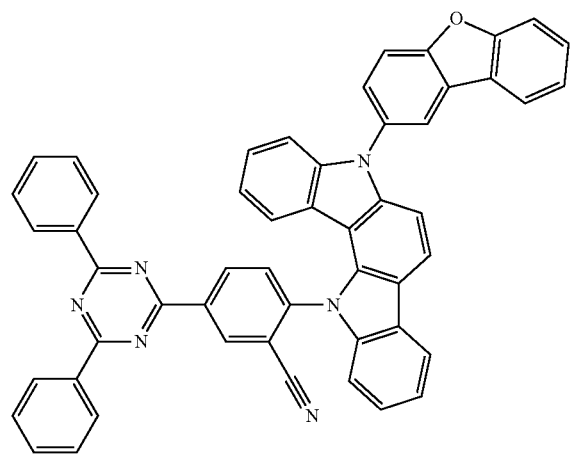

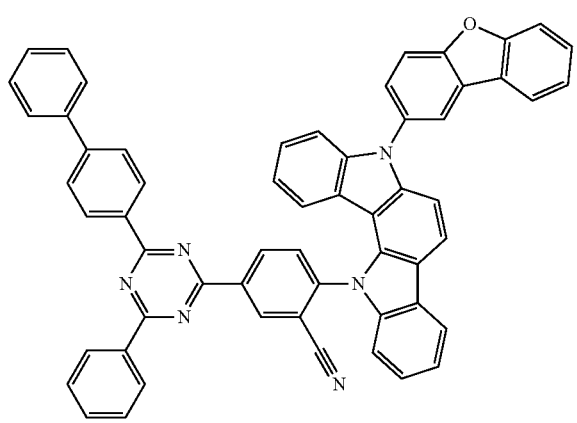

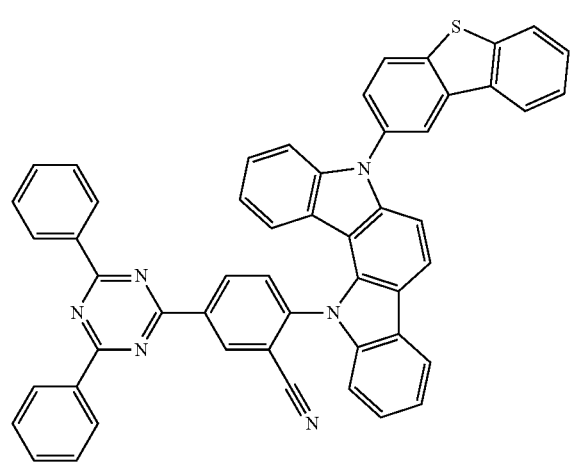

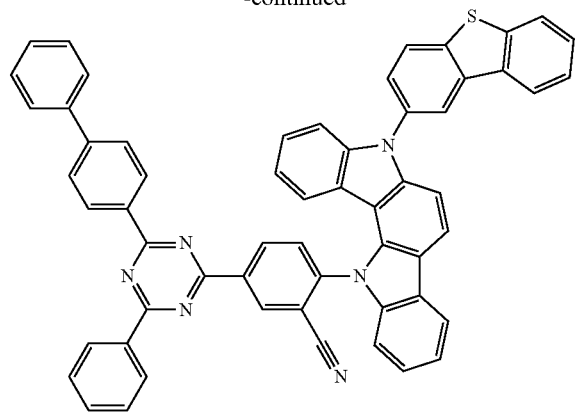
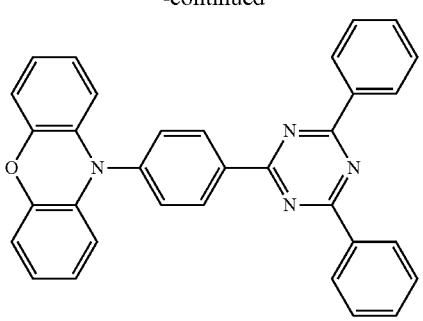
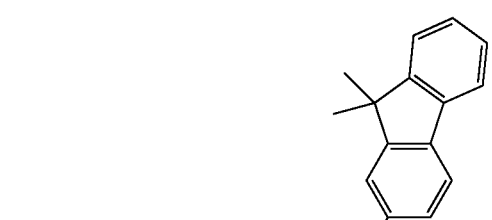
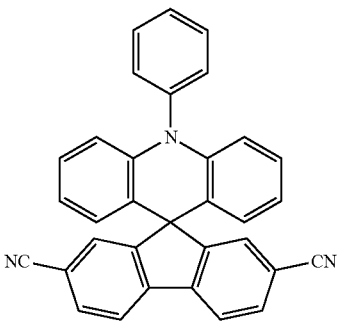
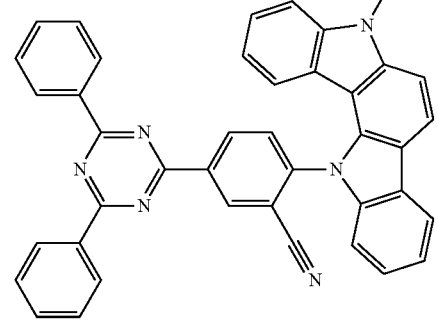
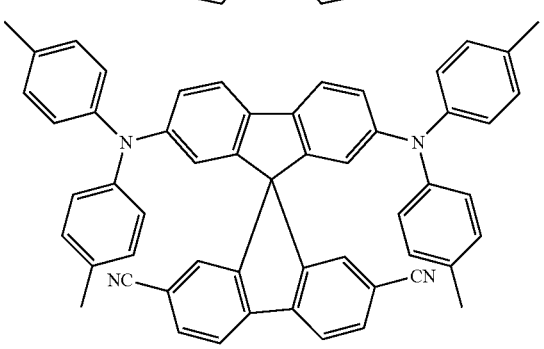
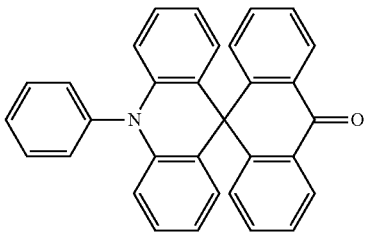
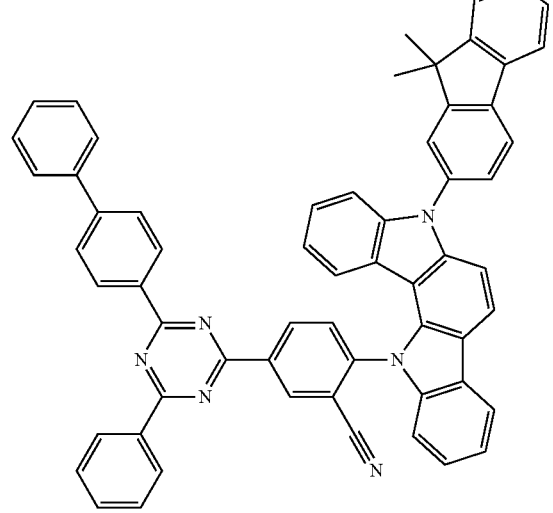
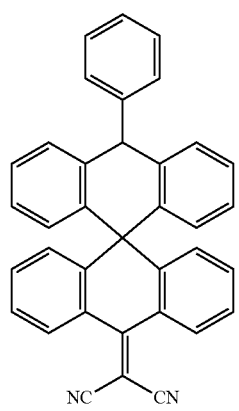

47
-continued
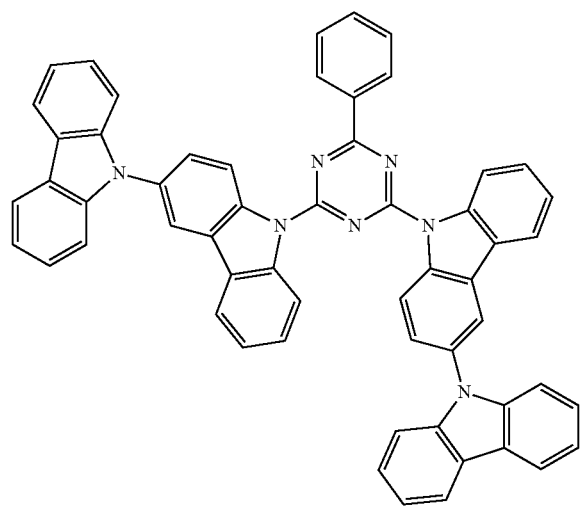
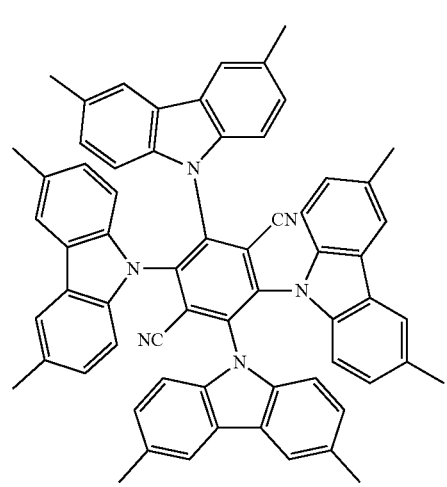
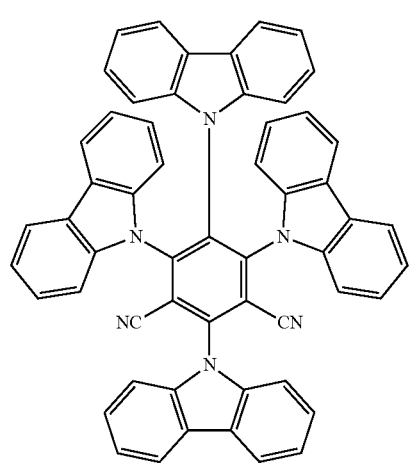
48
-continued
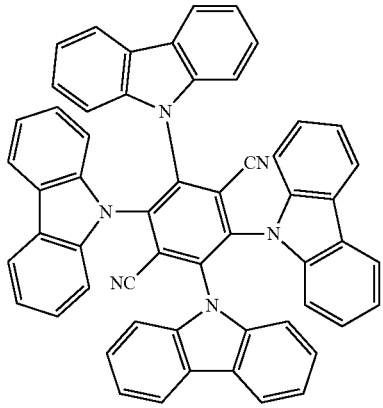
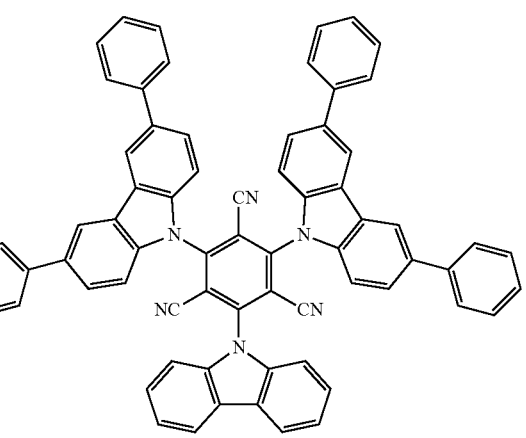
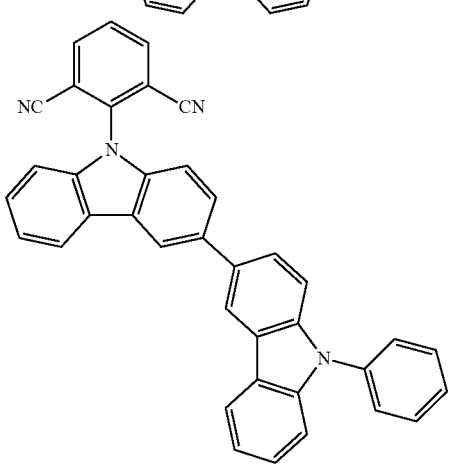
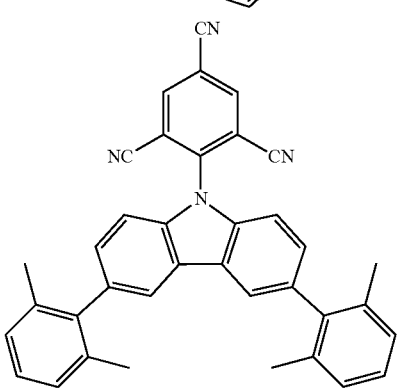

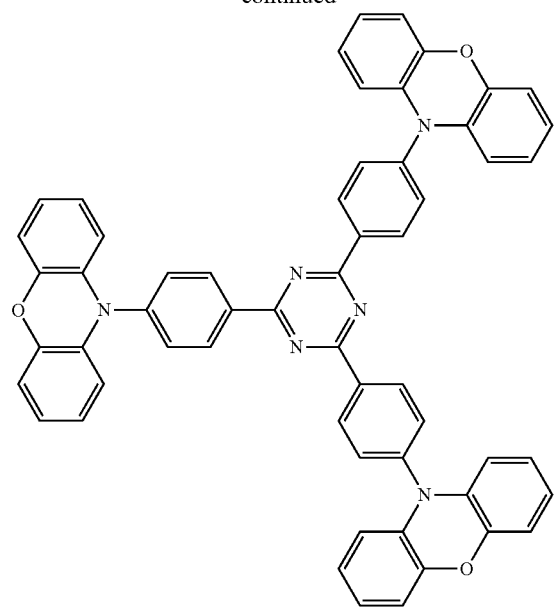

51
-continued
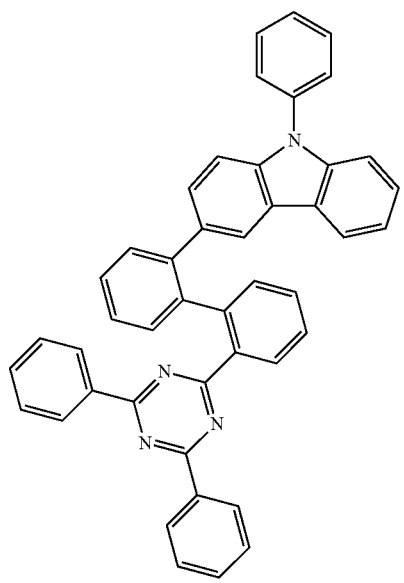
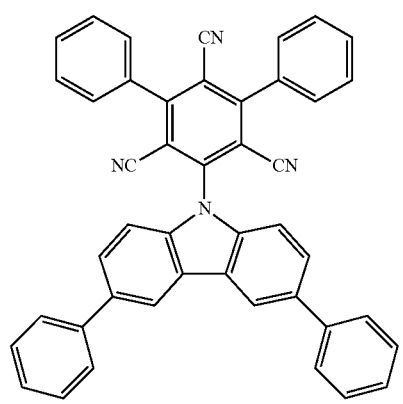
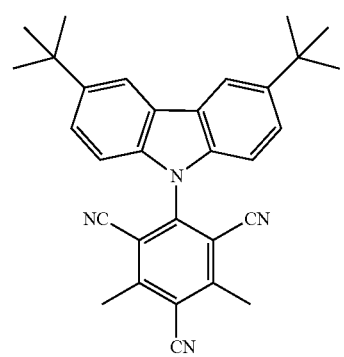
52
-continued
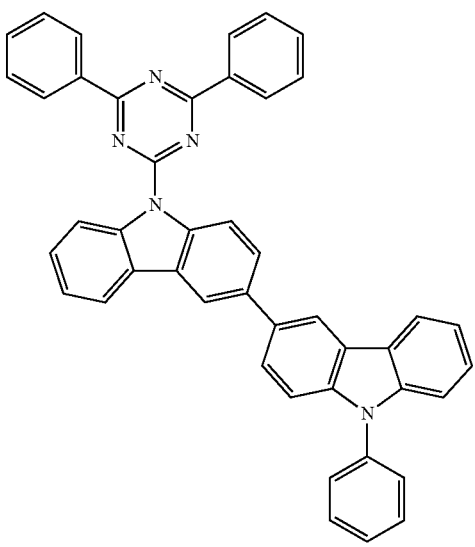
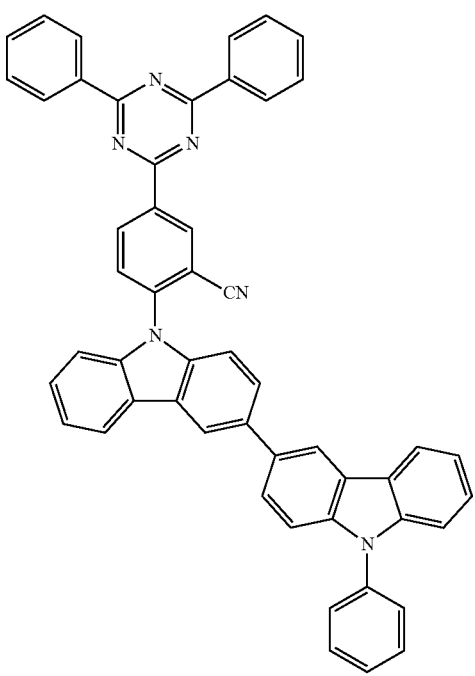

53
-continued
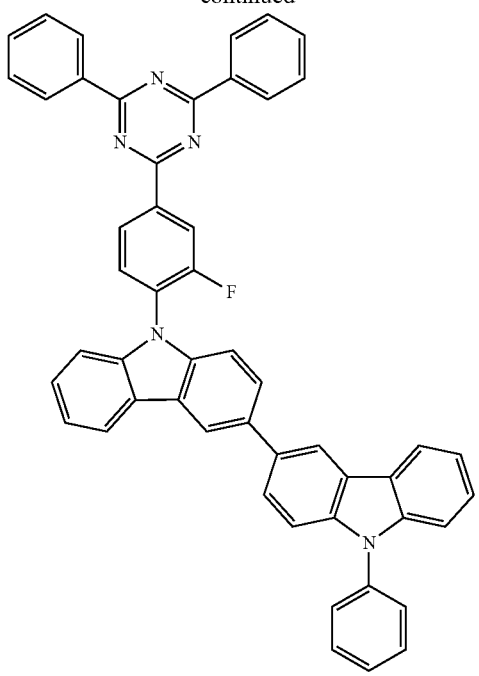
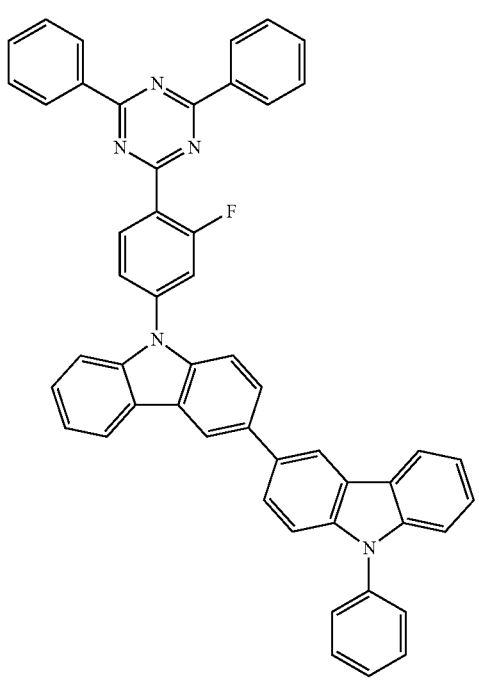
54
-continued
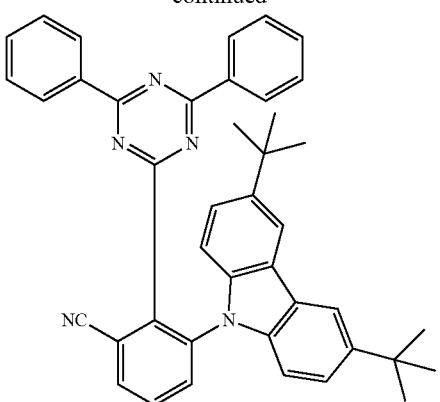
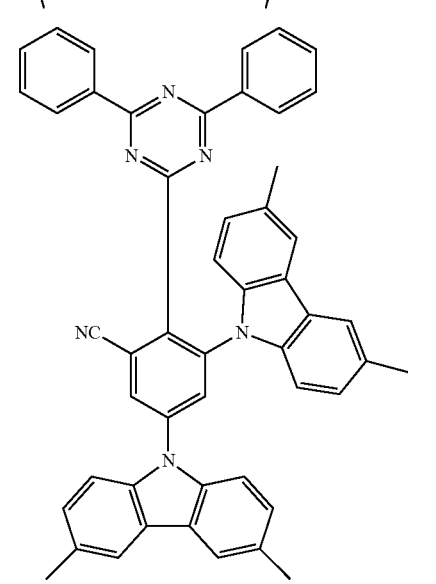
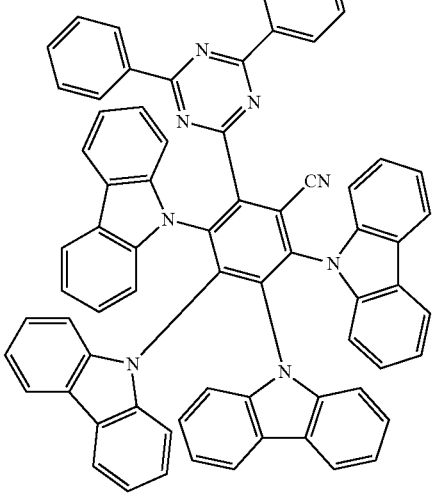

55
-continued
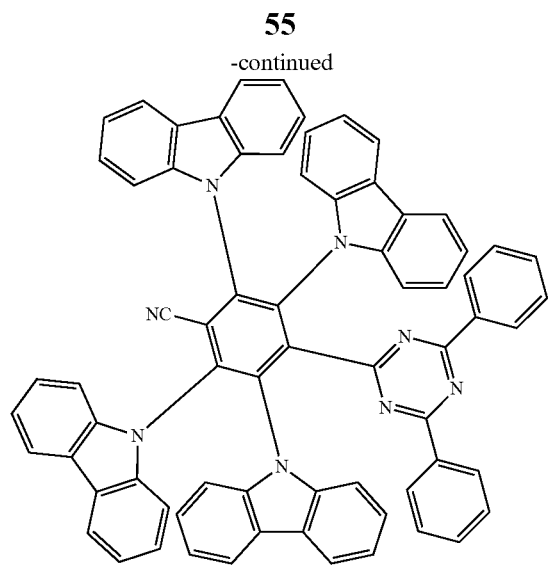
56
-continued
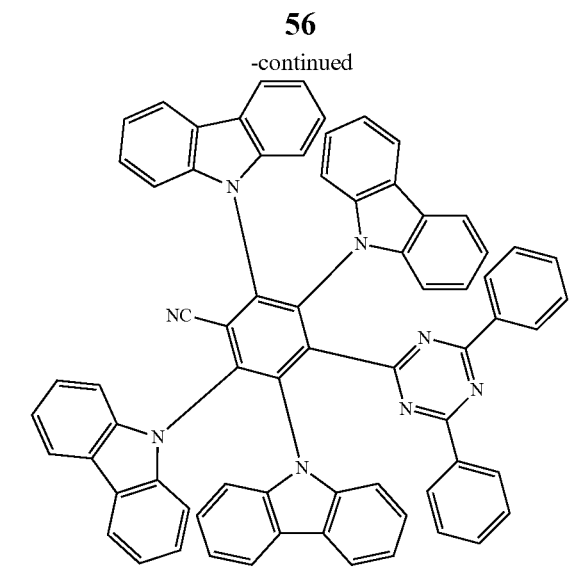
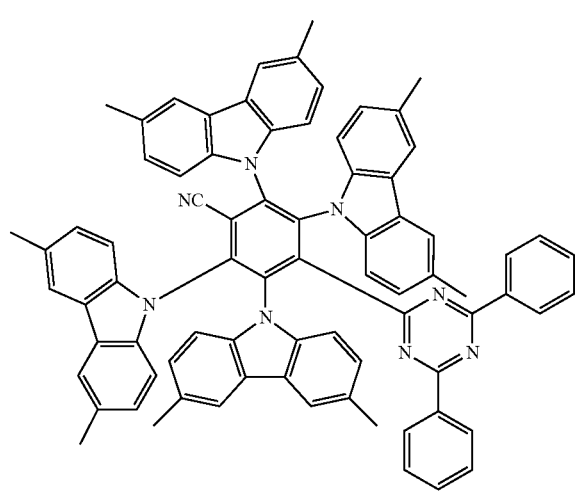
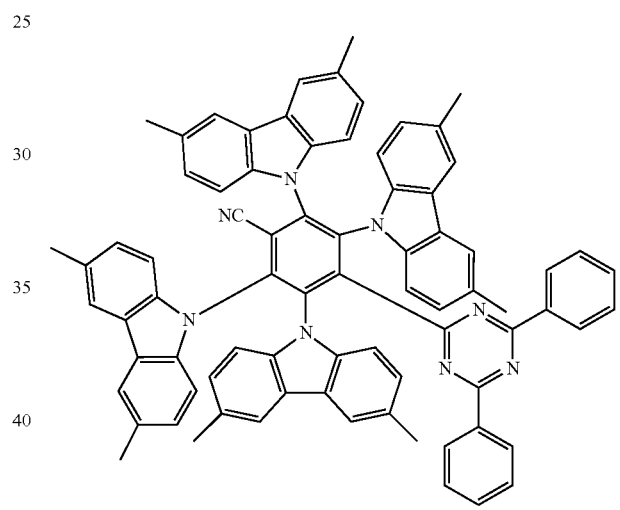
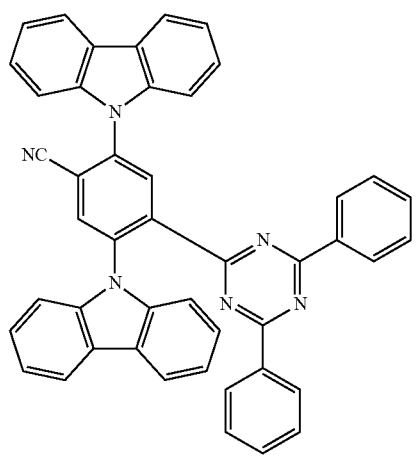
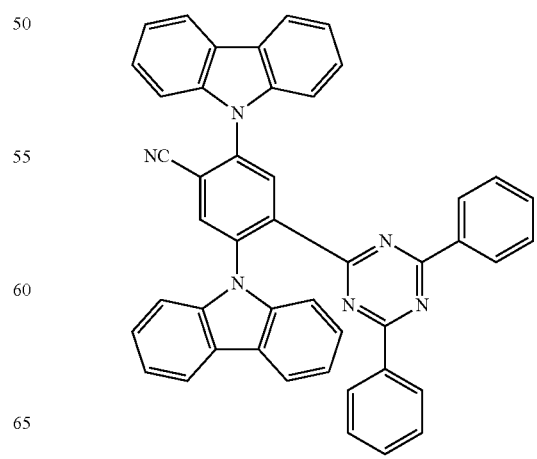

57
-continued
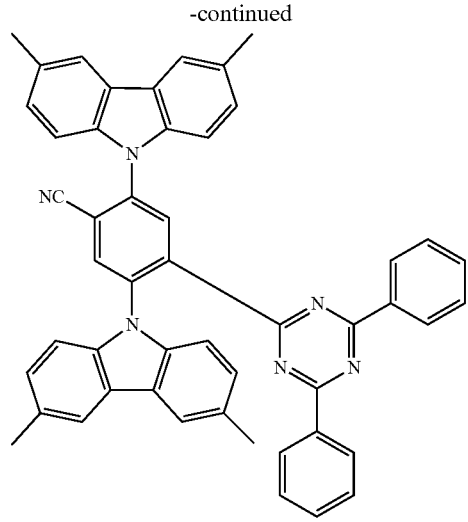
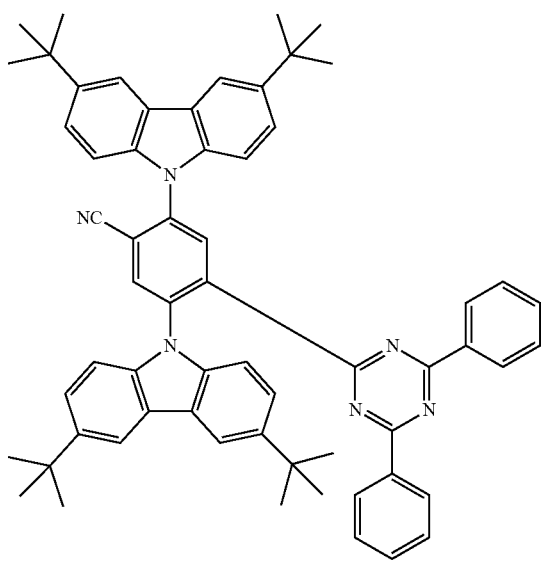
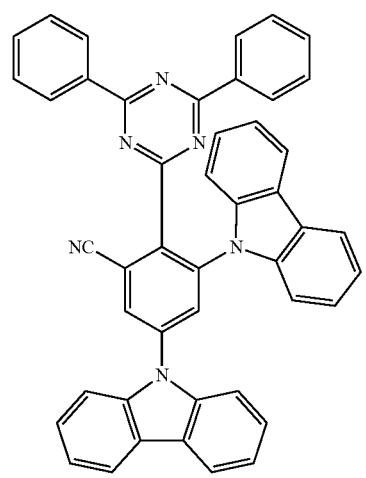
58
-continued
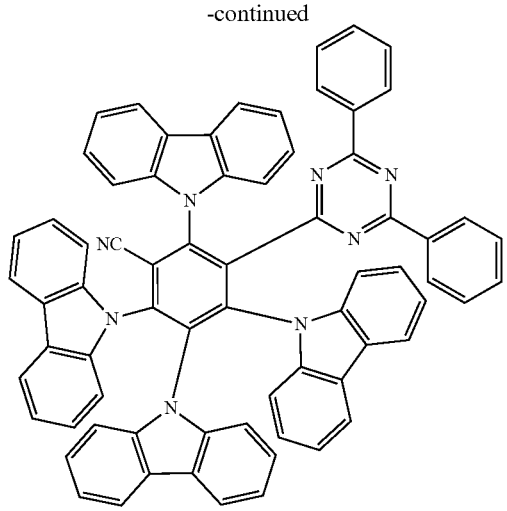
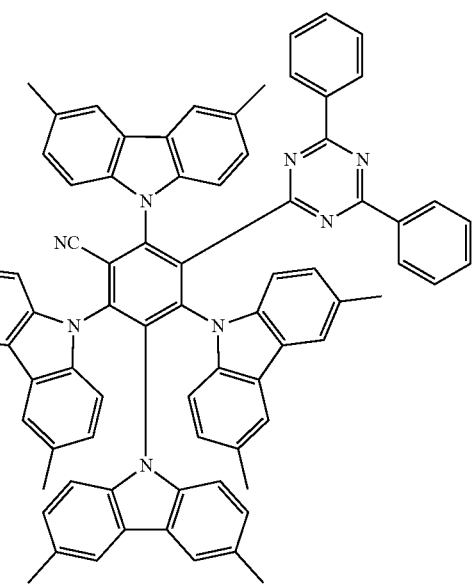
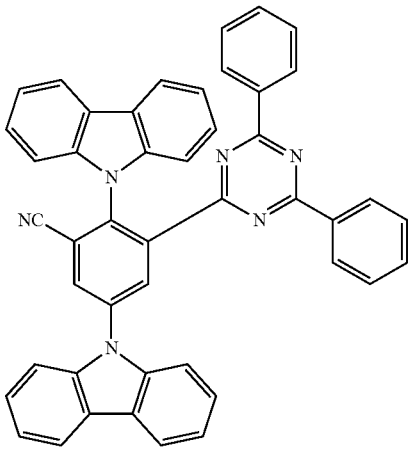

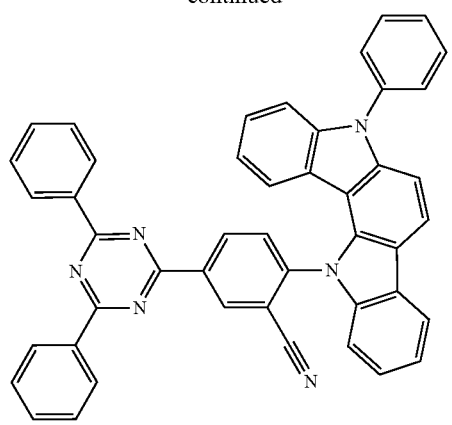
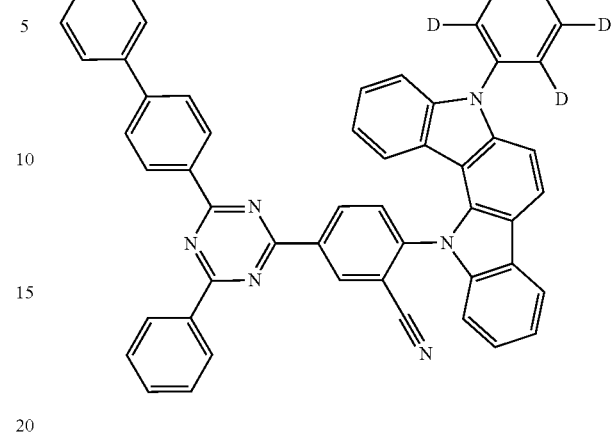
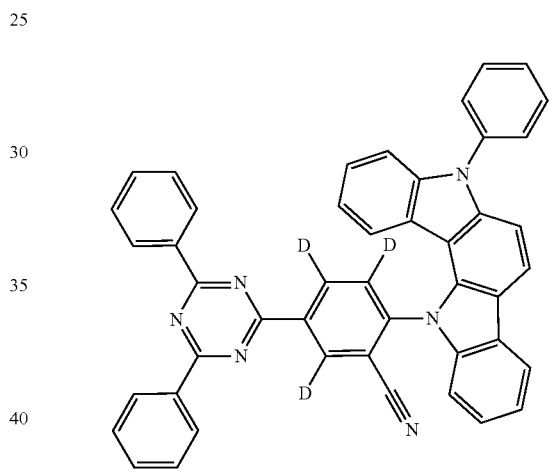
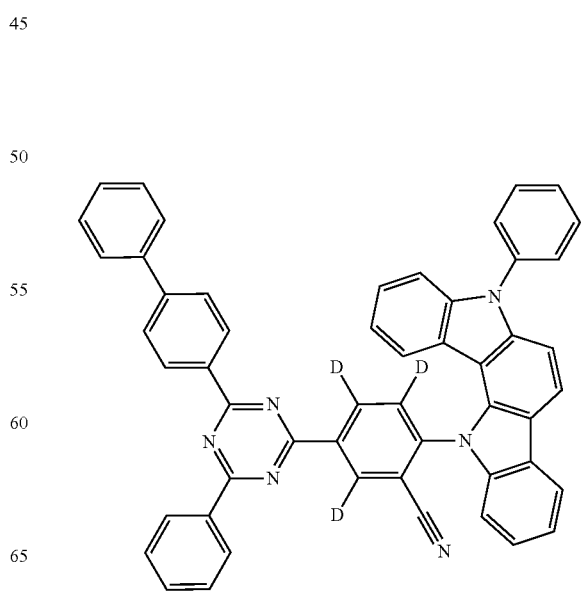
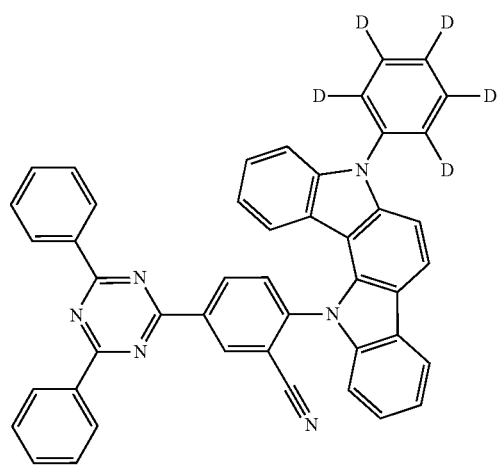

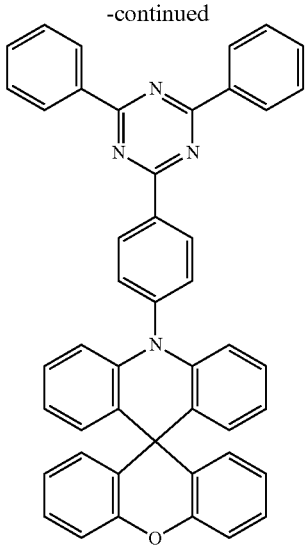

In addition, an excited triplet energy level of the first dopant, i.e. delayed fluorescent material, is lower than an excited triplet energy level of the first host, i.e. the organic compound. Besides, an energy level bandgap ($\Delta E_{ST}^{TD}$) between the excited singlet energy level $S_1^{TD}$ and the excited triplet energy level $T_1^{TD}$ of the first dopant is very small ($\Delta E_{ST}^{TD}$ is equal to or less than about 0.3 eV; See, FIG. 6) so that triplet exciton energy of the first dopant can be transferred to the singlet exciton energy of its own by RISC mechanism and therefore increase its luminous efficiency.

Figure 6:
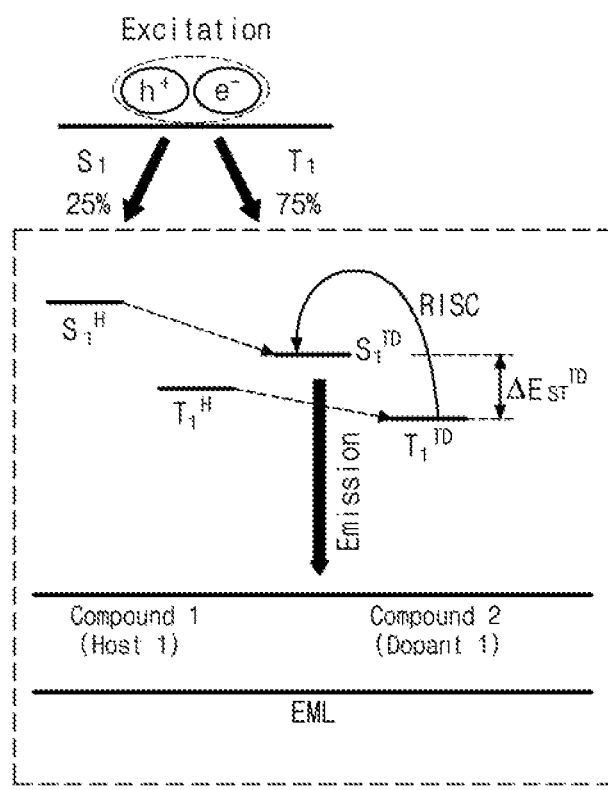
FIG. 6 is a schematic diagram illustrating luminous mechanism by energy level bandgap among luminous materials in accordance with an exemplary aspect of the present disclosure.

Referring to FIG. 6, only 25% excitons are in singlet state and 75% excitons are in triplet state among excitons generated by recombining between holes and electrons in the first compound (first host). Each of singlet excitons and triplet excitons in the first compound (first host) is respectively transferred to singlet excitons and triplet excitons in the second compound (first dopant) each of which singlet and triplet energy levels is lower than that of the first compound, respectively. The transferred triplet exciton of the second compound is transferred by heat or electrical field to its own singlet exciton, which is higher energy level than that of the triplet state, via RISC. Plural excitons transferred from the triplet state to the singlet state return to the ground state with fluorescence. In this case, each of an excited singlet energy level $S_1^H$ and an excited triplet energy level $T_1^H$ of the first host is higher than each of an excited singlet energy level $S_1^{TD}$ and an excited triple energy level $T_1^{TD}$ of the first dopant having the delayed fluorescent property, respectively.

In another exemplary aspect, the EML 240 may comprise the organic compound as a first host, the delayed fluorescent material as a first dopant, and optionally fluorescent material as a second dopant. In this case, the total contents of the first and second dopants may be about 1 wt % to about 40 wt % in the EML 240. In this case, an excited singlet energy level of the first dopant, i.e. delayed fluorescent material, is higher than an excited singlet energy level of the second dopant, i.e. fluorescent material. Also, an excited triplet energy level of the first dopant is lower than an excited triplet energy level of the first host, i.e. the organic compound.

When the EML 240 comprises the first host and the first and second dopants, it is possible to enhance the luminous efficiency and color purity thereof. The exciton energy is transferred from the host to the first dopant, and then singlet and triplet energies are transferred from the first dopant to the second dopant in which final emission is occurred. When the second dopant has a narrow FWHM (full-width half maximum), the EML 240 can enhance its luminous efficiency and make its FWHM narrow.

While the first dopant of delayed fluorescent property has high internal quantum efficiency, but it has poor color purity due to its wide FWHM (full-width half maximum). On the contrary, the second dopant of fluorescent material has advantage of color purity due to its narrow FWHM, but its internal quantum efficiency is low because its triplet exciton cannot be involved in the luminous process. However, when the EML 240 comprises both the first dopant as delayed fluorescent material and the second dopant as fluorescent material, the EML 240 has advantages in both the luminous efficiency and color purity.

As an example, the second dopant as fluorescent material may comprise, but is not limited to, any one of the following Chemical Formula 5:

[Chemical Formula 5]

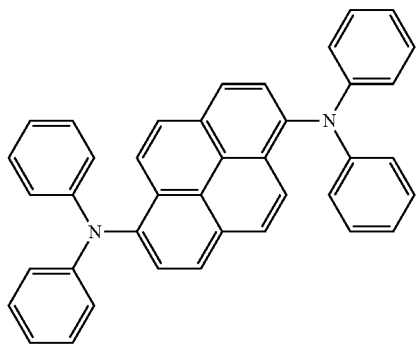

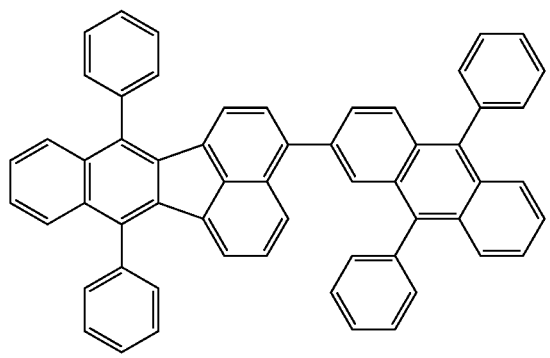

-continued

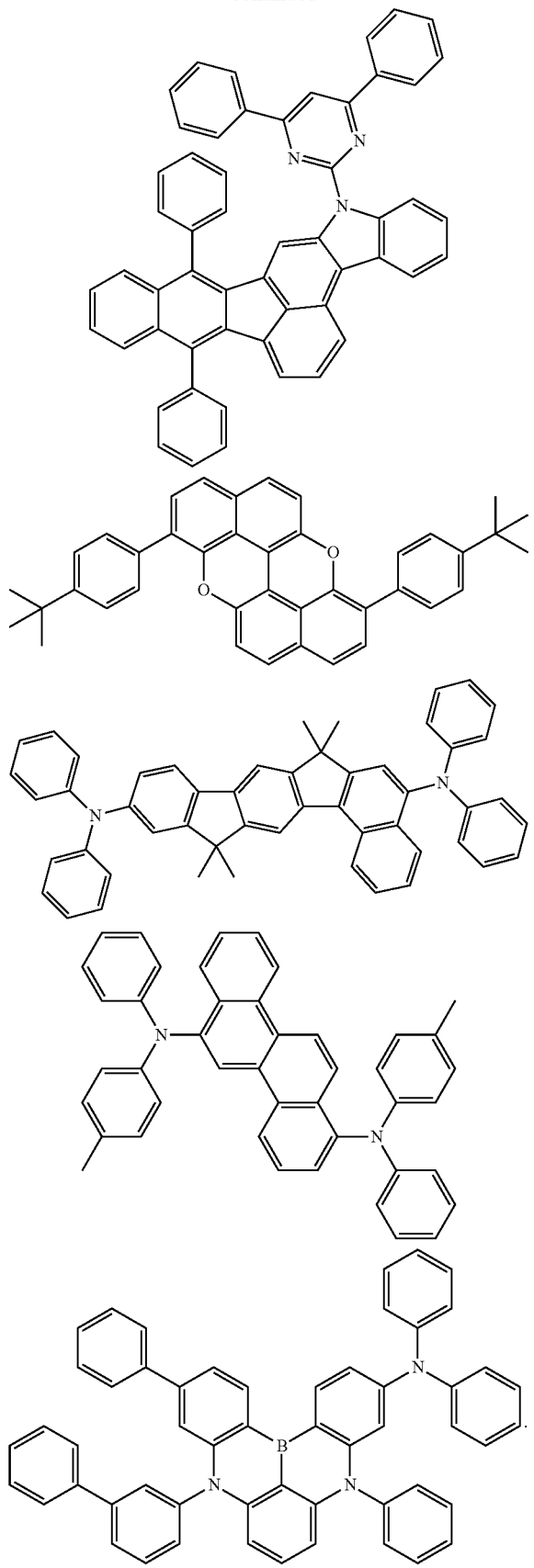

When the EML 240 comprises the organic compound as the first host, the delayed fluorescent material as the first dopant and the fluorescent material as the second dopant, each of an excited singlet energy level $S_1^H$ and an excited triplet energy level $T_1^H$ of the first host is higher than each of the excited singlet energy level $S_1^{TD}$ and the excited triplet energy level $T_1^{TD}$ of the first dopant, respectively. Moreover, the excited triplet energy level $T_1^{TD}$ of the first dopant is higher than an excited triplet energy level $T_1^{FD}$ (see, FIG. 8) of the second dopant. Also, the excited singlet energy level $S_1^{TD}$ of the first dopant may be higher than an excited singlet energy level $S_1^{FD}$ (see, FIG. 8) of the second dopant.

Figure 7:
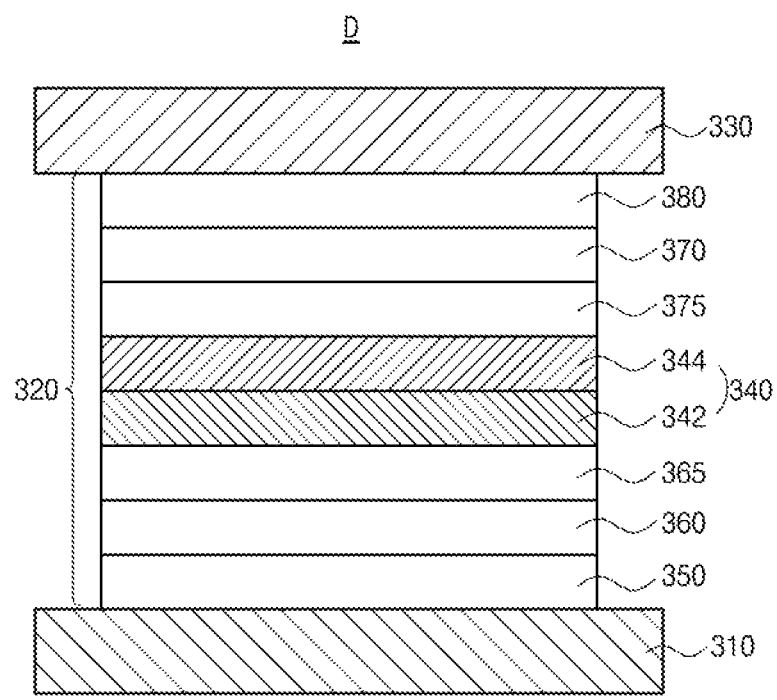
FIG. 7 is a schematic cross-sectional view illustrating an organic light emitting diode in accordance with another exemplary aspect of the present disclosure.
Figure 8:
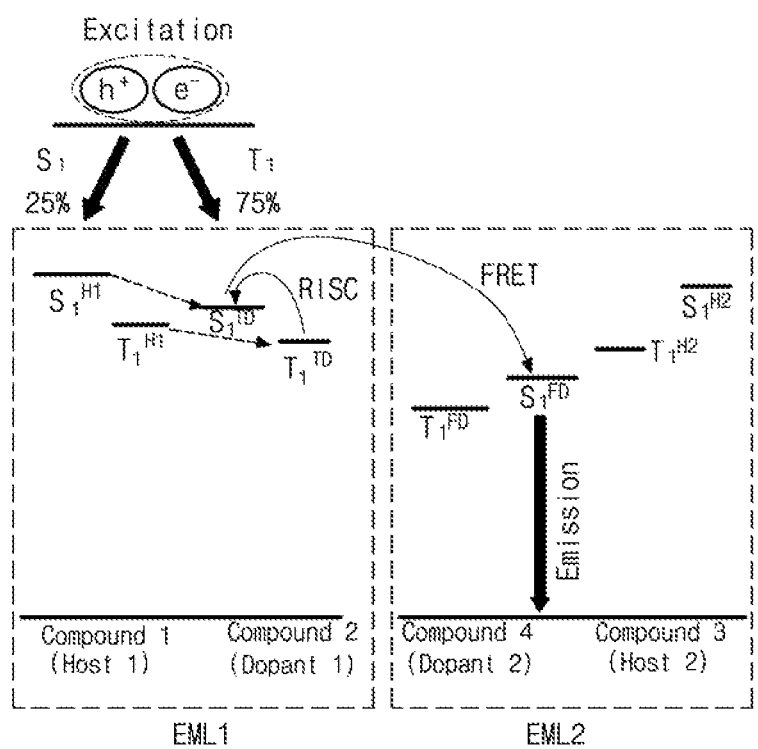
FIG. 8 is a schematic diagram illustrating luminous mechanism by energy level bandgap among luminous materials in accordance with another exemplary aspect of the present disclosure.

FIG. 7 is a schematic cross-sectional view illustrating an organic light emitting diode in accordance with another exemplary aspect of the present disclosure and FIG. 8 is a schematic diagram illustrating luminous mechanism by energy level bandgap among luminous materials in accordance with another exemplary aspect of the present disclosure. The organic light emitting diode D comprises a first electrode 310, an organic emissive layer 320 and a second electrode 330. The organic emissive layer 320 may comprise a HIL 350, a HTL 360, an EBL 365, an EML 340, a HBL 375, an ETL 370 and/or an EIL 380. The organic emissive layer 320 in FIG. 7 may have the same structure as shown in FIG. 2 except the EML 340.

The EML 340 comprise a first EML (EML1) 342 and a second EML (EML2) 344. The EML1 342 is disposed between the EBL 365 and the HBL 375 and the EML2 344 is disposed between the EML1 342 and the HBL 375. One of the EML1 342 and the EML2 344 comprises a first dopant, i.e. delayed fluorescent material, the other of the EML1 342 and the EML2 344 includes a second dopant, i.e. fluorescent material. For example, the EML1 342 comprises a first compound as a first host and a second compound as a first dopant, i.e. delayed fluorescent material, and the EML2 344 comprises a third compound as a second host and a fourth compound as a second dopant, i.e. fluorescent material. As an example, each of the first host and the second host is the organic compound.

Referring to FIG. 8, each of singlet excitons and triplet excitons in the first compound (first host) is respectively transferred to each of the singlet excitons and triplet excitons in the second compound (first dopant) each of which energy levels is lower than that of the first compound in the EML1 342, respectively. The transferred triplet exciton of the second compound is transferred by heat or electrical field to its own singlet exciton, which is higher energy level than that of the triplet state, via RISC. In addition, the singlet exciton of the second compound (first dopant) is transferred to the singlet exciton of the fourth compound (second dopant). The singlet exciton of the fourth compound, which is transferred from the second compound, returns to the ground state with fluorescence.

In this case, each of excited singlet energy levels $S_1^{H1}$ and $S_1^{H2}$ and excited triplet energy levels $T_1^{H1}$ and $T_1^{H2}$ of the first and second hosts is higher than each of the excited singlet energy level $S_1^{TD}$ and the excited triplet energy level $T_1^{TD}$ of the first dopant, respectively. Also, the excited singlet energy level $S_1^{H2}$ of the second host is higher than an excited state singlet energy level $S_1^{FD}$ of the second dopant. In addition, the excited triplet energy level $T_1^{TD}$ of the first dopant is higher than an excited triplet energy level Tim of the second dopant. Also, the excited singlet energy level $S_1^{TD}$ of the first dopant may be higher than an excited singlet energy level $S_1^{FD}$ of the second dopant.

In an alternative aspect, the EML2 344 may be omitted and the EBL 365 and/or the HBL 375 may further comprise the fourth compound as the second dopant, i.e. fluorescent material.

Figure 9:
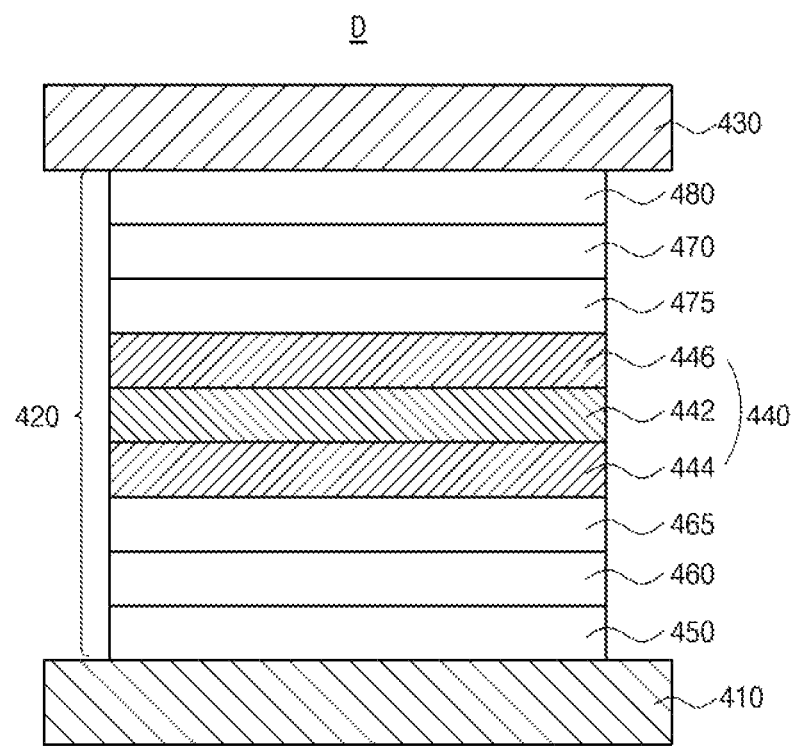
FIG. 9 is a schematic cross-sectional view illustrating an organic light emitting diode in accordance with another exemplary aspect of the present disclosure.
Figure 10:
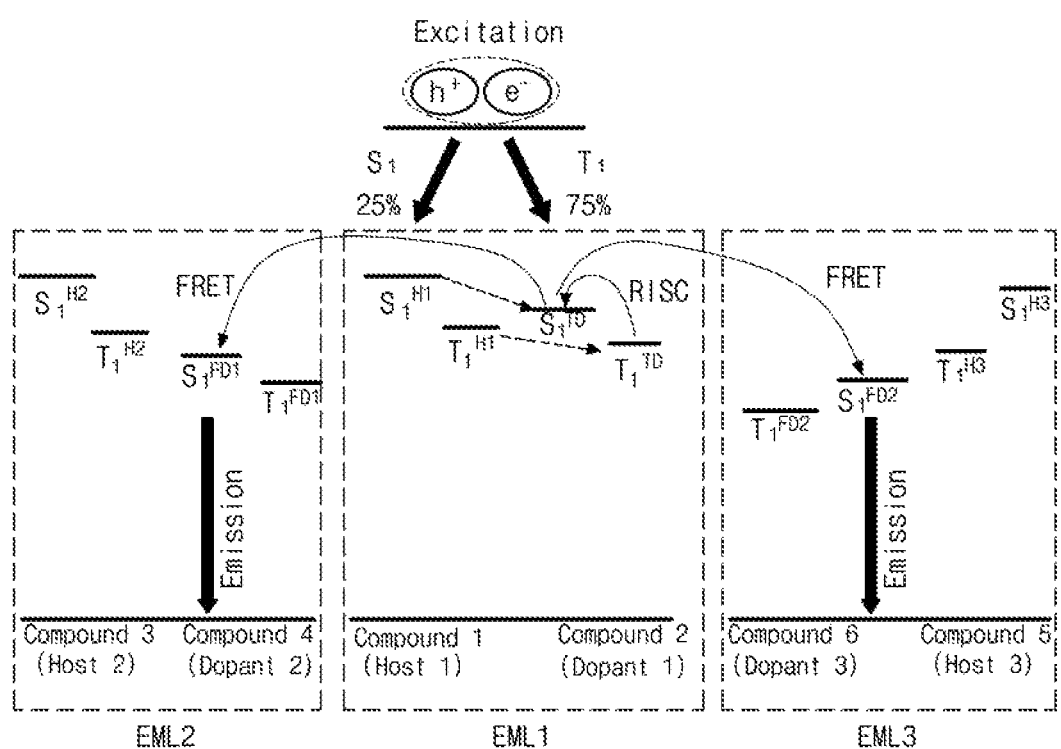
FIG. 10 is a schematic diagram illustrating luminous mechanism by energy level bandgap among luminous materials in accordance with another exemplary aspect of the present disclosure.

FIG. 9 is a schematic cross-sectional view illustrating an organic light emitting diode in accordance with another exemplary aspect of the present disclosure and FIG. 10 is a schematic diagram illustrating luminous mechanism by energy level bandgap among luminous materials in accordance with another exemplary aspect of the present disclosure. The organic light emitting diode D comprises a first electrode 410, an organic emissive layer 420 and a second electrode 430. The organic emissive layer 420 may comprise a HIL 450, a HTL 460, an EBL 465, an EML 440, a HBL 475, an ETL 470 and/or an EIL 480. The organic emissive layer 420 in FIG. 9 may have the same structure as shown in FIG. 2 except the EML 440.

The EML 440 comprise a first EML (EML1) 442, a second EML (EML2) 444 and a third EML (EML3) 446. The EML1 442 is disposed between the EBL 465 and the HBL 475, the EML2 444 is disposed between the EBL 465 and the EML1 442 and the EML3 446 is disposed between the EML1 442 and the HBL 475. Each of the EML1 442, the EML2 444 and the EML3 446 comprise a host and a dopant. For example, the EML1 442 comprise a first compound as a first host and a second compound as a first dopant, i.e. delayed fluorescent material, the EML2 444 comprises a third compound as a second host and a fourth compound as a second dopant, i.e. fluorescent material, the EML3 446 comprises a fifth compound as a third host and a sixth compound as a third dopant, i.e. fluorescent material.

As an example, each of the first host to the third host is the organic compound. Alternatively, each of the second and third hosts in the EML2 444 and the EML3 446 is identical to the EBL 465 or the HBL 475, at least one of the EBL 465 and HBL 475 may be omitted.

Referring to FIG. 10, each of singlet excitons and triplet excitons in the first compound (first host) is respectively transferred to each of the singlet excitons and triplet excitons in the second compound (first dopant) each of which energy levels is lower than that of the first compound in the EML1 442, respectively. The transferred triplet exciton of the second compound is transferred by heat or electrical field to its own singlet exciton, which is higher energy level than that of the triplet state, via RISC. In addition, singlet state exciton of the second compound (first dopant) is transferred to singlet exciton of the fourth and sixth compounds (second and third dopants) in the EML2 444 and EML 446. The singlet excitons of the fourth and sixth compounds, each of which is transferred from the second compound, return to the ground state with fluorescence.

In this case, each of excited singlet energy level $S_1^{H1}$, $S_1^{H2}$ and $S_1^{H3}$ and excited triplet energy levels $T_1^{H2}$, $T_1^{H3}$ and $T_1^{H3}$ of the first to third hosts is higher than each of the excited singlet energy level $S_1^{TD}$ and the excited triplet energy level $T_1^{TD}$ of the first dopant, respectively. Also, each of the excited singlet energy levels $S_1^{H2}$ and $S_1^{H3}$ of the second and third hosts is higher than each of excited state singlet energy levels $S_1^{FD1}$ and $S_1^{FD2}$ of the second and third dopants, respectively. In addition, the excited triplet energy level $T_1^{TD}$ of the first dopant is higher than each of excited triplet energy levels $T_1^{FD1}$ and $T_1^{FD2}$ of the second and third dopants, respectively. Also, the excited singlet energy level $S_1^{TD}$ of the first dopant may be higher than each of excited singlet energy levels $S_1^{FD1}$ and $S_1^{FD2}$ of the second and third dopants.

In an alternative aspect, each of the EML2 444 and the EML3 446 may be omitted and the EBL 465 and/or the HBL 475 may further comprise the fourth compound as the second dopant i.e. fluorescent material and the sixth compound as the third dopant, i.e. fluorescent material, respectively.

Synthesis Example 1: Synthesis of Compound 1

(1) Synthesis of Intermediate C

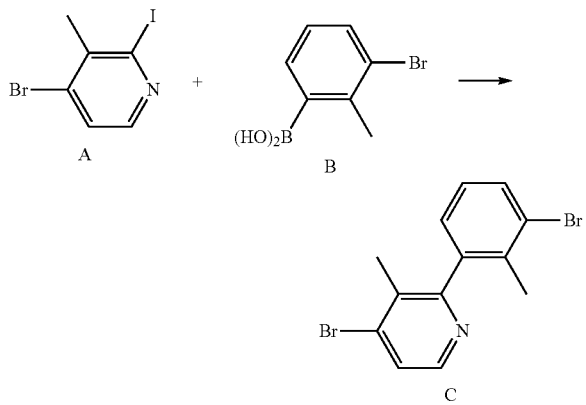

Compound A (1 equivalent) was dissolved in dioxane and compound B (0.9 equivalent) was added to the solution under nitrogen atmosphere. Potassium carbonate (2.5 equivalents) dissolved in DI water was added into the mixed solution and [1,1'-bis(di-cyclohexylphosphino)ferrocene]dichloropalladium (II) (0.02 equivalent) was added into the solution, and then the mixed solution was stirred at 90° C. for 8 hours. After reaction was complete, the organic layer was extracted with dichloromethane and DI water and the solvent was removed via vacuum distillation. Obtained crude product was purified via column chromatography using hexane: dichloromethane as an eluent to give intermediate C.

(2) Synthesis of Compound 1

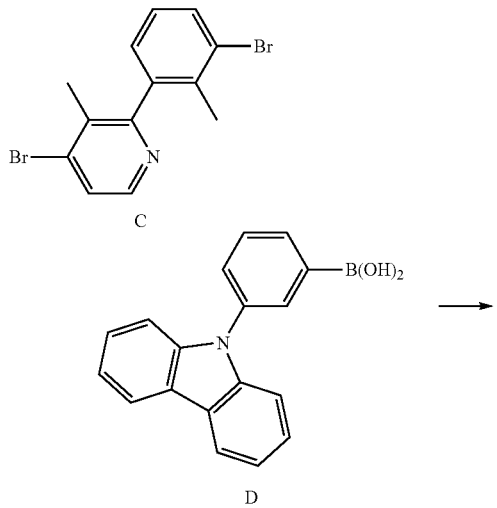

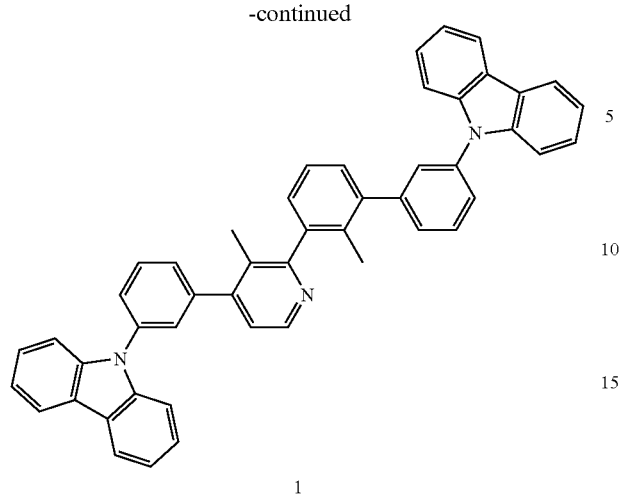

Intermediate C (1 equivalent), compound D (2.1 equivalents), potassium carbonate (4 equivalents) and tetrakis(triphenylpohsphine)palladium (0.05 equivalent) were added into a mixed solvent of toluene:water:THF (6:2:1). After purging the solution with nitrogen, the solution was stirred at 90° C. for 10 hours. After reaction was complete, the organic layer was extracted with dichloromethane and DI water and the solvent was removed via vacuum distillation. Obtained crude product was purified with column chromatography using hexane: dichloromethane as an eluent to give Compound 1.

Synthesis Example 2: Synthesis of Compound 3

(1) Synthesis of Intermediate G

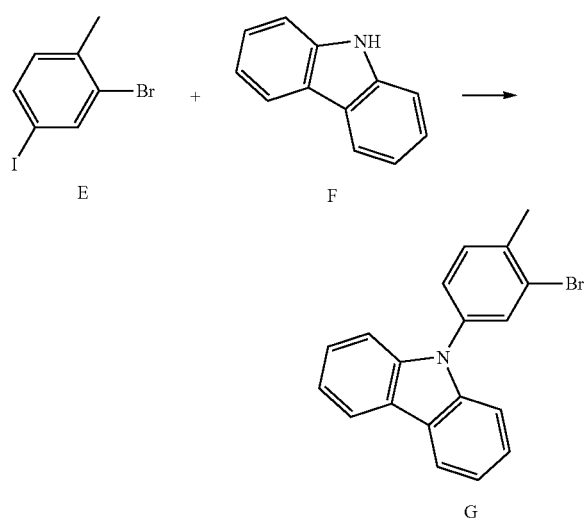

Compound E (1 equivalent) was dissolved in toluene and then compound F (0.9 equivalent) was added to the solution under nitrogen atmosphere. Sodium t-butoxide (4.0 equivalents), tris(dibenzylideneacetonate)dipalladium(0) (Pd$_2$(dba)$_3$, 0.04 equivalent) and tri-tert-butyl phosphine were added into the solution, and then the solution was stirred at 80° C. for 12 hours. After reaction was complete, the organic layer was extracted with dichloromethane and DI water and the solvent was removed via vacuum distillation. Obtained crude product was purified with column chromatography using hexane: dichloromethane as an eluent to give intermediate G.

(2) Synthesis of Intermediate I

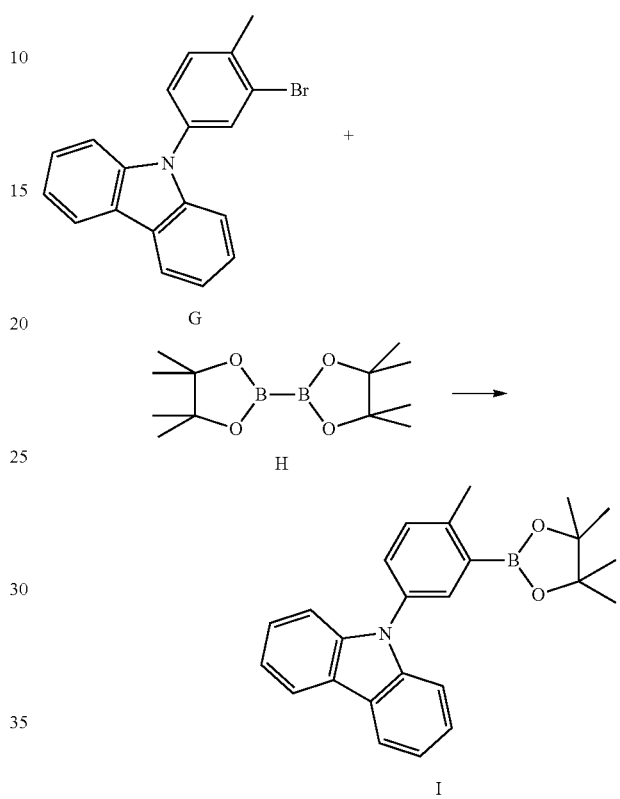

Intermediate G (1 equivalent), compound H (2.0 equivalents), potassium acetate (KOAc, 3.0 equivalents), palladium(II) acetate (Pd(OAc)$_2$, 0.04 equivalent) and 2-cyclohexylphosphino-2',4',6'-triisopropylbiphenyl (XPhos, 0.08 equivalent) were added into dioxane, and then the solution was purged with nitrogen and stirred at 110° C. for 12 hours. After reaction was complete, the organic layer was extracted with dichloromethane and DI water and the solvent was removed via vacuum distillation. Obtained crude product was purified with column chromatography using hexane: dichloromethane as an eluent to give intermediate I.

(3) Synthesis of Compound 3

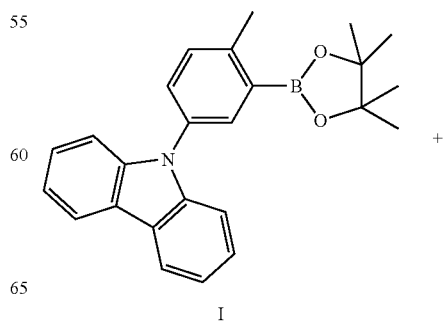

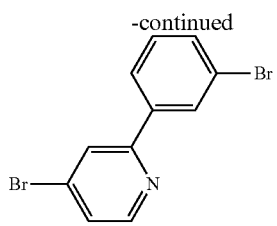

J

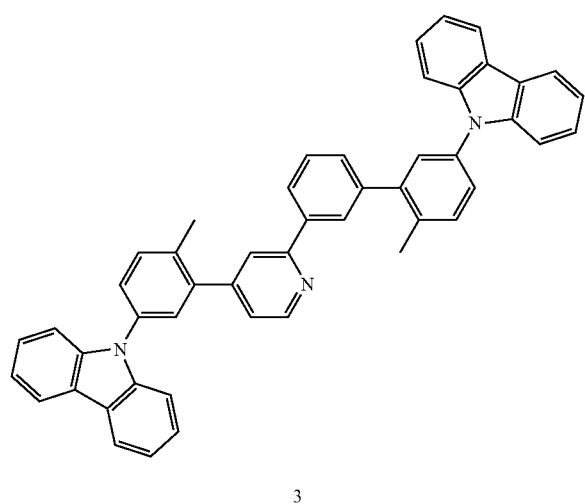

3

Intermediate I (2 equivalents) was dissolved in dioxane and then compound J (1.0 equivalent) was added into the solution under nitrogen atmosphere. Potassium carbonate (2.5 equivalents) dissolved in DI water and [1,1'-bis(dicyclohexylphosphino)ferrocene]dichloropalladium (II) (0.02 equivalent) were added into the solution, and the solution was stirred at 90° C. for 24 hours. After reaction was complete, the organic layer was extracted with dichloromethane and DI water and the solvent was removed via vacuum distillation. Obtained crude product was purified with column chromatography using hexane: dichloromethane as an eluent to give Compound 3.

Synthesis Example 3: Synthesis of Compound 25

(1) Synthesis of Intermediate L

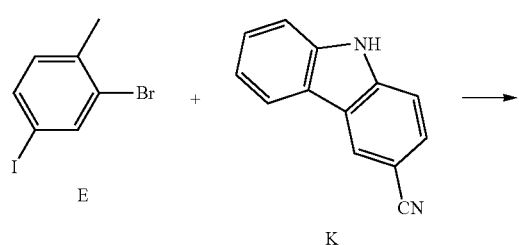

E      K

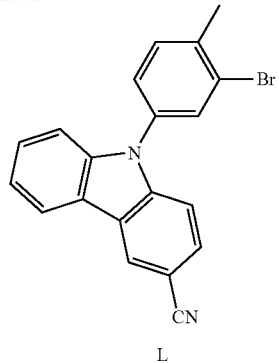

L

Compound E (1 equivalent) was dissolved in toluene and then compound K (0.9 equivalent) was added to the solution under nitrogen atmosphere. Sodium t-butoxide (4.0 equivalents), Pd$_2$(dba)$_3$ (0.04 equivalent) and tri-tert-butyl phosphine were added into the solution, and then the solution was stirred at 80° C. for 12 hours. After reaction was complete, the organic layer was extracted with dichloromethane and DI water and the solvent was removed via vacuum distillation. Obtained crude product was purified with column chromatography using hexane: dichloromethane as an eluent to give intermediate L.

(2) Synthesis of Intermediate M

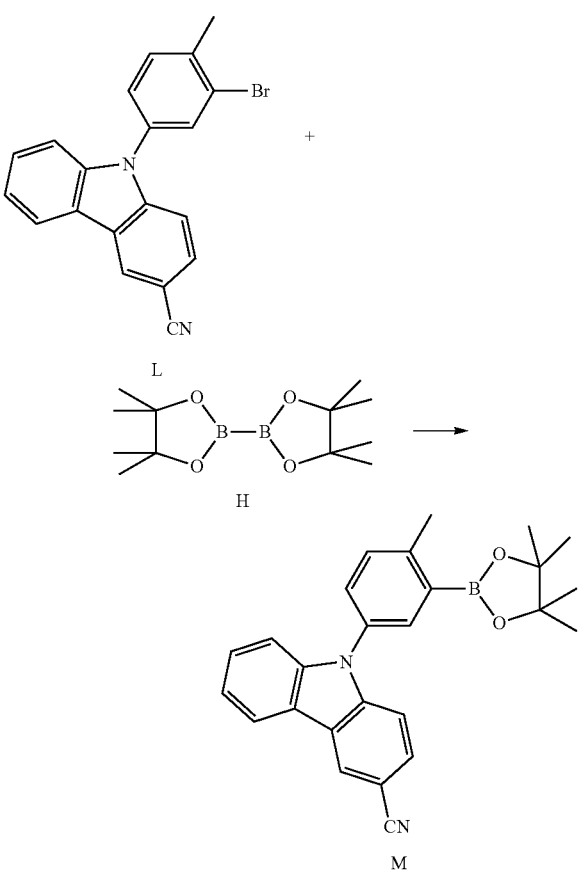

Intermediate L (1 equivalent), compound H (2.0 equivalents), KOAc (3.0 equivalents), Pd(OAc)$_2$ (0.04 equivalent) and XPhos (0.08 equivalent) were added into dioxane, and then the solution was purged with nitrogen and stirred at 110° C. for 12 hours. After reaction was complete, the organic layer was extracted with dichloromethane and DI water and the solvent was removed via vacuum distillation. Obtained crude product was purified with column chromatography using hexane: dichloromethane as an eluent to give intermediate M.

(3) Synthesis of Intermediate N

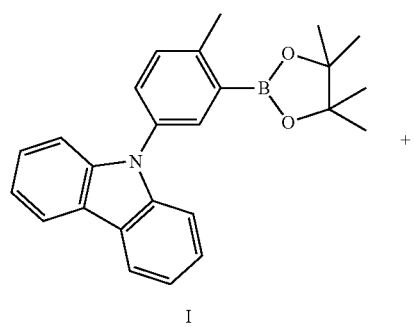

I

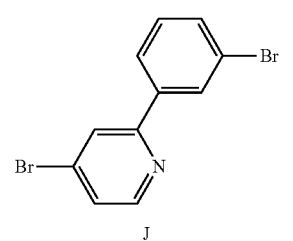

J

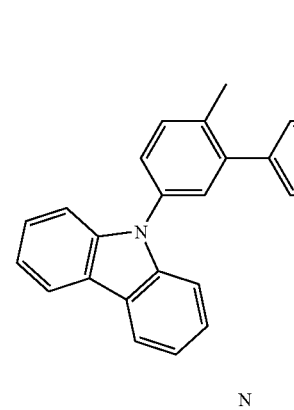

N

Intermediate I (1 equivalents) was dissolved in dioxane and then compound J (5.0 equivalent) was added into the solution under nitrogen atmosphere. Potassium carbonate (2.5 equivalents) dissolved in DI water and [1,1'-bis(dicyclohexylphosphino)ferrocene]dichloropalladium (II) (0.02 equivalent) were added into the solution, and the solution was stirred at 90° C. for 24 hours. After reaction was complete, the organic layer was extracted with dichloromethane and DI water and the solvent was removed via vacuum distillation. Obtained crude product was purified with column chromatography using hexane: dichloromethane as an eluent to give intermediate N.

(4) Synthesis of Compound 25

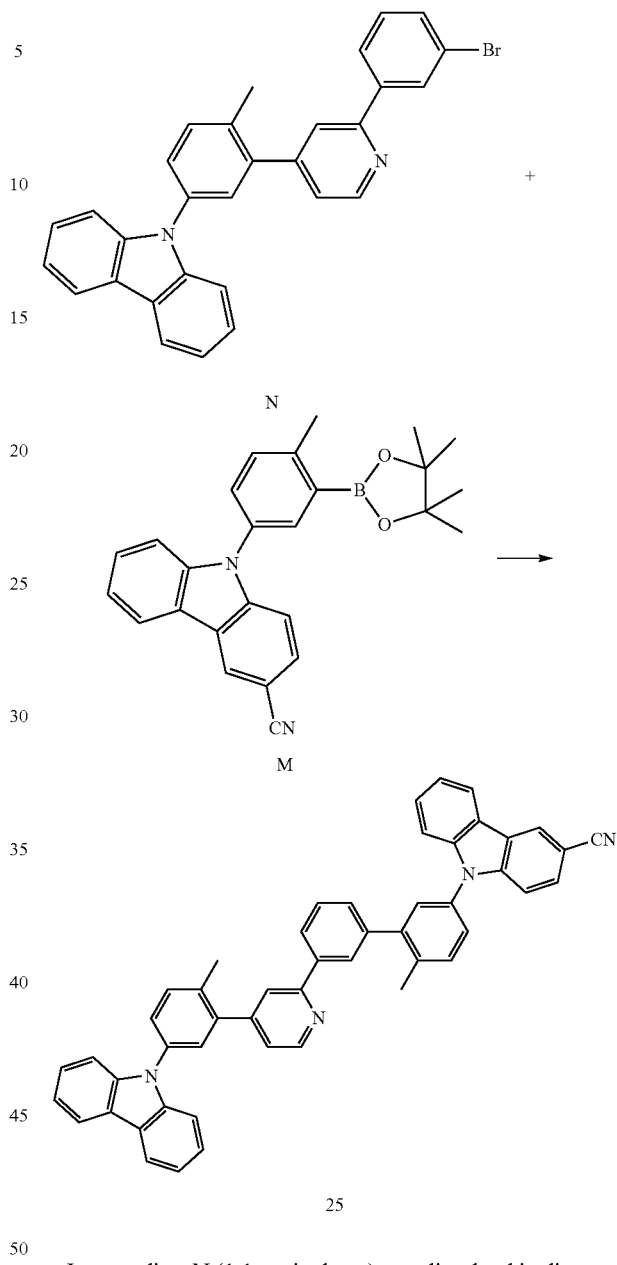

Intermediate N (1.1 equivalents) was dissolved in dioxane and then intermediate M (1.0 equivalent) was added into the solution under nitrogen atmosphere. Potassium carbonate (2.5 equivalents) dissolved in DI water and [1,1'-bis(dicyclohexylphosphino)ferrocene]dichloropalladium (II) (0.02 equivalent) were added into the solution, and the solution was stirred at 90° C. for 24 hours. After reaction was complete, the organic layer was extracted with dichloromethane and DI water and the solvent was removed via vacuum distillation. Obtained crude product was purified with column chromatography using hexane: dichloromethane as an eluent to give Compound 25.

Experiment Example 1: Measurement of Physical Property

Physical properties, i.e. HOMO level (, LUMO level, excited triplet energy level ($E_T$) and energy bandgap ($E_g$)

between HOMO level and LUMO level for some organic compounds in Chemical Formula 3 were measured. Also, physical properties for the reference compounds, which are shown below, were measured. The measurement results are shown in table 1 below:

[Reference Compound]

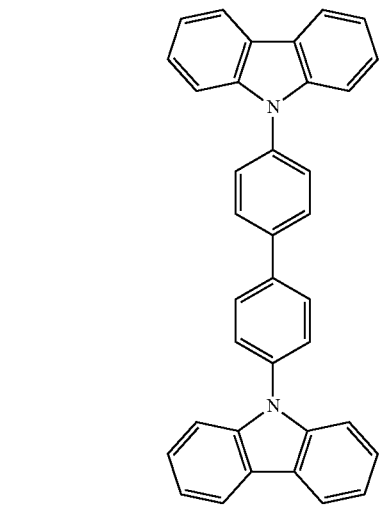

Ref. 1

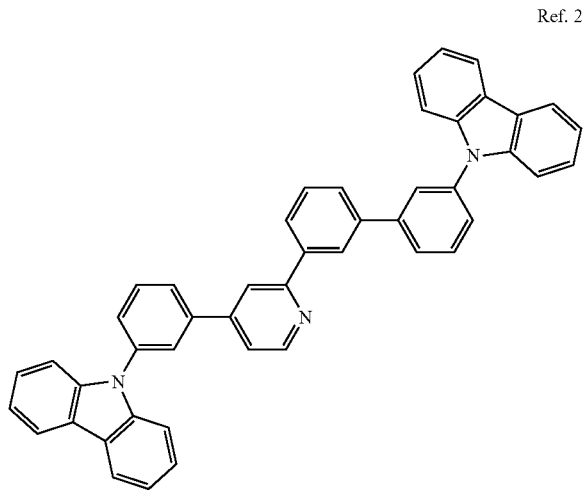 [SMILES: Cc1cc(-c2cccc(-c3cc(-c4cc(C)cc(-n5c6ccccc6c6ccccc65)c4)ccn3)c2)cc(-n2c3ccccc3c3ccccc32)c1]

Ref. 2

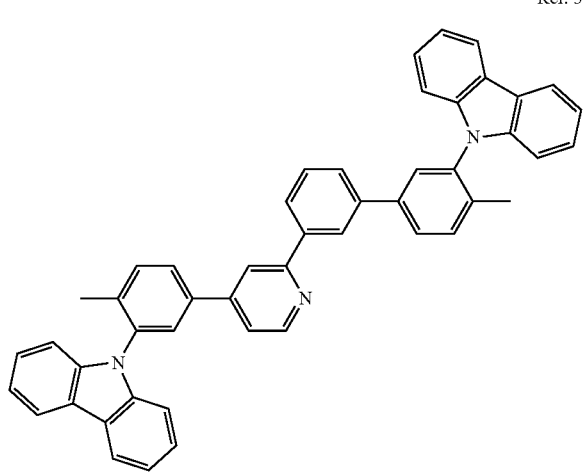

Ref. 3

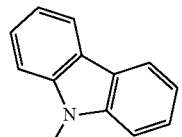

Ref. 4

TABLE 1

Energy Level of Compounds

| Compound | $E_T$(eV) | HOMO(eV) | LUMO(eV) | $E_g$(eV) |
|---|---|---|---|---|
| Ref. 1 | 2.68 | −5.76 | −2.51 | 3.25 |
| Ref. 2 | 2.87 | −5.78 | −2.59 | 3.19 |
| Ref. 3 | 2.88 | −5.75 | −2.53 | 3.22 |
| Ref. 4 | 2.83 | −5.67 | −2.40 | 3.27 |
| 1 | 3.12 | −5.77 | −2.33 | 3.44 |
| 2 | 3.10 | −5.73 | −2.39 | 3.34 |
| 3 | 3.12 | −5.78 | −2.42 | 3.36 |
| 4 | 3.13 | −5.77 | −2.42 | 3.35 |
| 5 | 3.14 | −5.75 | −2.30 | 3.45 |
| 6 | 3.13 | −5.73 | −2.34 | 3.39 |
| 15 | 3.15 | −5.78 | −2.29 | 3.49 |
| 19 | 3.12 | −5.79 | −2.41 | 3.37 |
| 20 | 3.13 | −5.82 | −2.43 | 3.39 |
| 23 | 3.13 | −5.95 | −2.53 | 3.38 |
| 31 | 3.11 | −5.65 | −2.23 | 3.42 |
| 38 | 3.12 | −5.84 | −2.44 | 3.40 |

As shown in Table 1, compared to the p-type host, Ref. 1 (CBP), the organic compounds according to the present disclosure has higher excited triplet energy level. Accordingly, the organic compounds according to the present disclosure can be used as a host, and can realize higher energy efficiency. Also, the organic compounds can be used as an n-type host so that the exciton recombination area can be moved to an interface between the EML and EBL, and have advantages in luminous efficiency and luminous lifetime compared to the conventional p-type host.

In particular, as shown in Table 1, the organic compounds that is substituted with alkyl group in the phenyl and/or pyridine rings showed higher excited triplet energy levels ($E_T$) compared to the Ref. 2 that is not substituted except to $A_1$ and $A_2$ positions. In addition, we confirmed that the organic compounds in accordance with the present disclosure showed higher excited triplet energy level, compared to the Ref. 3 and Ref. 4 each of which is substituted with alkyl group at positions other than those designated as $R_1$-$R^8$ in Chemical Formula 1.

In other words, when the organic compounds have the substituent such as an alkyl group located at the specific position, i.e. $R_1$ to $R_8$ position defined in Chemical Formula 1, the excited triplet energy levels of the compounds are raised, and therefore, the organic compound defined in Chemical Formula 1 showed much enhanced luminous efficiency and luminous lifetime, compared to the Ref. 3 and Ref. 4 compounds that is substituted at positions not designated as $R_n$ (n=1 to 8) in Chemical Formula 1 with the identical core structure as the organic compounds of the present disclosure.

Example 1: Fabrication of OLED

An OLED (Ex. 1) was fabricated in a vacuum deposition chamber under $10^{-7}$ torr in the following order:

HIL (HAT-CN; 50 Å); HTL (NPB, 500 Å); EBL (MCP, 100 Å); EML (Host (Compound 1): dopant (Chemical Formula 6)=70:30 wt %, 300 Å); ETL (TPBi, 300 Å); EIL (LiF, 10 Å); and cathode (Al, 1000 Å).

[Chemical Formula 6]

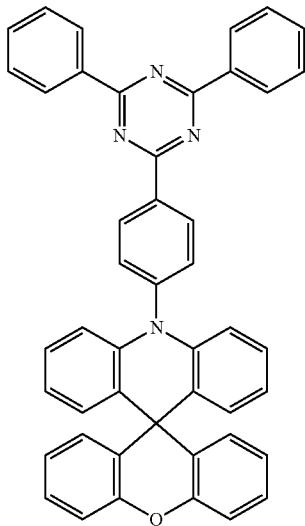

Examples 2-3 (Ex. 2-3): Fabrication of OLED

An OLED was fabricated using the Compound 3 (Ex. 2) or Compound 25 (Ex. 3) as a host in the EML.

Comparative Examples 1-2 (Ref. 1-2): Fabrication of OLED

An OLED was fabricated using the Ref. 1 compound (Ref. 1) or the Ref. 2 compound (2, Ref. 2) as a host in the EML.

Experimental Example 2: Measurement of Luminous Properties of OLED

Each of the OLED fabricated by Examples 1 to 3 and Ref. 1 to Ref. 2 was connected to an external power source and then luminous properties for all the diodes were evaluated using a constant current source (KEITHLEY) and a photometer PR650 at room temperature. In particular, driving voltage (V), External Quantum Efficiency (EQE, %), CIE color coordinates at a current density of 10 mA/cm² of the OLEDs were measured. The results thereof are shown in the following Table 2.

TABLE 2

| Luminous Properties of OLED | | | |
|---|---|---|---|
| Sample | V | EQE (%) | CIEy |
| Ref. 1 | 4.5 | 6.3 | 0.343 |
| Ref. 2 | 3.9 | 7.9 | 0.329 |
| Ex. 1 | 3.7 | 15.7 | 0.327 |
| Ex. 2 | 3.2 | 13.1 | 0.328 |
| Ex. 3 | 3.3 | 13.9 | 0.330 |

As indicated in Table 2, compared with the OLEDs in Ref. 1 and Ref. 2, the OLEDs in Ex. 1 to Ex. 3 enhanced its luminous efficiency (EQE) significantly. When an excited triplet energy level of a host is higher than an excited triplet energy level of a dopant in an EML comprising the host and the dopant, their energy efficiency is increased, and therefore, p-type dopants such as CBP has been mainly used. But, the p-type hosts results in deteriorating luminous efficiency and luminous lifetime of an OLED, which is caused by a shift of the exciton recombination area in the EML. Referring to FIGS. 3 and 4, the p-type host caused the exciton recombination area to be shifted at an interface between the EML and the HBL, but the organic compound of the present disclosure as an n-type host causes the exciton recombination area to be shifted at an interface between the EML and the EBL. As the exciton recombination area is shifted, the OLEDs using the organic compounds of the present disclosure enhanced their luminous efficiency and luminous lifetime compared to the OLEDs using the p-type host.

Also, the OLED fabricated by Ref. 2, which uses the Ref. 2 compound as an n-type host that is not substituted with any group in the phenyl rings and the pyridine rings except the donor moiety (carbazolyl group) and therefore, has lower excited triplet energy level, showed reduced luminous efficiency compared to the OLEDs fabricated by Ex. 1 to Ex. 3. Accordingly, when the OLED comprises the organic compound of the present disclosure as a host in an organic emissive layer, the OLED showed enhanced EQE without deteriorating color purity, thus the OLED and organic light emitting display device including the OLED improves their luminous efficiencies and luminous lifetimes.

It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

What is claimed is:

1. An organic compound having the following structure of Chemical Formula 1:

[Chemical Formula 1]

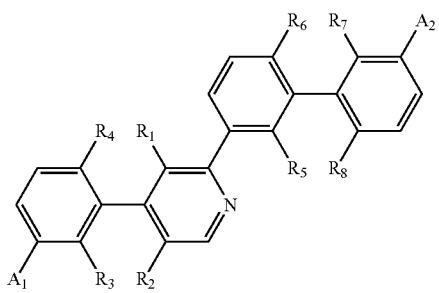

wherein each of $R_1$ to $R_8$ is independently protium, deuterium, tritium, $C_1$-$C_{10}$ alkyl, $C_6$-$C_{30}$ aryl or $C_3$-$C_{30}$ hetero aryl; and each of $A_1$ and $A_2$ is independently selected from the group consisting of unsubstituted or substituted carbazolyl, unsubstituted or substituted dibenzofuryl, and unsubstituted or substituted dibenzothiophenyl.

2. The organic compound of claim 1, wherein at least one of $R_1$ to $R_4$ is selected from the group consisting of $C_1$-$C_{10}$ alkyl, $C_6$-$C_{30}$ aryl and $C_3$-$C_{30}$ hetero aryl and at least one of $R_5$ to $R_8$ is selected from the group consisting of $C_1$-$C_{10}$ alkyl, $C_6$-$C_{30}$ aryl and $C_3$-$C_{30}$ hetero aryl.

3. The organic compound of claim 1, each of $A_1$ and $A_2$ is independently selected from the following structure of Chemical Formula 2:

[Chemical Formula 2]

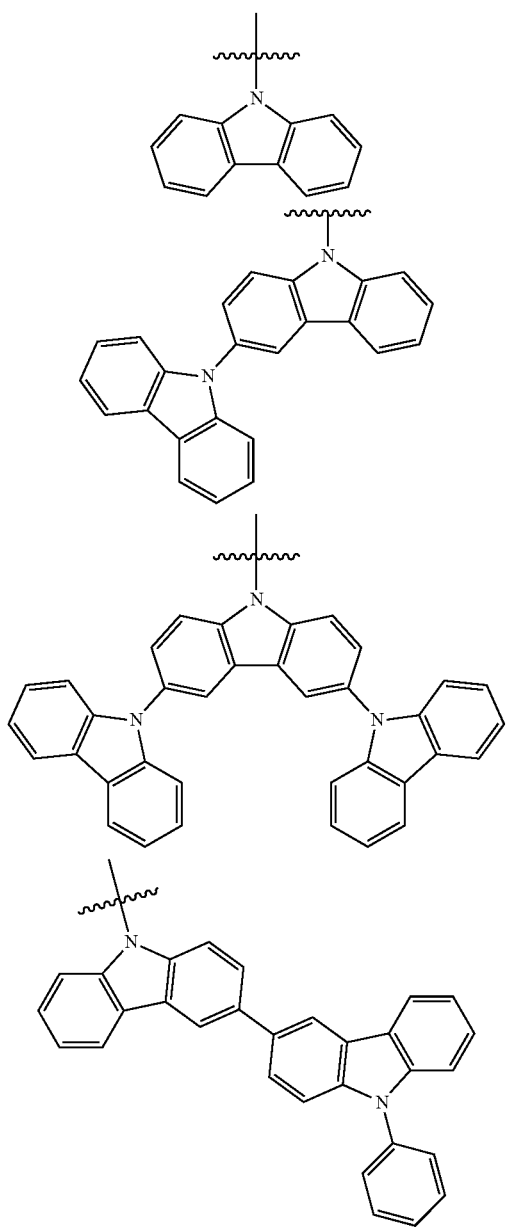

-continued

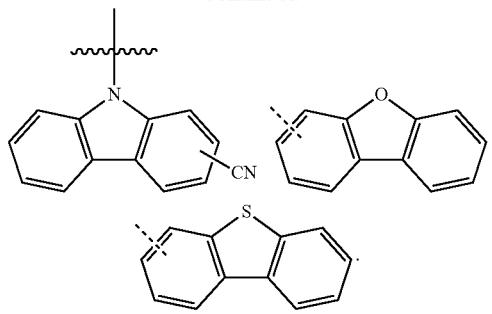

4. The organic compound of claim 2, wherein each of $R_1$ and $R_5$, $R_2$ and $R_6$, $R_3$ and $R_7$, $R_4$ and $R_8$ is identical.

5. The organic compound of claim 1, wherein the organic compound has one of the following structure of Chemical Formula 3:

[Chemical Formula 3]

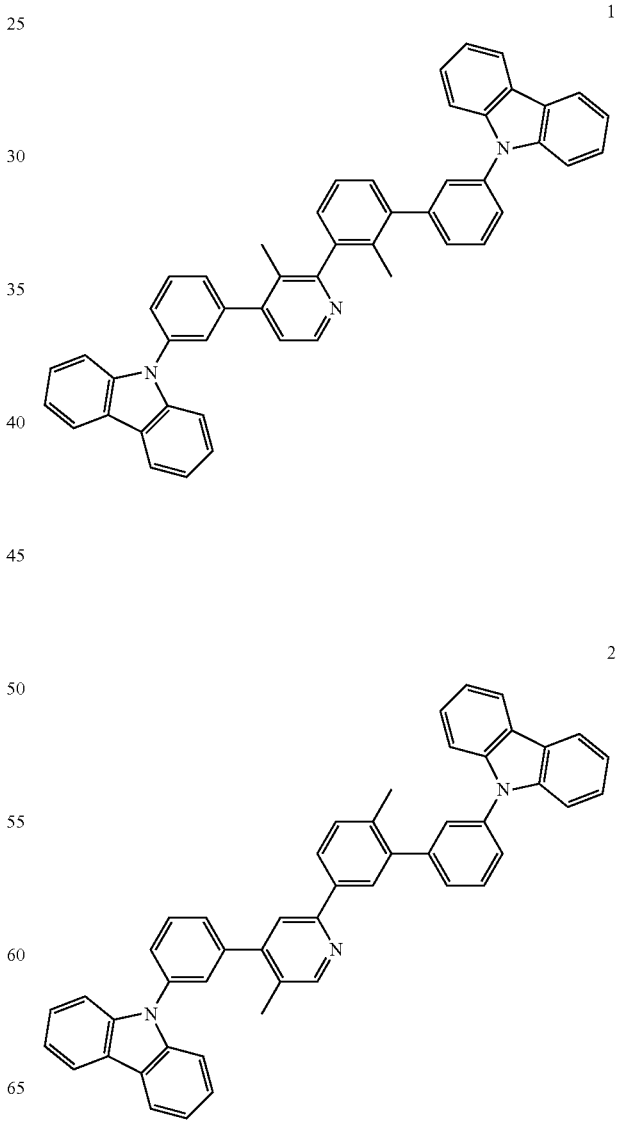

-continued
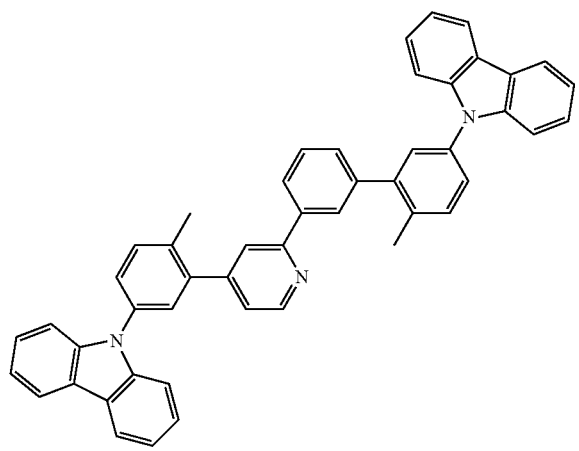
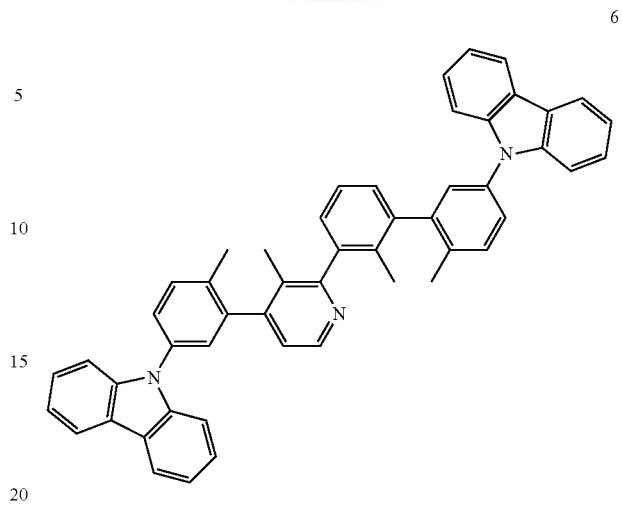
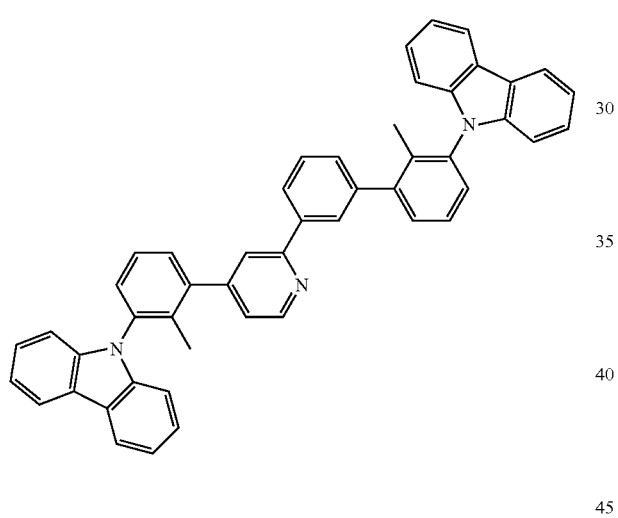
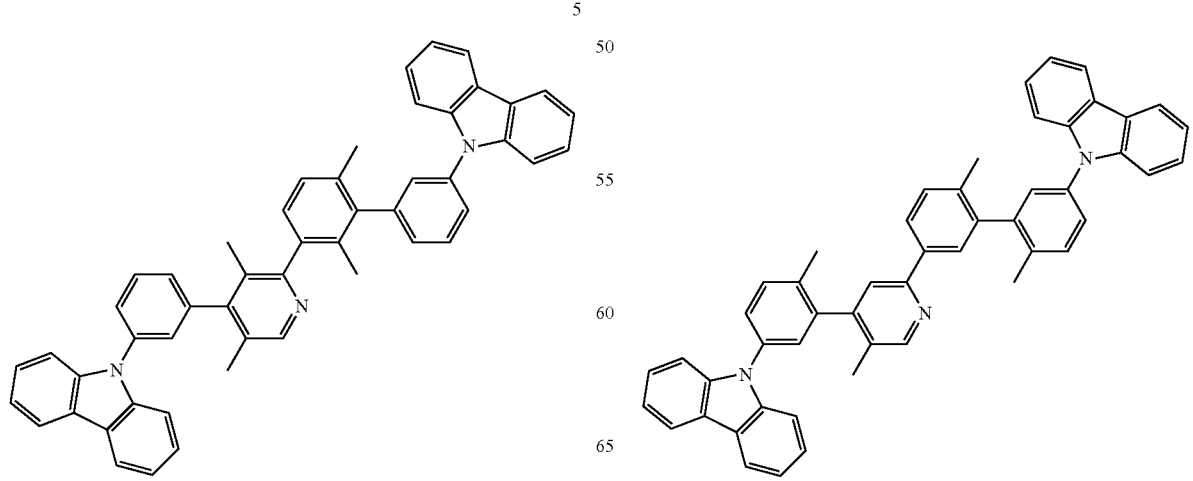

-continued
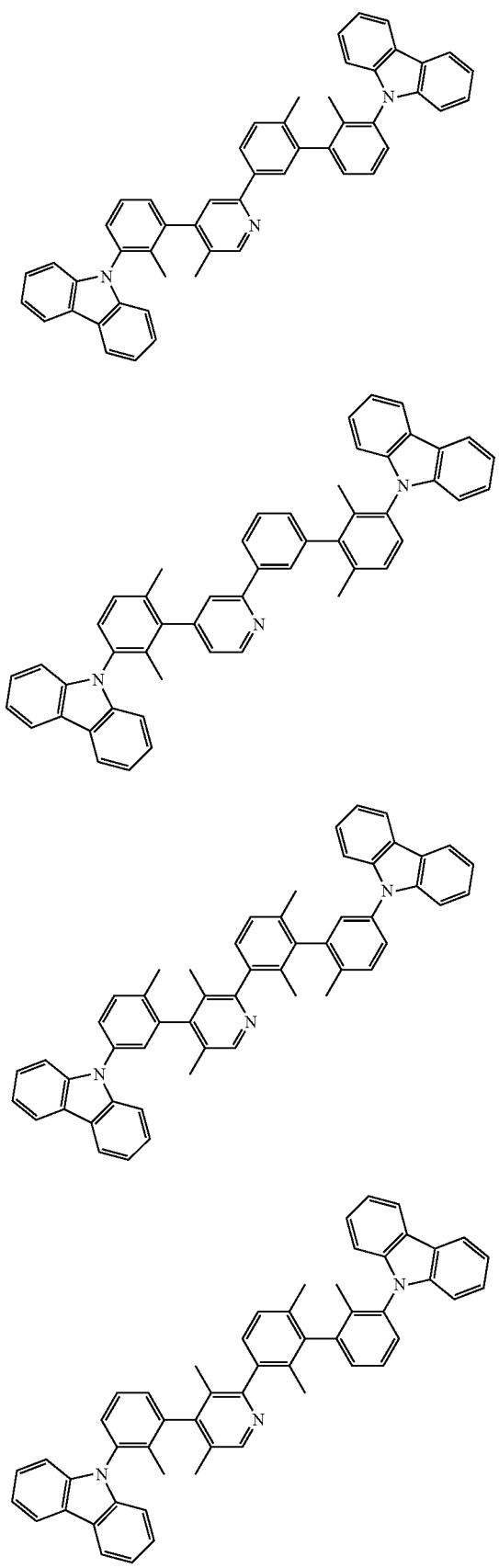
-continued
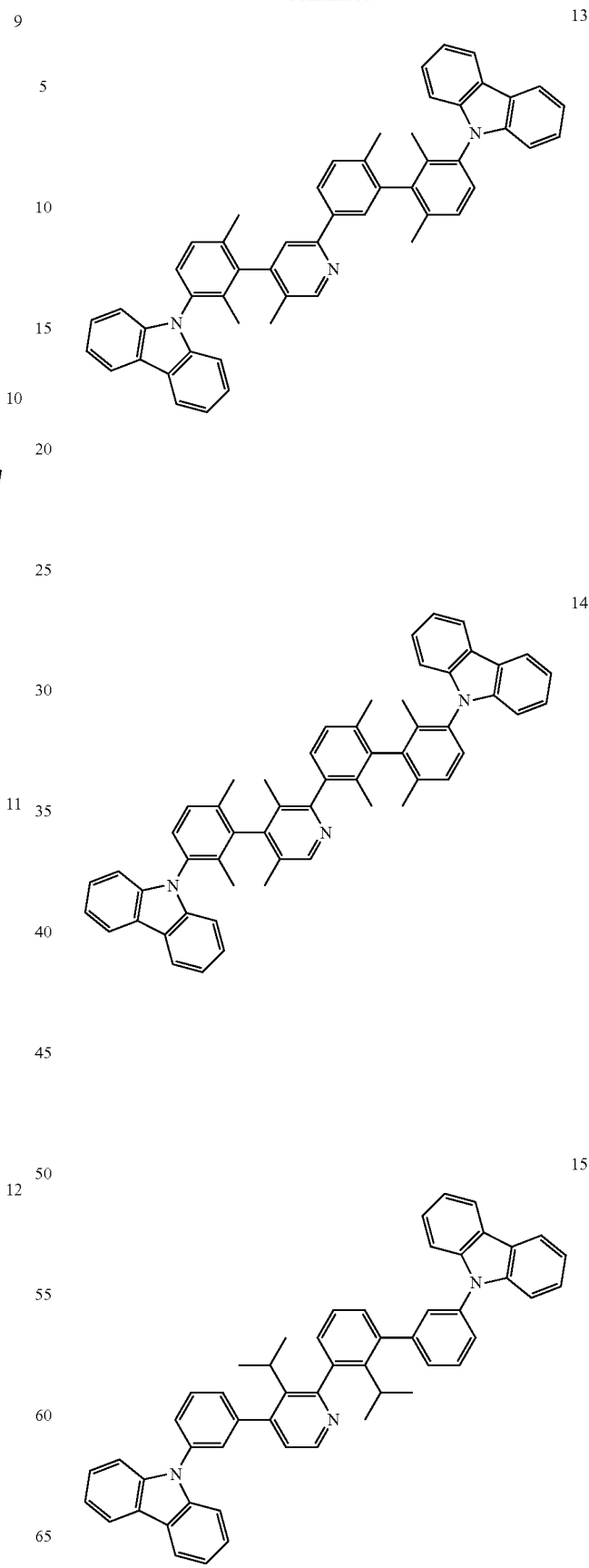

16
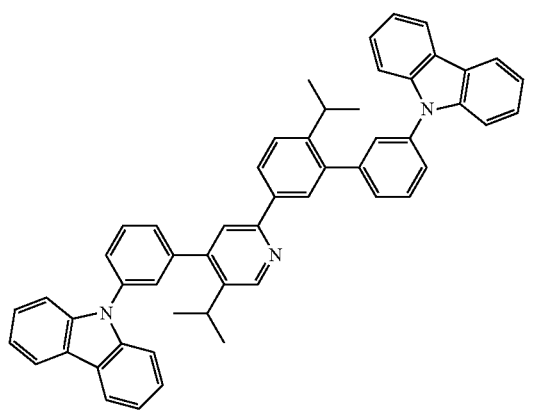
17
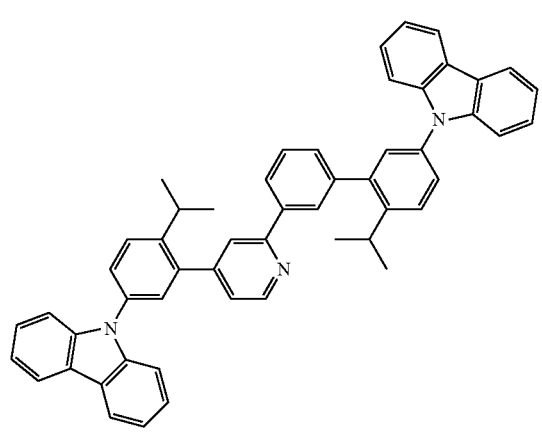
18
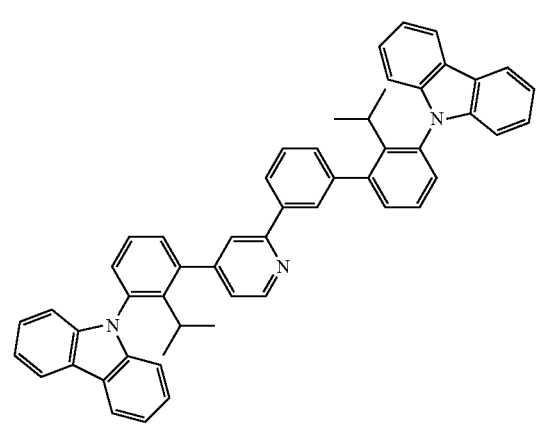
19
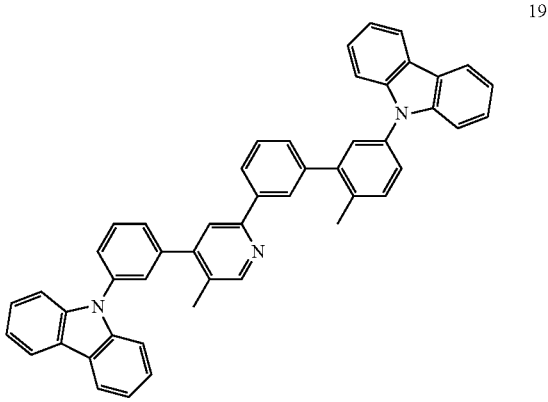
20
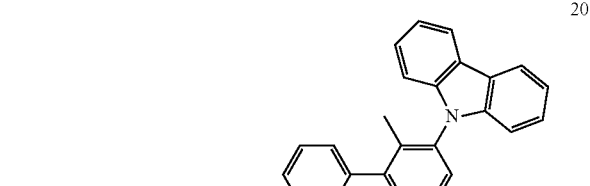
21
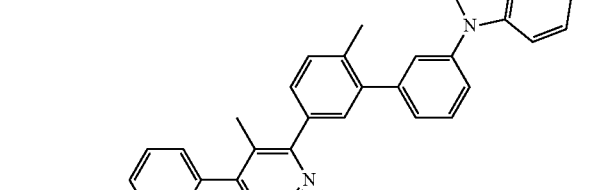
22
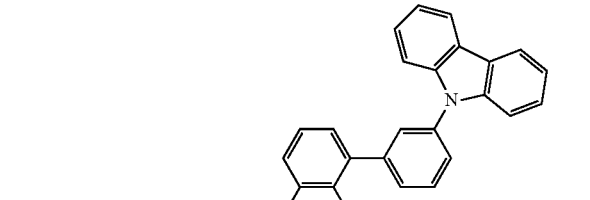

23
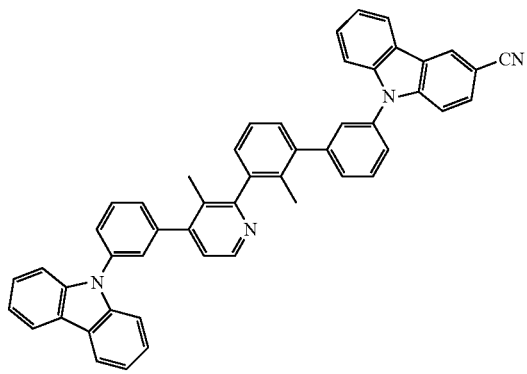
24
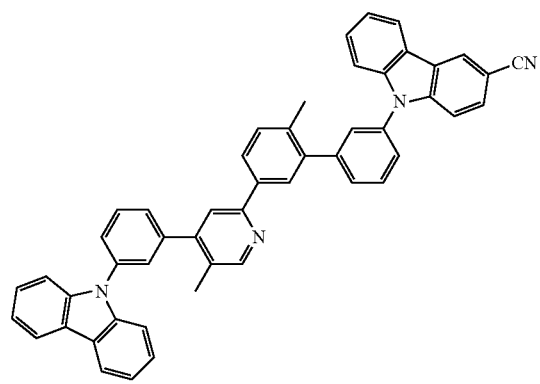
25
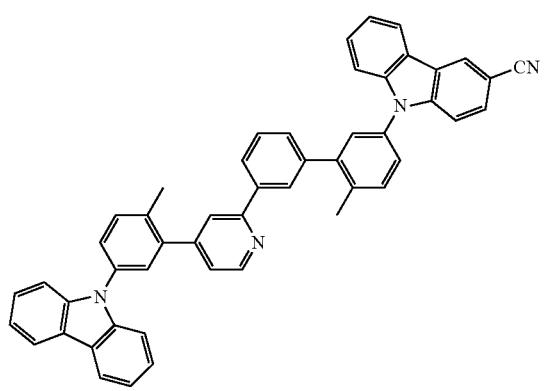
26
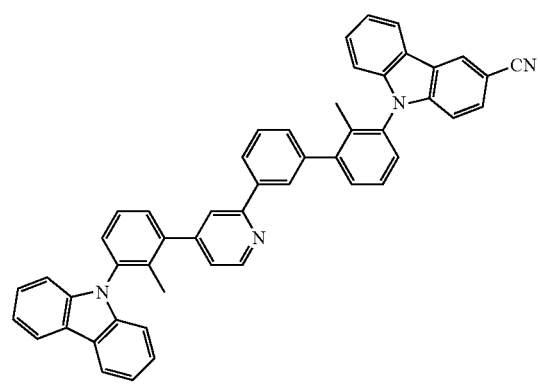
27
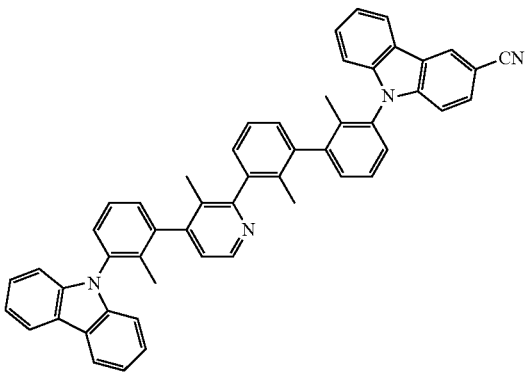
28
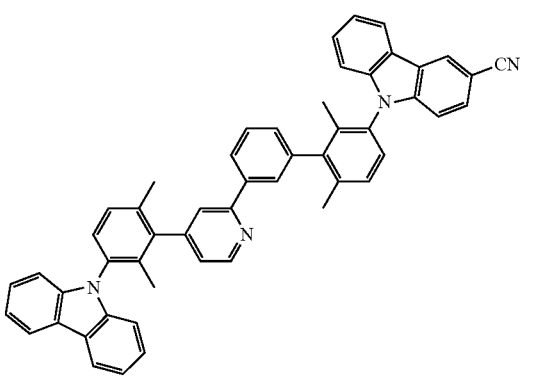
29
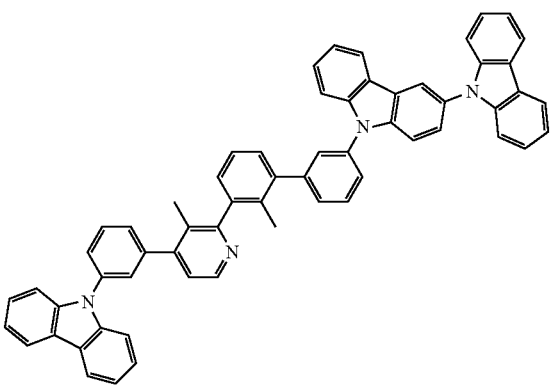
30
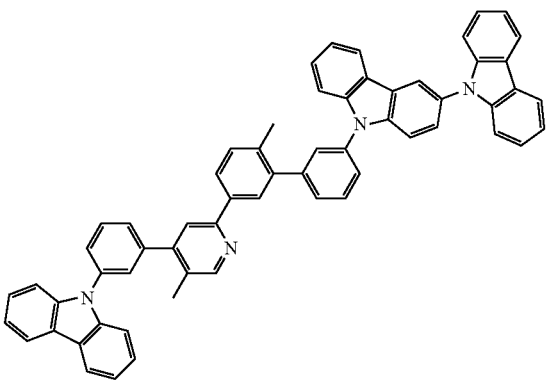

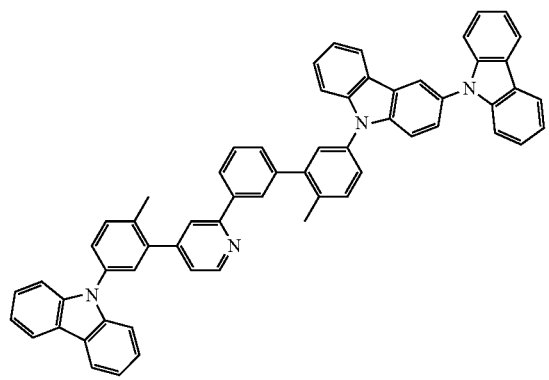
31
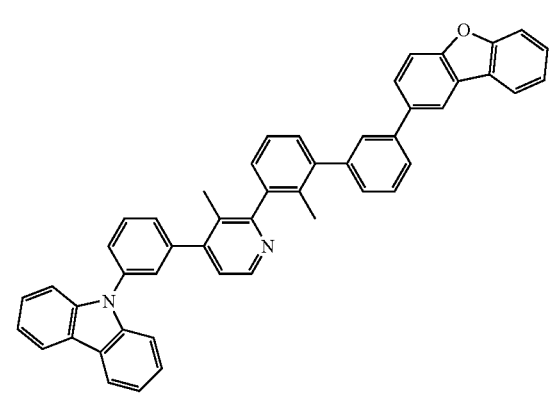
35
32
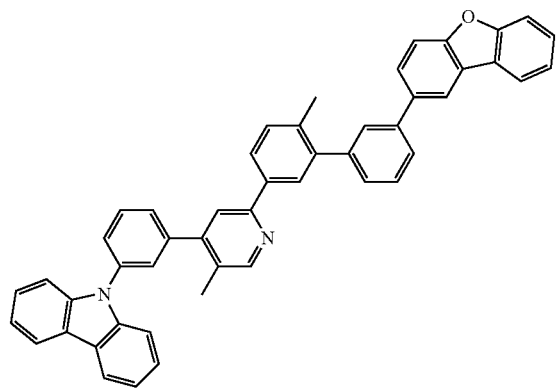
36
33
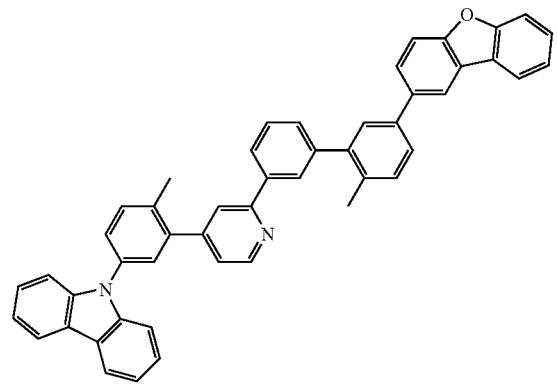
37
34
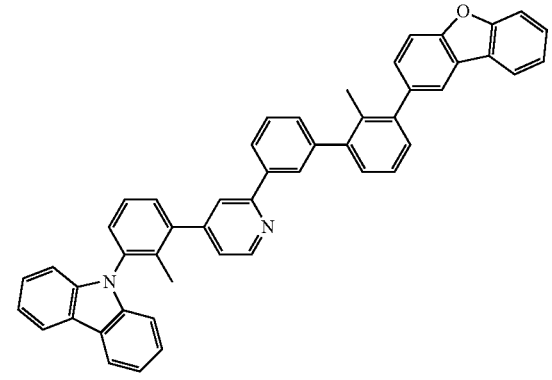
38

-continued

39

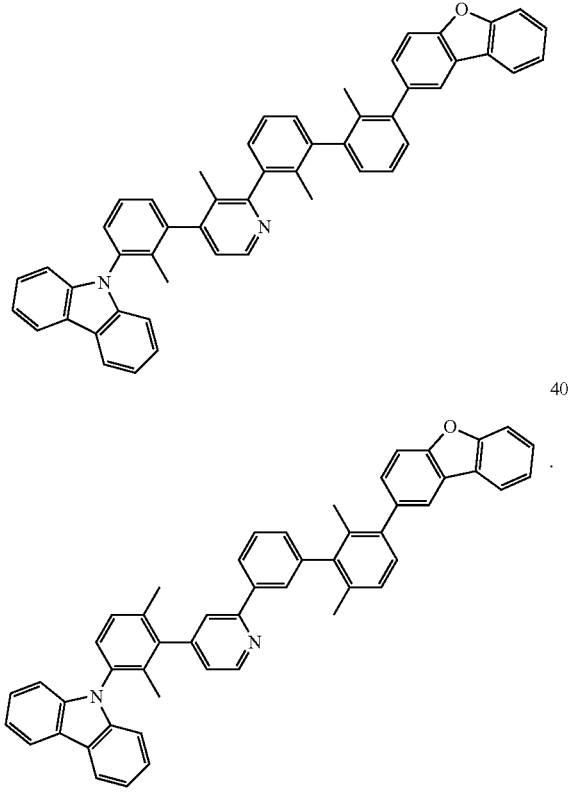

40

6. An organic light emitting diode, comprising:
a first electrode;
a second electrode facing the first electrode; and
an organic emissive layer comprising a first emitting material layer disposed between the first electrode and the second electrode,
wherein the first emitting material layer comprise an organic compound having the following structure of Chemical Formula 1:

[Chemical Formula 1]

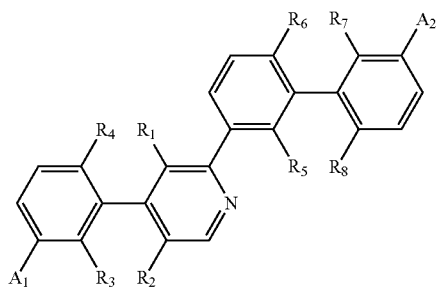

wherein each of $R_1$ to $R_8$ is independently protium, deuterium, tritium, $C_1$-$C_{10}$ alkyl, $C_6$-$C_{30}$ aryl or $C_3$-$C_{30}$ hetero aryl; and each of $A_1$ and $A_2$ is independently selected from the group consisting of unsubstituted or substituted carbazolyl, unsubstituted or substituted dibenzofuryl, and unsubstituted or substituted dibenzothiophenyl.

7. The organic light emitting diode of claim 6, wherein at least one of $R_1$ to $R_4$ is selected from the group consisting of $C_1$-$C_{10}$ alkyl, $C_6$-$C_{30}$ aryl and $C_3$-$C_{30}$ hetero aryl and at least one of $R_5$ to $R_8$ is selected from the group consisting of $C_1$-$C_{10}$ alkyl, $C_6$-$C_{30}$ aryl and $C_3$-$C_{30}$ hetero aryl.

8. The organic light emitting diode of claim 6, each of $A_1$ and $A_2$ is independently selected from the following Chemical Formula 2:

[Chemical Formula 2]

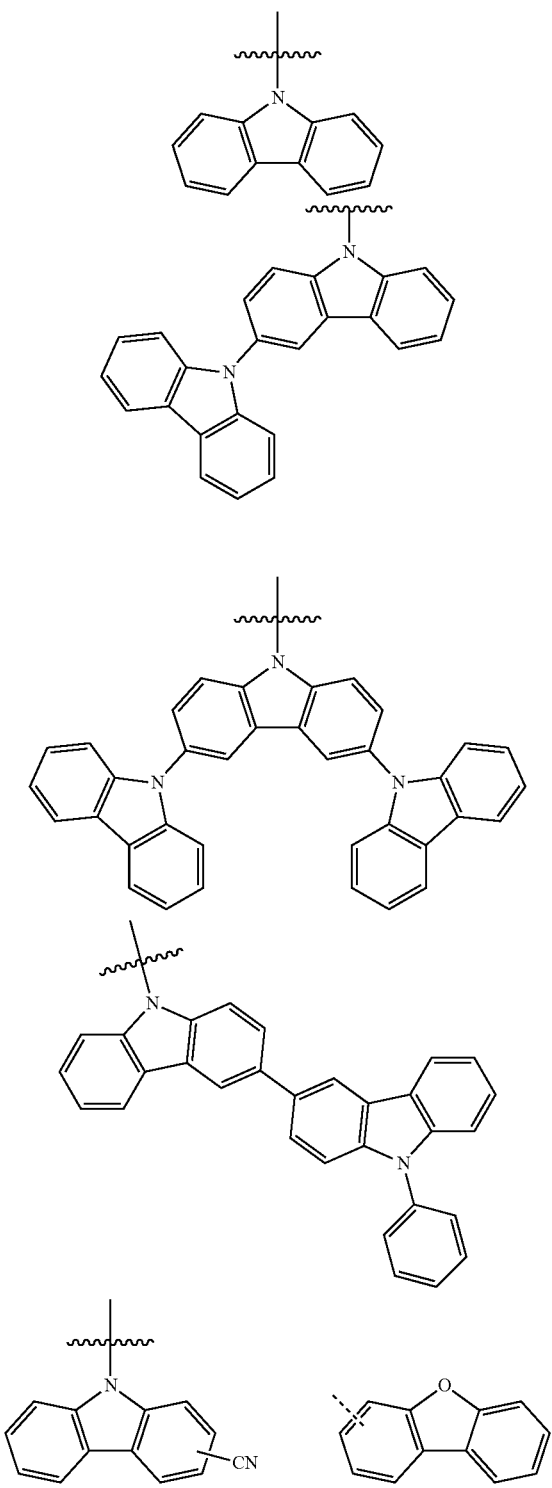

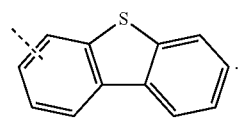
9. The organic light emitting diode of claim 6, wherein each of $R_1$ and $R_5$, $R_2$ and $R_6$, $R_3$ and $R_7$, $R_4$ and $R_8$ is identical.
10. The organic light emitting diode of claim 6, wherein the organic compound has one of the following structure of Chemical Formula 3:
[Chemical Formula 3]
1
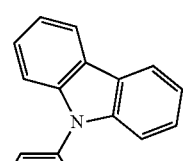
2
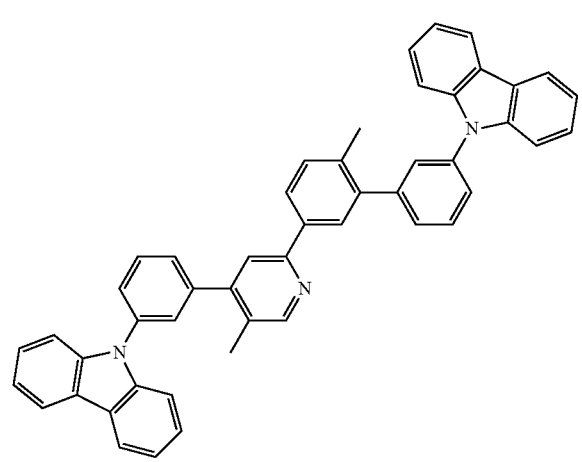
3
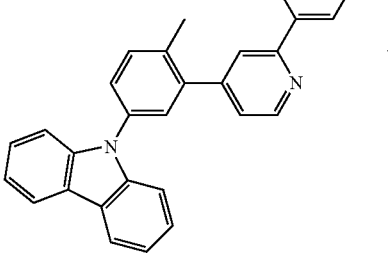
4
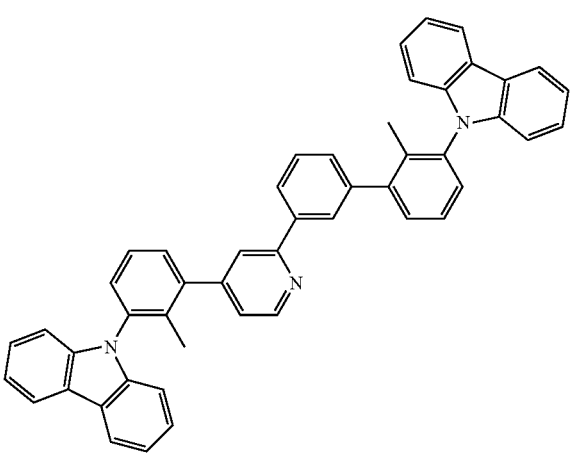
5
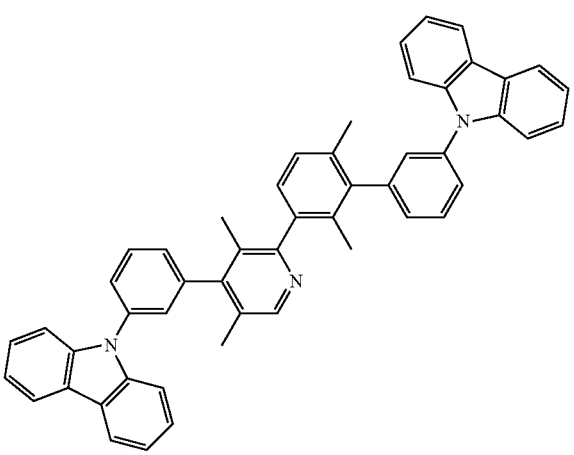

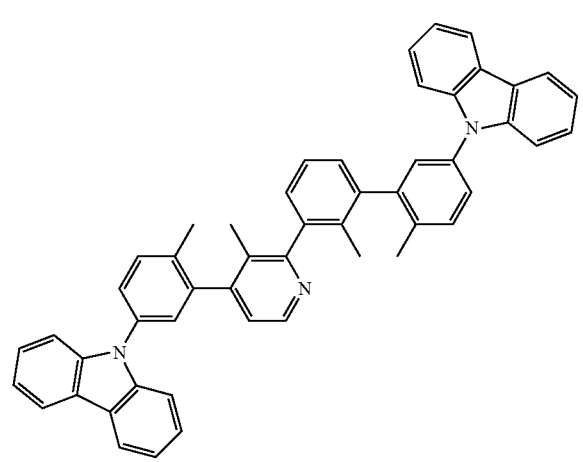
6
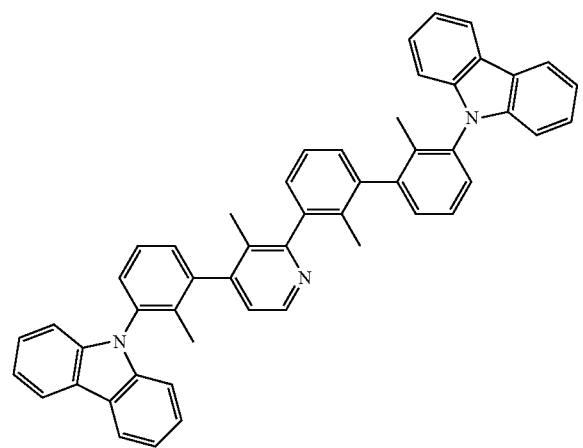
7
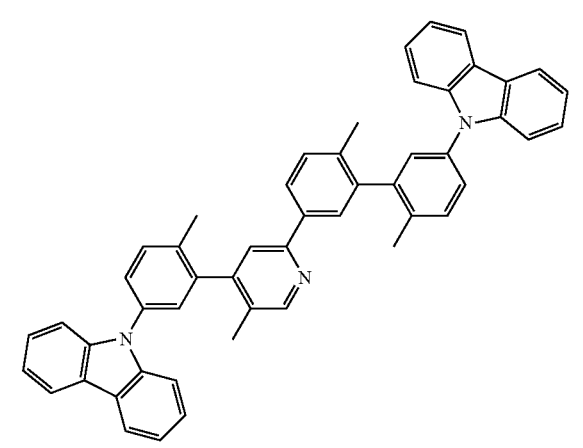
8
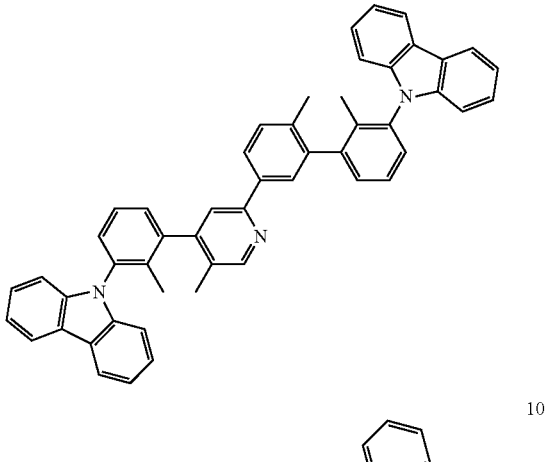
9
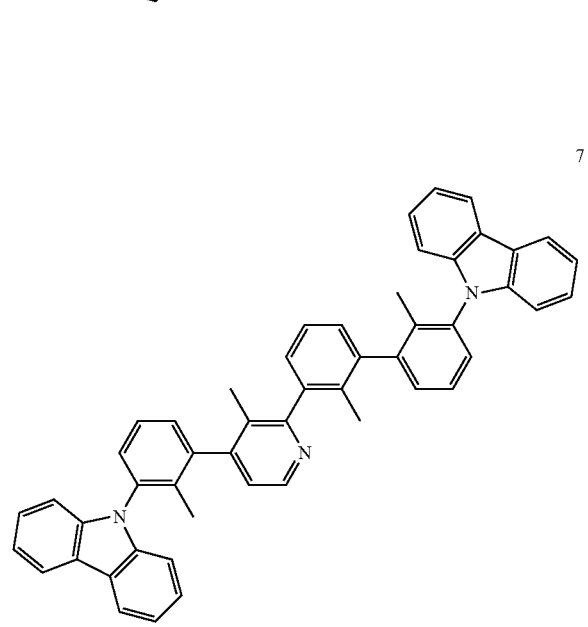
10
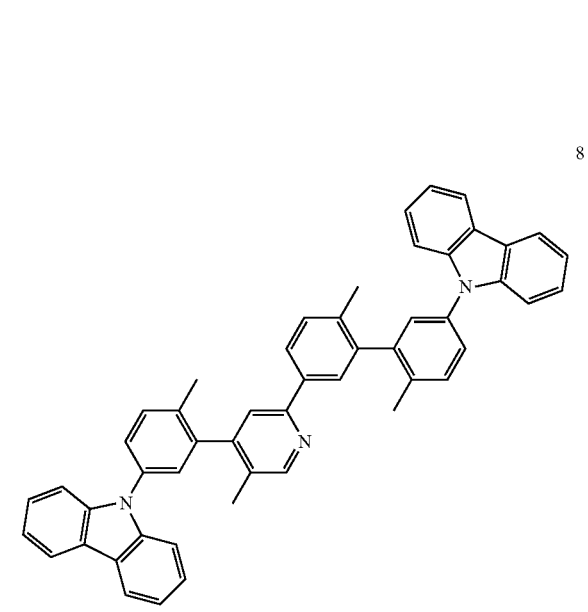
11
12

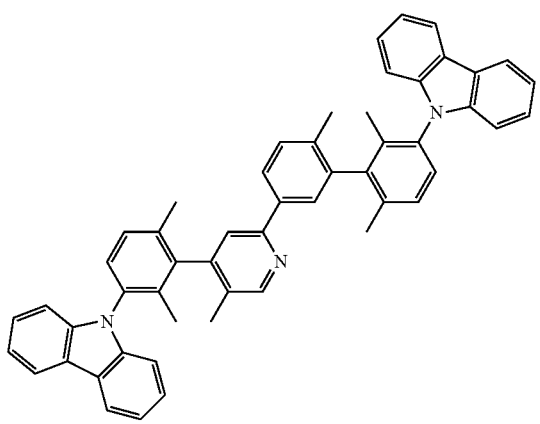
13
14
15
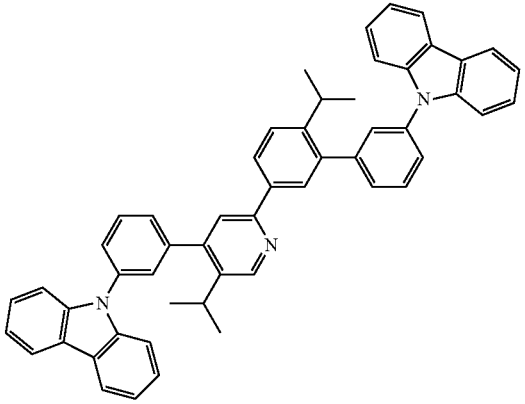
16
17
18

19
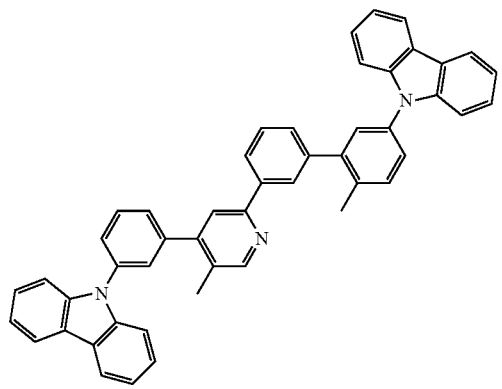
20
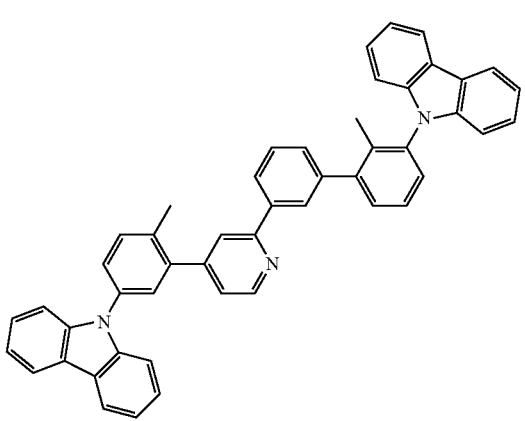
21
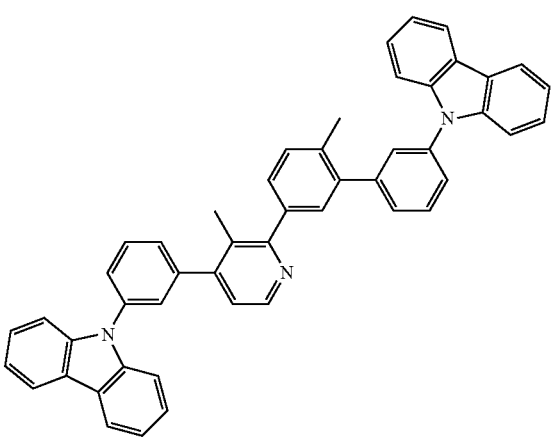
22
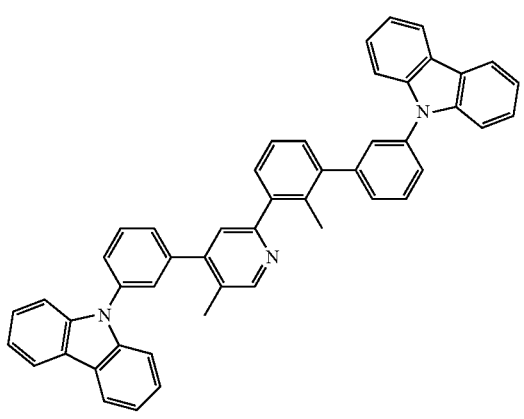
23
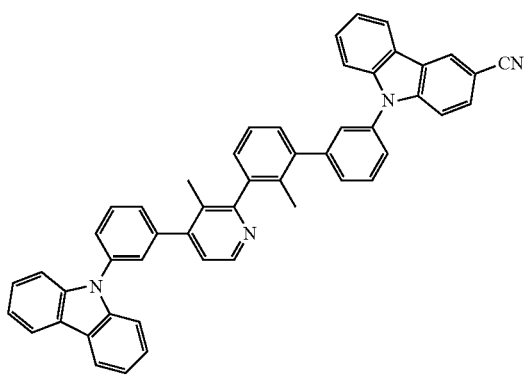
24
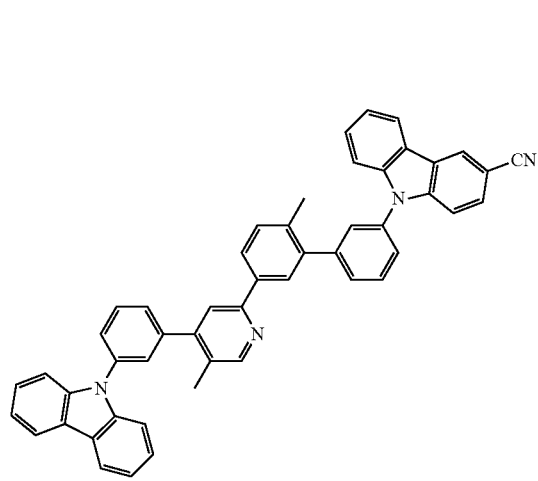
25
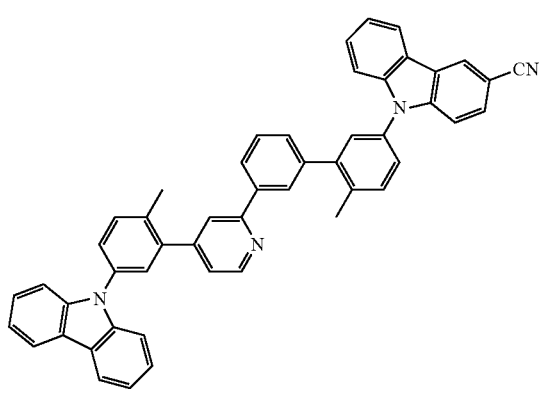
26
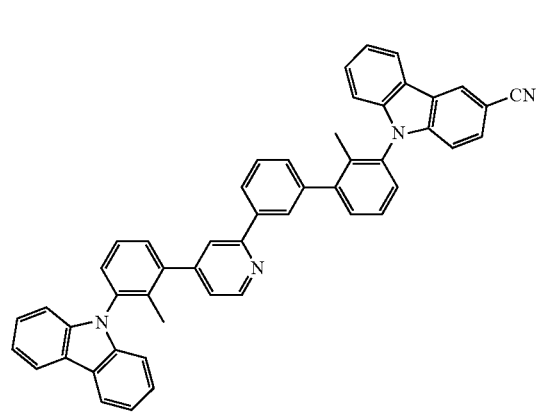

27
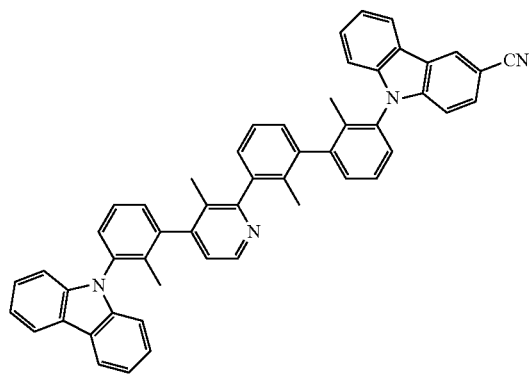
28
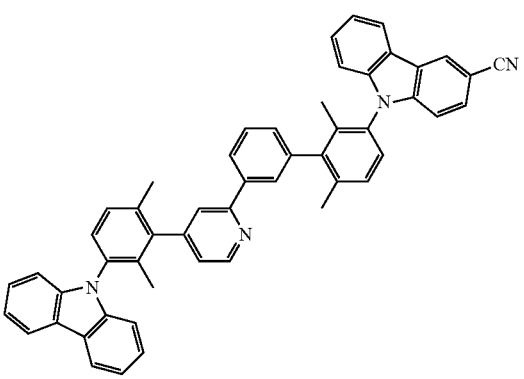
29
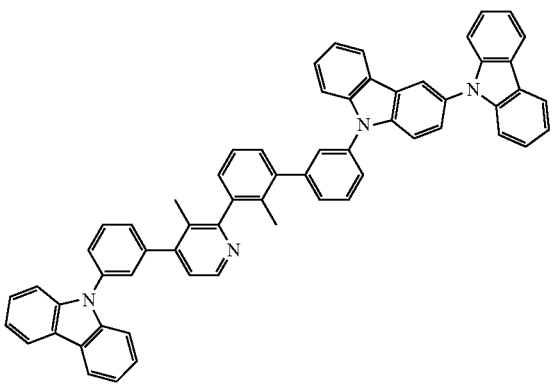
30
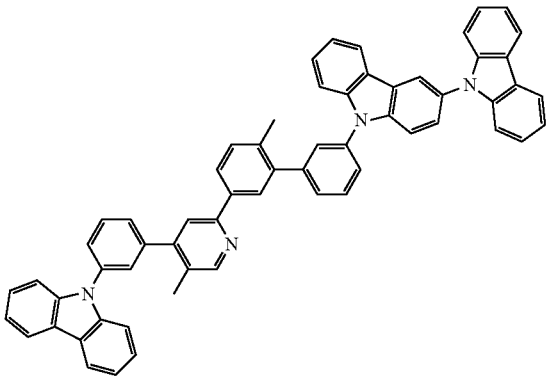
31
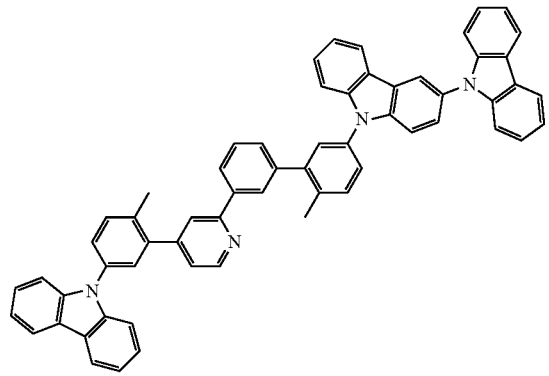
32
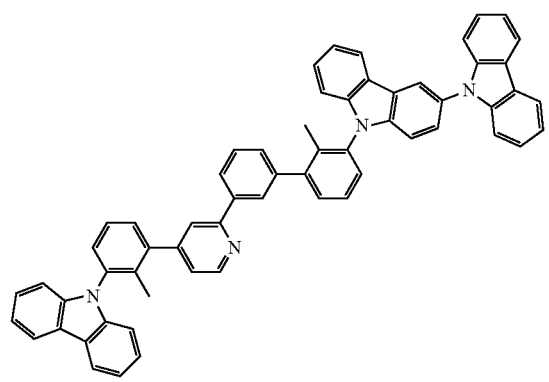
33
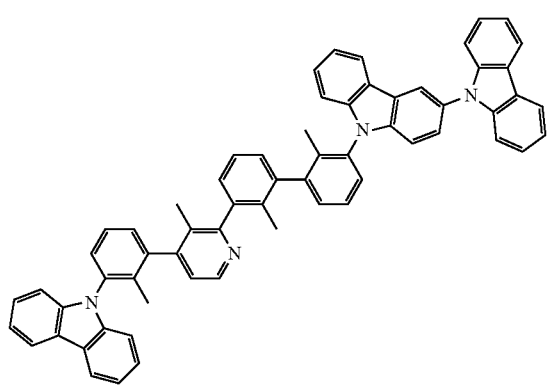
34
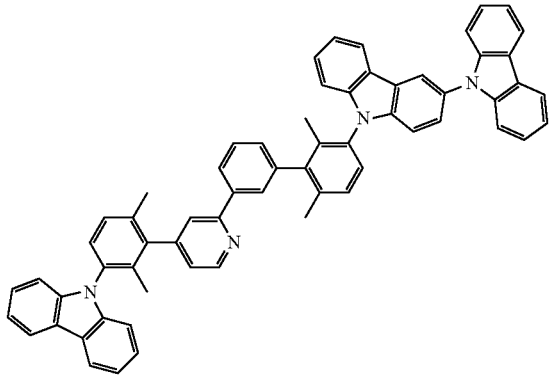

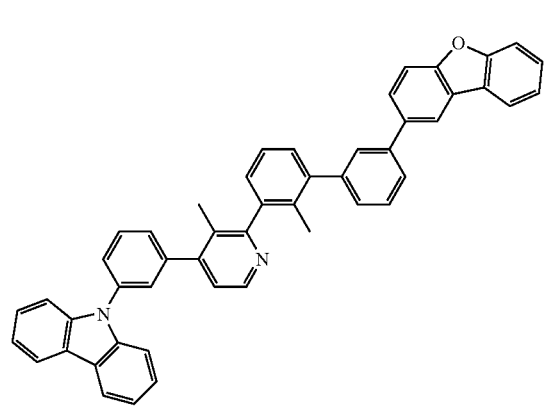

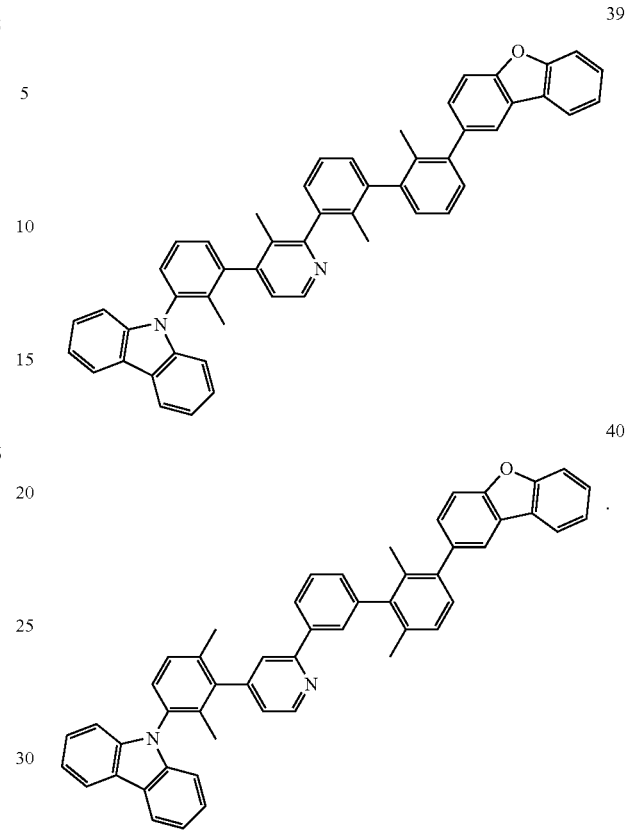

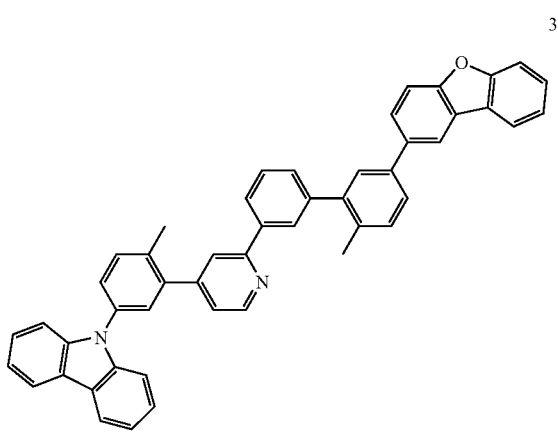

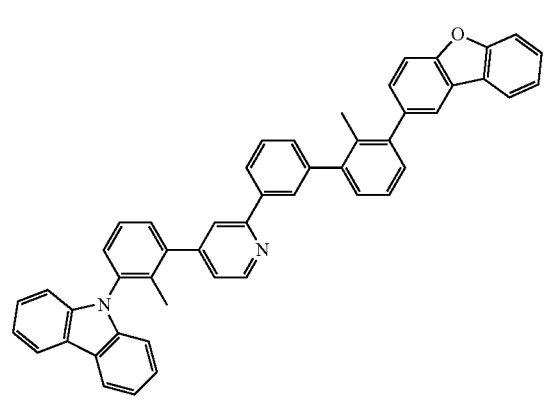

11. The organic light emitting diode of claim 6, wherein the first emitting material layer comprises a first host and a first dopant, and wherein the first host comprises the organic compound and the first dopant comprises delayed fluorescent material.

12. The organic light emitting diode of claim 11, wherein an energy level bandgap ($|HOMO_{HOST}-HOMO_{DOPANT}|$) between a HOMO energy level ($HOMO_{HOST}$) of the first host and a HOMO energy level ($HOMO_{DOPANT}$) of the first Dopant, or an energy level bandgap ($|LUMO_{HOST}-LUMO_{DOPANT}|$) between a LUMO energy level ($LUMO_{HOST}$) of the first host and a LUMO energy level ($LUMO_{DOPANT}$) of the first dopant is equal to or less than about 0.5 eV.

13. The organic light emitting diode of claim 11, the first emitting material layer further comprises a second dopant, and wherein an excited singlet energy level of the first dopant is higher than an excited singlet energy level of the second dopant.

14. The organic light emitting diode of claim 13, an excited triplet energy level of the first dopant is lower than an excited triplet energy level of the first host and higher than an excited triplet energy level of the second dopant.

15. The organic light emitting diode of claim 11, further comprises a second emitting material layer disposed between the first electrode and the second electrode, wherein the second emitting material layer comprises a second host and a second dopant, and wherein the second dopant comprises a fluorescent material.

16. The organic light emitting diode of claim 15, wherein an excited singlet energy level of the first dopant is higher than an excited singlet energy level of the second dopant.

17. The organic light emitting diode of claim 15, further comprises a hole blocking layer disposed between the first electrode and the second electrode, and wherein the first host is identical to the second host.

18. The organic light emitting diode of claim 15, further comprises an electron blocking layer disposed between the first electrode and the second electrode, and wherein the first host is identical to the second host.

19. The organic light emitting diode of claim 15, further comprises a third emitting material layer disposed between the first electrode and the second electrode, wherein the third emitting material layer comprises a third host and a third dopant, and wherein the third dopant is fluorescent material.

20. The organic light emitting diode of claim 19, wherein an excited singlet energy level of the first dopant is higher than excited singlet energy levels of the second and third dopants.

21. The organic light emitting diode of claim 19, wherein each of an excited singlet energy level and an excited triplet energy level of the first host is higher than each of an excited singlet energy level and an excited triplet energy level of the first dopant, respectively, wherein an excited singlet energy level of the second host is higher than an excited singlet energy level of the second dopant, and wherein an excited singlet energy level of the third host is higher than an excited singlet energy level of the third dopant.

22. The organic light emitting diode of claim 6, wherein the organic emissive layer further comprises a hole injection layer, a hole transport layer and an electron blocking layer each of which is disposed between the first electrode and the first emitting material layer, and an electron injection layer, an electron transport layer and a hole blocking layer each of which is disposed between the second electrode and the first emitting material layer, and wherein the organic compound is a first host in the first emitting material layer.

23. An organic light emitting device, comprising:
a substrate; and
an organic light emitting diode of claim 6 over the substrate.

24. The organic light emitting diode of claim 23, wherein at least one of $R_1$ to $R_4$ is selected from the group consisting of $C_1$-$C_{10}$ alkyl, $C_6$-$C_{30}$ aryl and $C_3$-$C_{30}$ hetero aryl and at least one of $R_5$ to $R_8$ is selected from the group consisting of $C_1$-$C_{10}$ alkyl, $C_6$-$C_{30}$ aryl and $C_3$-$C_{30}$ hetero aryl.

\* \* \* \* \*